(12) United States Patent
Hall et al.

(10) Patent No.: US 12,075,874 B2
(45) Date of Patent: *Sep. 3, 2024

(54) PERSONAL AIR FILTRATION SYSTEM WITH SMART APP

(71) Applicant: Hall Labs LLC, Provo, UT (US)

(72) Inventors: Michael Hall, Provo, UT (US); David R. Hall, Provo, UT (US); Chandler Flinders, Provo, UT (US); Jordan Englund, Provo, UT (US); Jacob Dean, Provo, UT (US); Vicente Oliveira, Orem, UT (US); Anthony E. Pullen, Tucson, AZ (US); Jeff Duncan, Tucson, AZ (US)

(73) Assignee: MicroClimate, Inc., Provo, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/209,191

(22) Filed: Mar. 22, 2021

(65) Prior Publication Data

US 2021/0289851 A1 Sep. 23, 2021

Related U.S. Application Data

(60) Provisional application No. 63/105,830, filed on Oct. 26, 2020, provisional application No. 63/053,519, (Continued)

(51) Int. Cl.
*A42B 3/28* (2006.01)
*A41D 13/11* (2006.01)
(Continued)

(52) U.S. Cl.
CPC .......... *A42B 3/286* (2013.01); *A41D 13/1153* (2013.01); *A42B 3/06* (2013.01); *A42B 3/283* (2013.01); *A42B 3/285* (2013.01); *A42B 3/288* (2013.01); *A61F 11/14* (2013.01); *A62B 7/10* (2013.01); *A62B 9/00* (2013.01); *A62B 9/006* (2013.01); *A62B 17/003* (2013.01); *A62B 17/04* (2013.01); *A62B 18/045* (2013.01); *A62B 18/08* (2013.01); *B01D 39/083* (2013.01); *B01D 46/0093* (2013.01); *B01D 46/44* (2013.01); *G02F 1/0126* (2013.01);
(Continued)

(58) Field of Classification Search
CPC .... A42B 3/286; A41D 13/1153; A62B 18/045
See application file for complete search history.

(56) References Cited

U.S. PATENT DOCUMENTS 5,054,480 A * 10/1991 Bare ..................... A41D 13/11
128/206.28
6,081,929 A * 7/2000 Rothrock ............... A42B 3/286
2/424
(Continued)

*Primary Examiner* — Heather Mangine
*Assistant Examiner* — Erick I Lopez

(57) ABSTRACT

A personal air filtration system comprising a rigid component, a flexible component, wherein the rigid component and the flexible component combine to cover at least a user's mouth and nostrils and form a seal therearound, an intake port with an inlet filter, an exhaust port, an air mover causing filtered air to enter the intake port and exhaust air to exit the exhaust port, and an app running on a user's smart device, wherein a smart app is configured to control and monitor operation of the system.

21 Claims, 35 Drawing Sheets

Related U.S. Application Data filed on Jul. 17, 2020, provisional application No. 62/992,277, filed on Mar. 20, 2020.

(51) Int. Cl.
| | |
|---|---|
| *A42B 3/06* | (2006.01) |
| *A61F 11/14* | (2006.01) |
| *A62B 7/10* | (2006.01) |
| *A62B 9/00* | (2006.01) |
| *A62B 17/00* | (2006.01) |
| *A62B 17/04* | (2006.01) |
| *A62B 18/04* | (2006.01) |
| *A62B 18/08* | (2006.01) |
| *B01D 39/08* | (2006.01) |
| *B01D 46/00* | (2022.01) |
| *B01D 46/44* | (2006.01) |
| *G02F 1/01* | (2006.01) |
| *G02F 1/1524* | (2019.01) |

(52) U.S. Cl.
CPC .... *G02F 1/1524* (2019.01); *B01D 2239/0457* (2013.01); *B01D 2273/30* (2013.01)

(56) References Cited

U.S. PATENT DOCUMENTS

| | | | | |
|---|---|---|---|---|
| 6,751,807 | B2* | 6/2004 | Klotz | A42B 3/286 |
| | | | | 2/171.3 |
| 6,990,691 | B2* | 1/2006 | Klotz | A42B 3/286 |
| | | | | 2/901 |
| 8,302,599 | B2* | 11/2012 | Green | A62B 18/045 |
| | | | | 128/201.24 |
| 2019/0175961 | A1* | 6/2019 | Awiszus | A42B 3/0466 |

* cited by examiner

PERSONAL AIR FILTRATION SYSTEM WITH SMART APP

CROSS-REFERENCE TO RELATED APPLICATIONS

This application claims priority to U.S. Provisional Patent Application No. 62/992,277 titled "Head Covering Device" filed on Mar. 20, 2020, U.S. Provisional Patent Application No. 63/053,519 titled "Head Covering Device with Negative Air Flow", U.S. Provisional Patent Application No. 63/053,523 titled "Head Covering Device with Environmental Control", U.S. Provisional Patent Application No. 63/053,526 titled "Head Covering Device with a Communication Component", U.S. Provisional Patent Application No. 63/053,537 titled "Head Covering Device with Automatic Air Moving System", U.S. Provisional Patent Application No. 63/053,542 titled "Head Covering Device with Shroud", U.S. Provisional Patent Application No. 63/053,546 titled "Head Covering Device with Washable Filtering Fabric", U.S. Provisional Patent Application No. 63/053,548 titled "Head Covering Device with Electromagnetic Radiation Filtering Face Shield", U.S. Provisional Patent Application No. 63/053,552 titled "Protective Mask with Negative Air Flow" filed on Jul. 17, 2020, and U.S. Provisional Patent Application No. 63/105,830 titled "Head Covering Device" filed on Oct. 26, 2020, which are incorporated herein by reference in their entirety.

TECHNICAL FIELD

The present disclosure relates to personal air filtration systems.

BACKGROUND

Head covering devices (HCDs) on the market, such as helmets, are typically designed for some type of injury prevention. For example, personal protection equipment (PPE) for the head is commonly construction helmets or welder's helmets. Recreational protective head gear includes motorcycle helmets and sports helmets such as helmets for skiers, bikers, mountain climbers, baseball, and football players. Other types of HCDs include protection equipment such as splash shields and filters for firefighters, policemen, HAZMAT specialists, health care workers, and other first responders. In many cases, the HCDs are heavy, bulky and can be uncomfortable.

SUMMARY

One aspect of the present invention is a personal air filtration system comprising a rigid component, a flexible component, wherein the rigid component and the flexible component combine to cover at least a user's mouth and nostrils and form a seal therearound, an intake port with an inlet filter, an exhaust port, an air mover causing filtered air to enter the intake port and exhaust air to exit the exhaust port, and an app running on a user's smart device, wherein a smart app is configured to control and monitor operation of the system.

In another aspect of the invention, the smart device is integrated into the rigid component.

In a still further aspect, the smart device provides wireless communication for the user.

In a yet still further aspect, the smart device is a separate smart phone and may further comprise a microphone and speakers mounted to the rigid component, which microphone and speakers communicate wirelessly with the smart device to enable the user to place and receive telephone calls over the smart phone.

In another aspect, the smart device is a wearable smart device.

In another aspect of the invention, the smart device communicates wirelessly with a controller mounted to the rigid component, and wherein the controller is configured to control the rate of the air mover.

In still another aspect, the air mover is powered by a battery and the app is configured to monitor the status of the battery and provide information to the user on the status of the battery.

In a still further aspect, the rigid component comprises a transparent face shield and wherein the rigid component and flexible component combine to cover the user's head and seal around the user's neck.

In a still yet further aspect, the system further comprises a first microphone on an inner surface of the rigid component, a second microphone on an outer surface of the rigid component, a first speaker mounted on an inner surface of the rigid component, and a second speaker mounted on an outer surface of the rigid component, wherein the app is configured to facilitate oral communication by the user.

In another still yet further aspect, the app is configured to adjust volume based on ambient noise levels.

In another aspect of the invention, the device further comprises a video display projected on an inner surface of the transparent face shield and wherein the app is configured for the user to select and control the video display.

In still another aspect, the device further comprises a shade function whereby the amount of electromagnetic radiation entering through the transparent face shield can be reduced, and wherein the app is configured to control the shade function based upon instructions from the user and signals from electromagnetic radiation sensors.

In a still further aspect, the device the system further comprises sensors to detect leaks in the seal and wherein the app receives signals from the sensors to test and/or monitor fitment of the system. The sensors may detect a gas used in testing fitment.

In a yet still further aspect, the app is configured to provide an intercom with a second user of a similar system.

In another aspect of the invention, the app is further configured to provide filter end of useful life alerts to the user based on at least one of age of the filter, increased head pressure on the filter and optical readings indicating a dirty filter.

In still another aspect, the device further comprises biometric sensors and a processor for receiving signals from the biometric sensors and communicate biometric information to the smart device, and wherein the app is configured to receive and process biometric information and provide reports to the user.

In a still further aspect, the biometric sensors are configured to measure biometric information selected from the group consisting of body temperature, pulse rate, pulse oximetry, respiration rate, blink rate, head orientation and combinations thereof.

In a yet still further aspect, the smart device communicates wirelessly with a controller mounted to the rigid component, and wherein the controller is configured to control the rate of the air mover and wherein the app is configured to send signals to the controller to adjust the rate of the air mover in response to one or more types of biometric information.

In another still yet further aspect, the device further comprises a device for controlling the personal environment mounted to the rigid component, which is configured to adjust the temperature and/or the humidity around the user's head, and wherein the app is configured to allow the user to make those adjustments and configured to make those adjustments in response to biometric data and/or ambient environmental data.

Further aspects and embodiments are provided in the following drawings, detailed description, and claims. Unless specified otherwise, the features as described herein are combinable and all such combinations are within the scope of this disclosure.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Overview

Figure 1:
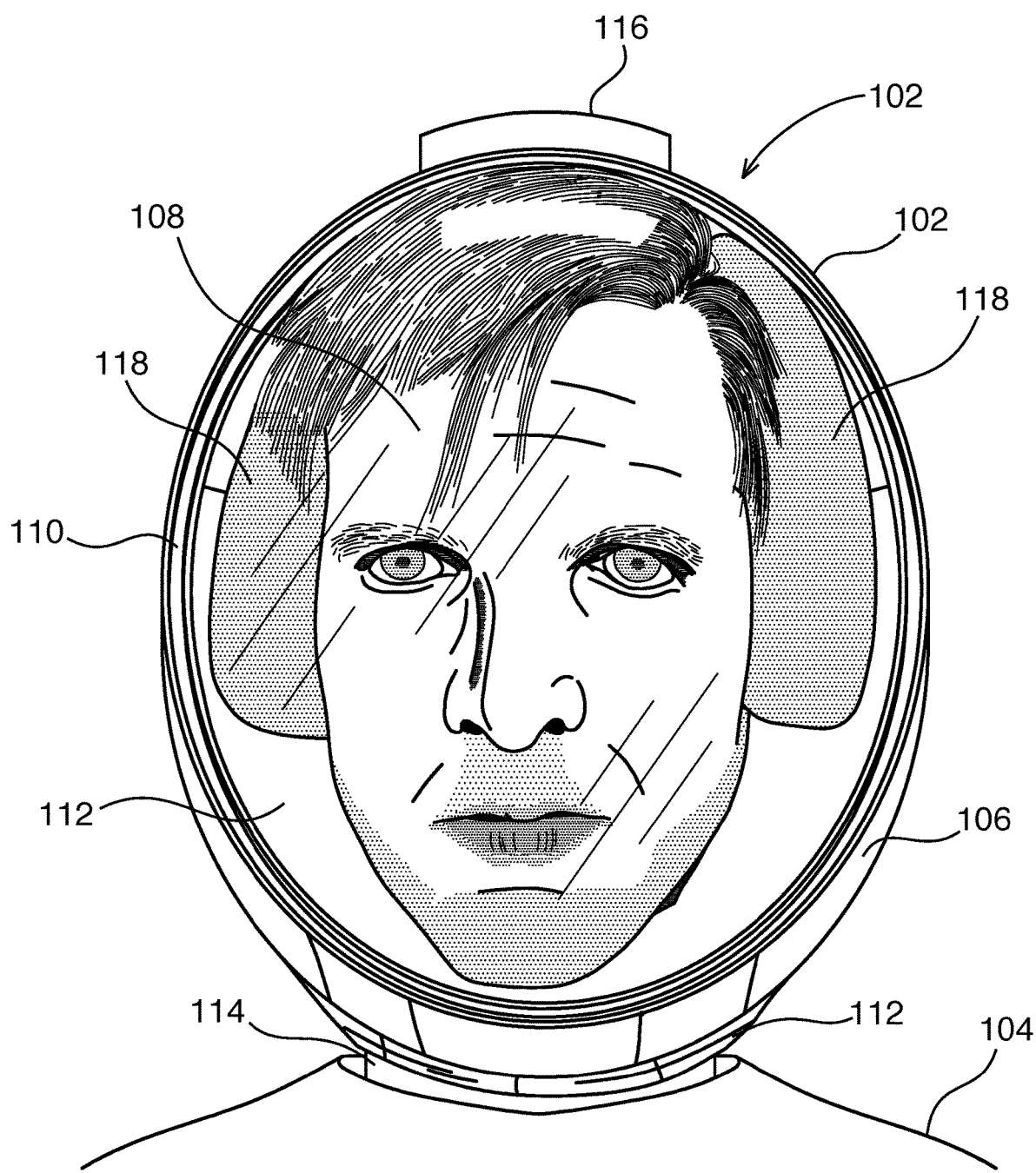
FIG. 1 is a front view of a user wearing a head covering device (HCD), according to an embodiment of the disclosure.

Embodiments of methods, materials and processes described herein are directed towards personal air filtration systems, such as head covering devices. Head covering devices can be used to provide a filtered air environment to a user to prevent a user from being infected with a contagious disease. Head covering devices may also filter the exhaust air to prevent a user from spreading a contagious disease.

Personal air filtration systems disclosed herein include a rigid component and a flexible component combined to completely cover the head of a user. The rigid component includes a frame and a transparent face shield. The flexible component includes a fabric that seals around the neck of a user. The disclosure herein describes various designs and components such as air movers and air filters to filter the air entering the device and the air being exhausted from the device that are controlled and monitored by a smart app on a smart device.

Definitions

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "user" refers to any individual who uses an HCD.

As used herein, the term "filter," as a noun, refers to a device, typically composed of fibrous or porous materials which removes unwanted components, usually in the form of particulates, such as dust, pollen, mold, viruses, and bacteria, from air. Filters containing an adsorbent or catalyst, such as charcoal (carbon), may also remove odors and gaseous pollutants such as volatile organic compounds or ozone. Air filters are generally used in applications where air quality is important. As a verb, "filter" refers to the act of removing particles from air.

As used herein, the term "transparent" is used in its normal sense, that is the property of allowing light to pass through so that behind can be distinctly seen therethrough. The transparent components described and defined below are preferably clear, but may be tinted, in whole or in part.

The term "negative air flow" is used to indicate that, in accordance with embodiments of the invention, air is actively pulled inside the HCD through an intake filter by an air mover and the air is exhausted out an exhaust filter.

The term "positive air flow" is used to indicate that, in accordance with embodiments of the invention, air is actively pulled inside the HCD by an air mover through an intake filter in the air mover and exhausted through an exhaust filter.

The term "neutral air flow" is used to indicate that, in accordance with embodiments of the invention, a substantially static flow of air is maintained in the HCD. The air flow into and out of the HCD is controlled by the breathing in and breathing out of the user.

As used herein, the term "thermoelectric cooler" refers to cooling devices that operate on the principle of the Peltier effect. A thermoelectric cooler may also be used for temperature control for both heating and cooling depending upon how it is arranged in a device.

As used herein, the term "Peltier effect" refers to the effect that creates a temperature difference by transferring heat between two electrical junctions. A voltage is applied across joined conductors to create an electric current. When the current flows through the junctions of the two conductors, heat is removed at one junction and cooling occurs. Heat is deposited at the other junction. The main application of the Peltier effect is cooling, though the Peltier effect can also be used for heating or control of temperature.

As used herein, the terms "energy recovery device" and "heat recovery device" refers to a device that operates on the basis of air-to-air exchange theory where two air-streams in contact and passing in opposite directions transfers heat/energy between the two air-streams.

As used herein, the term "phase-change material" or "PCM" refers to materials that use the heat of crystallization, melting or some other phase change to thereby either store heat in a predetermined temperature range or release heat in a predetermined lower temperature range.

As used herein, the term "polarizer" is an optical filter that lets light waves of a specific polarization pass through while blocking light waves of other polarizations. A polarizer can filter a beam of light of undefined or mixed polarization into a beam of well-defined polarization, that is polarized light.

As used herein, the term "photochromic" refers to a device or system where the optical properties change on exposure to light having a predetermined property, most commonly ultraviolet (UV) radiation. Most commonly, an optical lens changes from an optically transparent state to a darkened state upon exposure to UV radiation. When the UV radiation is removed, the lens returns to a clear state.

As used herein, the term "electrochromic" is where optical properties such as optical transmission, absorption, reflectance and/or emittance can be controlled in a reversible manner upon, application of an electrical energy, such as a voltage bias.

As used herein, the term "optical head-mounted display" (OHMD) refers to a wearable device that has the capability of reflecting projected images as well as allowing the user to see through the display, similar to augmented reality technology.

As used herein, the term "augmented reality" (AR) refers an interactive experience of a real-world environment where the objects that reside in the real world are enhanced by computer-generated perceptual information, sometimes across multiple sensory modalities, including visual, auditory, haptic, somatosensory and olfactory. AR can be defined as a system that fulfills three basic features: a combination of real and virtual worlds, real-time interaction, and accurate 3D registration of virtual and real objects.

As used herein, the term "hook-and-loop fastener" which is commonly referred to as "Velcro" refers to two components: typically, two lineal fabric strips (or, alternatively, round "dots" or squares) which are attached (sewn or otherwise adhered) to the opposing surfaces to be fastened. The first component features tiny hooks, the second features smaller loops. When the two are pressed together the hooks catch in the loops and the two pieces fasten or bind temporarily. When separated, by pulling or peeling the two surfaces apart, the strips make a distinctive "ripping" sound.

As used herein, the term "QR (quick response) code" refers to a type of matrix barcode (or two-dimensional barcode) first designed in 1994 for the automotive industry in Japan. A barcode is a machine-readable optical label that contains information about the item to which it is attached. In practice, QR codes often contain data for a locator, identifier, or tracker that points to a website or application. A QR code uses four standardized encoding modes (numeric, alphanumeric, byte/binary, and kanji) to store data efficiently; extensions may also be used. A QR code consists of black squares arranged in a square grid on a white background, which can be read by an imaging device such as a camera and processed using Reed-Solomon error correction until the image can be appropriately interpreted. The required data is then extracted from patterns that are present in both horizontal and vertical components of the image.

As used herein, the term "occupational noise" refers to the amount of acoustic energy received by an employee's auditory system when they are working in the industry. Occupational noise, or industrial noise, is often a term used in occupational safety and health, as sustained exposure can cause permanent hearing damage. Occupational noise is considered an occupational hazard traditionally linked to loud industries such as ship-building, mining, railroad work, welding, and construction, but can be present in any workplace where hazardous noise is present.

As used herein, the term "night vision device" which is also known as "night vision goggles", refers to an optoelectronic device that allows images to be produced in levels of light approaching total darkness. The image may be a conversion to visible light of both visible light and near-infrared, while by convention detection of thermal infrared is denoted thermal imaging.

Exemplary Embodiments

The present disclosure relates personal air filtration device systems, such as HCDs, and other mouth and nose-covering devices to provide a controlled and comfortable environment to a user. Users may need a controlled environment due to various health-related reasons such as to protect those with respiratory ailments, compromised immune systems, advanced age, from airborne contagion. The same protection may also be needed for the protection of health care providers. Alternatively, such devices may be desirable to use in harsh environments, such as extreme cold or heat, or environments with high levels of suspended particulate, such as dust. Still further, such devices may also be desirable to protect the user from harsh noise environments. The present disclosure illustrates embodiments of HCDs and masks that include filtering fabric and an air mover.

In various exemplary embodiments, the HCD includes an air intake filter fabric component (FFC) designed to provide clean air to a user. Fabric located in the neck and head area may act as an air intake filter. Exhaled air from a user may be exhausted through an exhaust port. An air mover pulls the air from inside the HCD and exhausts it to the environment. The exhaust air is filtered in instances where the user is infected with a disease but wishes to go out in public.

In various exemplary embodiments, an HCD includes a fabric component where a portion of the fabric is permeable to air and a portion that is impermeable to air. An air mover can pull air from inside the HCD and exhausts it to the environment, pull air from outside the HCD to inside the HCD and exhaust it to the environment, or maintain a neutral air flow as desired by a user. The air passes through an inlet port to enter the HCD and an outlet port to exit the HCD that is spanned by a filter cartridge assembly comprising an air filter.

In various exemplary embodiments, an app running on a user's smart device may be configured to wirelessly connect with a personal air filtration system to control and monitor operation of the system. Environmental data inside and outside of the system and biometric data of the user may be collected by one or more sensors and be monitored on the app. The app may provide audible or visual alerts to a user according to pre-determined parameters or thresholds that may be reached in the environmental or biometric data collected.

Head Covering Device (HCD) with Filtering Fabric

The following embodiments relate to a HCD with filtered air and capable of negative, positive, or neutral air flow mode to provide a comfortable and controlled environment for a user. The HCD comprises a fabric component that can filter coming into or out of the device.

The term "negative air flow" is used to indicate that, in accordance with embodiments of the invention, air is actively exhausted from inside the HCD by the air mover. The negative flow" thus created by the active exhaust serves to draw air into the HCD through the FFC. As a result of this design, the intake air can be drawn into the device from a large surface. Consequently, the intake air can be a gentler stream of air, as compared to the stream of air if an air mover were pushing the intake air into the device. This gentler stream is believed to improve the comfort of the preferred embodiments of the invention.

The HCD may also be capable of "positive air flow" wherein air is actively drawn into the device through an inlet filter by an air mover and exhausted through the FFC. The HCD may also be capable of "neutral air flow" wherein air is drawn into and out of the device through the breathing of the user.

FIG. 1 is a front view of a user 104 wearing a head covering device (HCD) 102, according to an embodiment of the disclosure. An HCD 102 is placed over the head of a user 104. HCD 102 comprises a frame 106 and a transparent face shield 108. Frame 106 may be constructed from a rigid or semi-rigid material. Frame 106 is a hoop-like structure wherein the perimeter of the frame has a generally oval shape but may also be generally circular or some other appropriate shape, such as pear-shaped. Frame 106 comprises a channel 110. The edge of the face shield 108 may be placed in and sit in the channel 110.

Frame 106 may be constructed from a polymer or metal or a combination thereof. The polymer may comprise fiberglass, carbon fiber, graphene, polyamide, polycarbonate (PC), polyester, high density or low density polyethylene, polyethylene terephthalate (PET), polypropylene (PP), polystyrene (PS), polyurethane, polyvinyl chloride (PVC), polyvinylidene chloride, acrylonitrile butadiene styrene (ABS), polymethylmethacrylate (PMMA), polytetrafluoroethylene (PTFE), phenolic, polyetheretherketone (PEEK), maleimide, bismaleimide, polyetherimide, polyimide, plastarch, furan, silicone, polysulfone, rubber, or a combination thereof. The frame may have a generally oval shape and circles a user's head, with a lower half passing below the user's chin and an upper half passing above a user's forehead.

In a preferred embodiment, face shield 108 is shaped as a hemi-ellipsoid. The shield comprises a transparent polymer or glass. The polymer may comprise an acrylic such as polymethylmethacrylate. The polymer may comprise polystyrene (PS), polycarbonate, glycol modified polyethylene terephthalate (PETG), or cellulose acetate butyrate or a combination thereof. In some embodiments, the face shield is made from a laminate of polymeric films, each contributing to the structural or optical properties of the face shield. As an example, one layer of the laminate may be included to provide shatter resistance.

The face shield is preferably set close enough to the face of a user where the user's eyes are unable to focus on the inner surface of the face shield, and thus not interfere with the vision of the user. In some embodiments, the inner surface of the face shield is not set close enough where the eyes are unable to focus on the inner surface of the face shield. Face shield 108 may be permanently attached to the frame 106 or may be detachable from the frame. If permanently attached, this may be accomplished by using an adhesive, thermal welding, or some other means. If detachable, the face shield may be held securely to the frame using an attaching device, such as a hook and loop fastener (Velcro®), clamps, clasps, magnets, screws, or other means.

The face shield may have a thickness in the range of about 0.05-0.25 inches. In the depicted embodiment, the face shield 108 has a thickness of about 0.125 inches. The face shield may be constructed from materials that are approved for impact resistance by the American National Standards Institute (ANSI). The face shield may be double-walled, preferably with a vacuum therebetween, for extra insulation. The face shield may comprise a scratch resistant coating or layer on the inner and/or outer surface. The face shield may comprise an anti-fogging coating on the inner or outer surface. A replaceable protective layer may be placed over the outer surface of the face shield. Naturally, the replaceable protective layer should comprise a transparent polymer.

A top portion of the transparent face shield may extend above a user's eyes, a bottom portion extends below the user's mouth and a first and second side portion extend beyond the user's side peripheral vision. The top portion of face shield may extend above a user's forehead and the bottom portion extends below the user's chin.

FIG. 1 also illustrates a view of a filtering fabric component (FFC) 112. The FFC 112 may also be referred to as a neck skirt, neck seal, neck collar, or neck shroud. FFC 112 preferably fits snugly around the neck 112 of a user 104, such that particulates do not able to pass between the FFC and the neck of the user. FFC may be flexible or stretchable and may be made of a polymer such as polyester, polypropylene, polytetrafluorethylne (PTFE), polyether ether ketone (PEEK), polyethene-co-chlorotrifluoroethene (E-CTFE), silicone, rayon, spandex, lycra, viscose, or nylon. FFC may be made of a natural fabric such as cotton or wool. FFC may be a composite of a natural fabric and a polymer. FFC may comprise a pharmaceutical grade textile.

Preferably, the FFC filters the replacement air entering the HCD 102 so that the filtering blocks at least 95% of particles 0.3 microns or larger (N95) or at least 99% of particles 0.3 microns or larger (N99) or at least 99.97% of particles 0.3 microns or larger (N100). While N95 may be most comfortable for a mask wearer, who is required to draw fresh air in and expel air out by normal breathing activity; higher levels of filtration may be obtained by the inventive devices because the exhaust and the drawing fresh air in are aided by the fan(s).

As depicted, the FFC 112 is comprised of a single piece or sheet of filtering fabric. The single sheet of filtering fabric, together with the transparent face shield and the frame, cover a user's entire head and a lower portion of the single sheet of filtering fabric encircles the user's neck and forms a seal therewith. FFC may comprise a drawstring to tighten around the neck of a user for better sealing properties. The single sheet of filtering fabric may possess enough stretch to allow the device to be placed over the user's head while leaving the lower portion of the single sheet of filtering fabric intact and still capable of forming a seal around the user's neck.

Alternatively, the lower portion of the single sheet of filtering fabric may comprise a slit to allow the device to be placed over the user's head. In this embodiment, the lower portion further comprises a closure to close the slit and form the seal around the user's neck. That closure may be effected by a hook and loop Fastener®, a zipper, snaps, buttons or any other means of closing the slit. When the zipper is unzipped, allows the device to be fit over the user's head, and when zipped facilitates the fabric component forming a seal around the user's neck.

In some embodiments, the FFC may comprise two types of fabric, whereby only a portion of the fabric allows air to pass through. In other embodiments, the fabric is the same, but some of the fabric is coated to make it impermeable to air. In this way, air flow through some of the FFC, but through not all of it. In yet other embodiments, the fabric may be impermeable to air flow and filter sections are incorporated into the FFC. In these embodiments, less than 50% of the FFC allows air to pass through while the remaining balance of the FFC is impermeable to air flow. In other embodiments, less than 50% of the FFC 112 is impermeable to air flow while the remaining balance of the FFC allows air to pass through.

In yet other embodiments, the FFC is equipped with filtering components that are held in place by the fabric part of the FFC. Such filtering components are preferably made of a porous filter medium. Alternatively, the filtering components use or are combined with other air filtering methods, such as electrostatic filtering or water filtering.

In some embodiments, the length of the FFC may be extended in some instances to cover the area for those users who have a tracheotomy or have a tracheotomy tube. The fabric may have a port to allow for a tracheotomy tube to pass through. The port may have an elastomeric ring to form a seal around the tube.

In some embodiments, the FFC may extend to the base of the neck and rest on the shoulders of the user. The FFC may be a stiff fabric to help provide support for the user. In other embodiments, shoulder supports may extend from the frame of the HCD to the shoulders.

In some embodiments, the FFC may comprise a frontal fabric seal located in front of the neck region of the user below the bottom of the frame. Such a frontal fabric may be designed to be impermeable to an air flow. This provides additional protection of a user, such as a health care working with a person, such as a patient, who is coughing or sneezing.

In other embodiments, a separate frontal fabric may be attached to the FFC near the bottom of the frame in front of the neck region of the user. The bottom of the frontal fabric may or may not be attached to the bottom of the FFC. The frontal fabric may act like an apron, i.e. blocking particles exhaled by someone directly in front of the user. This embodiment may be particularly useful for healthcare workers, attending to patients who are coughing or sneezing. Such an apron may be convenient to take off and clean. Alternatively, the apron may be disposable, such as a paper-based tissue.

In some embodiments, the FFC may comprise a small foam block or insert that a user can use to scratch their noses without having to remove the HCD. The foam block or insert may be mounted on the face shield or on the frame. In other embodiments, the FFC comprises finger sockets that protrude into the facial area of the HCD 102. Finger sockets allow a user to insert their fingers without compromising the environment inside the HCD but yet allow the user to scratch or rub an itch. The FFC may be baggy and stretchable enough for a user to scratch their nose or dab their face without breaking the seal around the user's neck.

In some embodiments, the FFC may comprise two or more layers of fabric and wherein an ultra-violet (UV) light emitting diode (LED) may be placed between the two or more layers of fabric. The UV-LED is to disinfect the air that enters the device. In a preferred embodiment, the UV LED is a UV-C emitting LED that emits light with a wavelength in the range of about 200-280 nm.

In yet other embodiments, the HCD may be equipped with at least one UV source that is directed at the inside of the FFC, so as to disinfect the inside surface of the FFC and the air that passes through it before being inhaled by the user.

Figure 5:
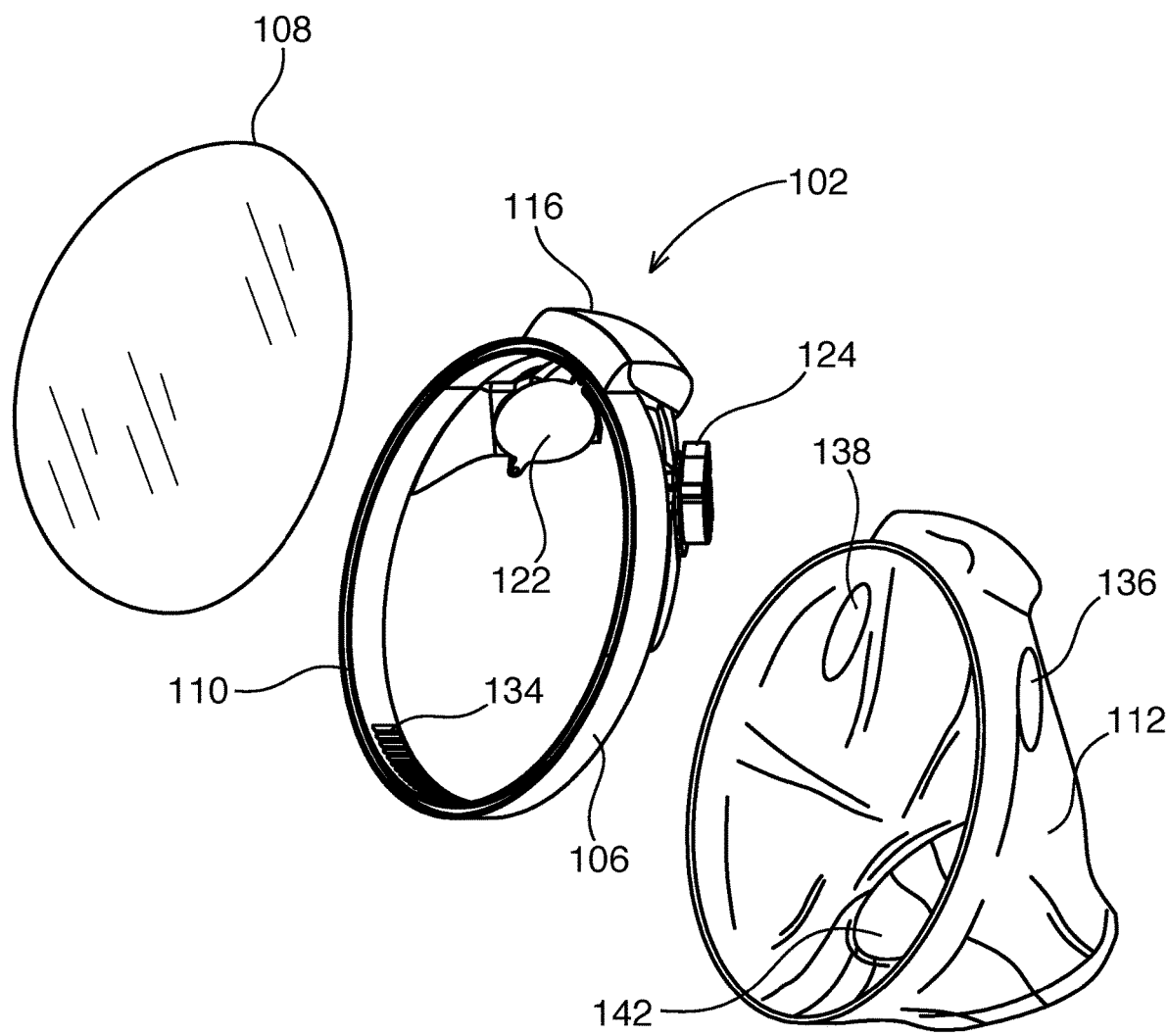
FIG. 5 illustrates an exploded view of an HCD, according to an embodiment of the disclosure.

Referring to the embodiment depicted in FIG. 5, FFC 112 also attaches to the frame 106 to form a seal. The FFC 112 may be stretched over the frame 106 and channel 110 and held in place by inserting of the face shield 108 in the channel 110 to pinch the FFC 112 in place. Alternatively, the transparent face shield may be attached to one side of the frame 108 and the FFC is attached to another side of the frame, such as in a channel parallel to the channel the face shield is attached in.

Further illustrated in FIG. 1 is a view of a compartment 116. Compartment 116 may be used for storage.

Also shown in HCD in FIG. 1 are earpieces 118 to reduce noise, and dampen sound, and reverberations inside of the HCD 102. This may be necessary when the user 104 speaks or from an audio device inside the HCD. The earpieces or noise reduction devices 118 are preferably placed in front of each ear of the user. Testing has shown that using such noise reduction devices prevents undesirable audio properties, i.e. where the user's voice sounds to the user like he is in a bubble. The noise dampening device may comprise sound blocking panels situated between each ear of the user and the mouth of the user.

The earpieces or noise reduction devices 118 are mounted to the face shield 108 but may also be mounted elsewhere such as on the frame or FFC. The noise absorbing devices may be made of a noise and vibration absorbing material such as a polymeric foam, rubber, or cloth. The noise reduction devices may be permanently adhered to the face shield or frame or may be adhered using a hook and loop fastener or other detachable mechanism. The noise reduction devices 118 may be removable, replaceable, and washable.

The earpieces may also serve the purpose of keeping the HCD centered laterally on the user's head. In other words, the earpieces may provide soft buffers between the user's head and the inside surfaces of the HCD. In some embodiments, it is preferred to provide multiple sizes of earpieces, which can be removably attached inside the HCD, in order to accommodate different sizes of users' heads.

Figure 2:
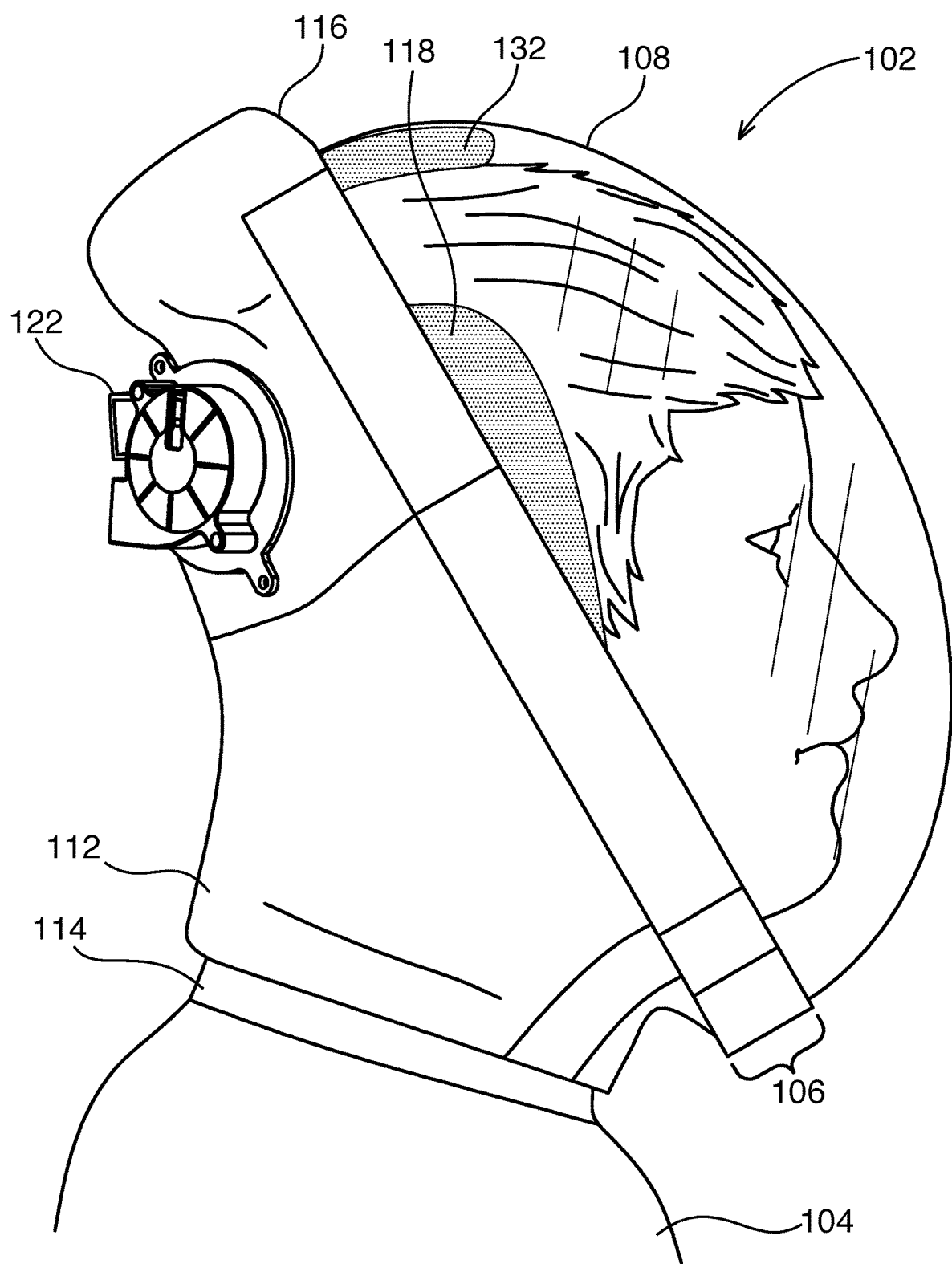
FIG. 2 is a side view of a user wearing an HCD, according to an embodiment of the disclosure.

FIG. 2 is a side view of a user 104 wearing an HCD 102, according to an embodiment of the disclosure. FIG. 2 further illustrates another view of FFC 112. FFC seals around the frame 106 and around the neck area 114 of a user 104. The HCD 102 rests on top of the head of the user. A resting pad 132 is placed at the top of face shield 108 that provides support and cushion between the HCD 102 and the head of the user. The resting pad may comprise a cushion-like material such as cloth, foam, rubber, or other soft material and may be replaceable and washable. As with the earpieces, it may be preferred to provide multiple sizes and/or shapes of removable resting pads, so that the user can select the most comfortable one for his size and shape of head.

FIG. 2 further illustrates an air mover 122 to move air from inside to outside the HCD 102. The air exhausted from inside the HCD is replaced by air outside the device. In this depicted embodiment, the air mover 122 is a fan. The battery pack to supply power for the fan is stored in compartment 116. The fan may be an axial or radial centrifugal fan. The HCD may comprise one or more additional fans. The fan is preferably attached to the housing with a resilient mount, such as foam, cloth, silicone, or a combination thereof, to reduce noise and vibration. The battery pack preferably comprises rechargeable batteries. The batteries may be charged by a cord connected to a wall outlet or by a solar cell. Preferably, a solar cell is mounted to the HCD. The solar cell may provide about 2-6 W of power. In a preferred embodiment, the solar cell may be about 6×6 in$^2$ and provide about 5W of power to recharge the battery and thus power the components of the HCD.

FIG. 2 also illustrates the hemi-ellipsoid shape of the face shield 108. The hemi-ellipsoid shape allows for more uniform air flow around the face of the user in the HCD 102. The face shield may have a longitudinal length in the range of about 10-15 inches, a width in the range of about 8-11 inches and a height in the range of about 3-6 inches. In an exemplary embodiment, the face shield has a longitudinal length of about 13 inches, a width of about 9 inches and a height of about 4.5 inches. The face shield may be detachable from the frame or may be of unitary construction with the frame. The face shield may form an airtight seal with the frame. A polymer gasket, such as a rubber gasket or an O-ring may be located in between the face shield and frame in channel. The face shield may be double-walled for extra insulation. A vacuum may be located between the double walls.

Figure 3:
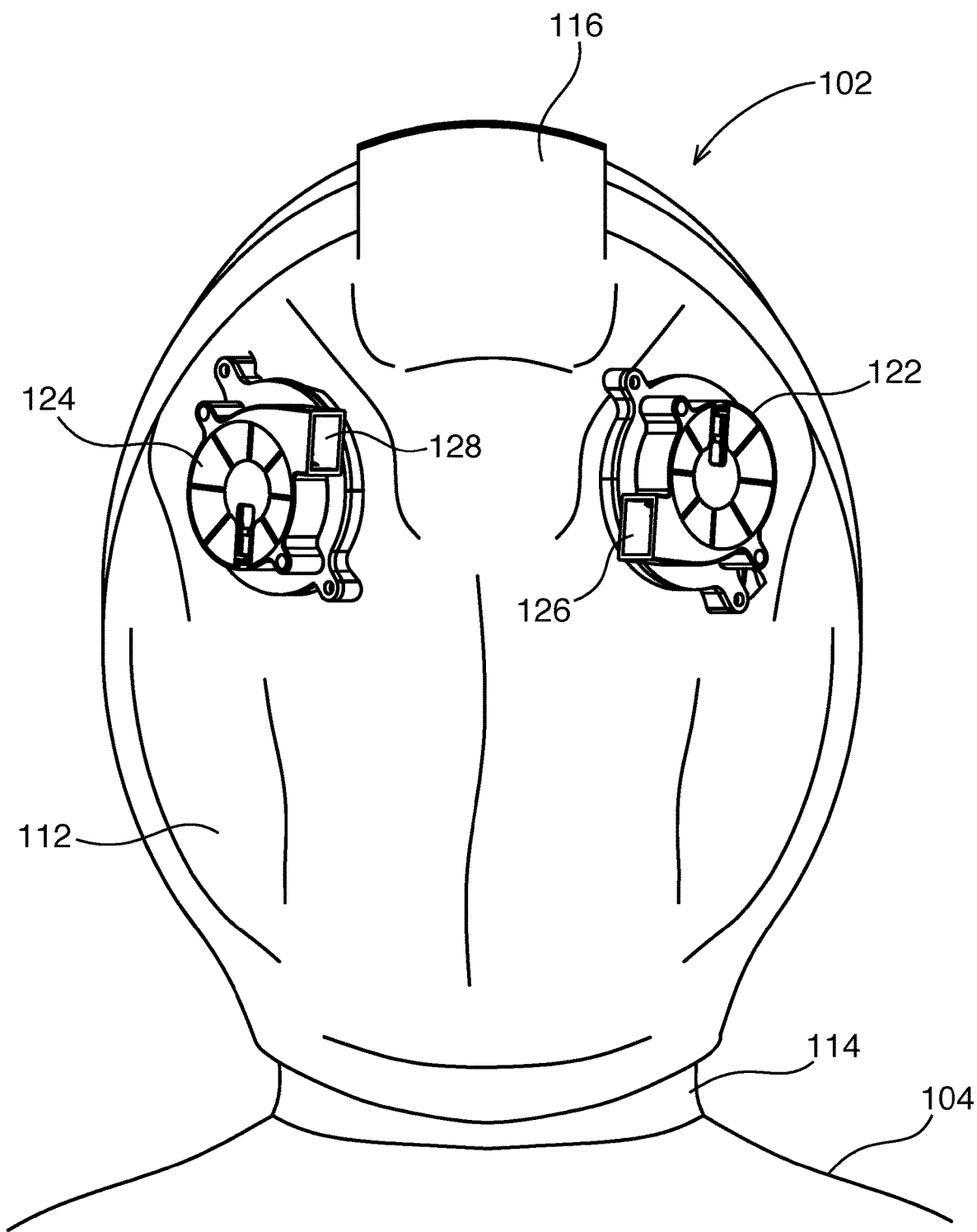
FIG. 3 is a rear view of a user wearing an HCD, according to an embodiment of the disclosure.

FIG. 3 is a rear view of a user 104 wearing an HCD 102, according to an embodiment of the disclosure. FIG. 3 further illustrates how FFC 112 drapes down to the bottom of the neck and forms a seal therearound, although other lengths and designs are possible. For example, the FFC may extend to and rest on the shoulders of the user. In other embodiments, the FFC may extend down the back of the user below the shoulders.

FIG. 3 further shows a second fan unit 124. Both fan units are mounted into the frame 106. The FFC 112 comprises openings wherein the fans 122, 124 pass through when placing the FFC on the frame. In other embodiments, the fans may only be attached to the FFC.

FIG. 3 further illustrates the air exhaust port 126 of the first fan 122 and the air exhaust port 128 of the second fan 124. The exhaust ports exit air to the environment. The fans may be operated in parallel or series mode. The fans 122, 124 are arranged on each side of the FFC in FIG. 3 but may be arranged in other ways. For example, one fan may be placed at the top of the FFC while a second fan may be arranged directly below the first fan such as near the base of the FFC. In a preferred embodiment, the fans are arranged in a manner such that it provides balanced weight to the HCD 102.

The one or more fans may be powered by a battery, such as a rechargeable lithium ion battery, nickel cadmium battery, or a nickel metal hydride battery. The batteries may be located near the top of the rigid frame. The fans may be powered by a solar cell and where the solar cell may be mounted in the HCD. The fans may be removable to replace the batteries or if the fan is damaged, breaks down, loses efficiency, etc. The fans may be dual speed or other variable speed fans. The speed may be controlled by the user of the HCD. The fans may be capable of delivering more than about 1 cfm of air. The fans may be capable of delivering about 1-10 cfm of air. The fans may run intermittently with feedback to deliver a desired amount of air to the user and to keep the air fresh inside the HCD. The HCD may comprise an air flow sensor or an air pressure sensor to monitor air flow and pressure within the HCD.

Figure 4:
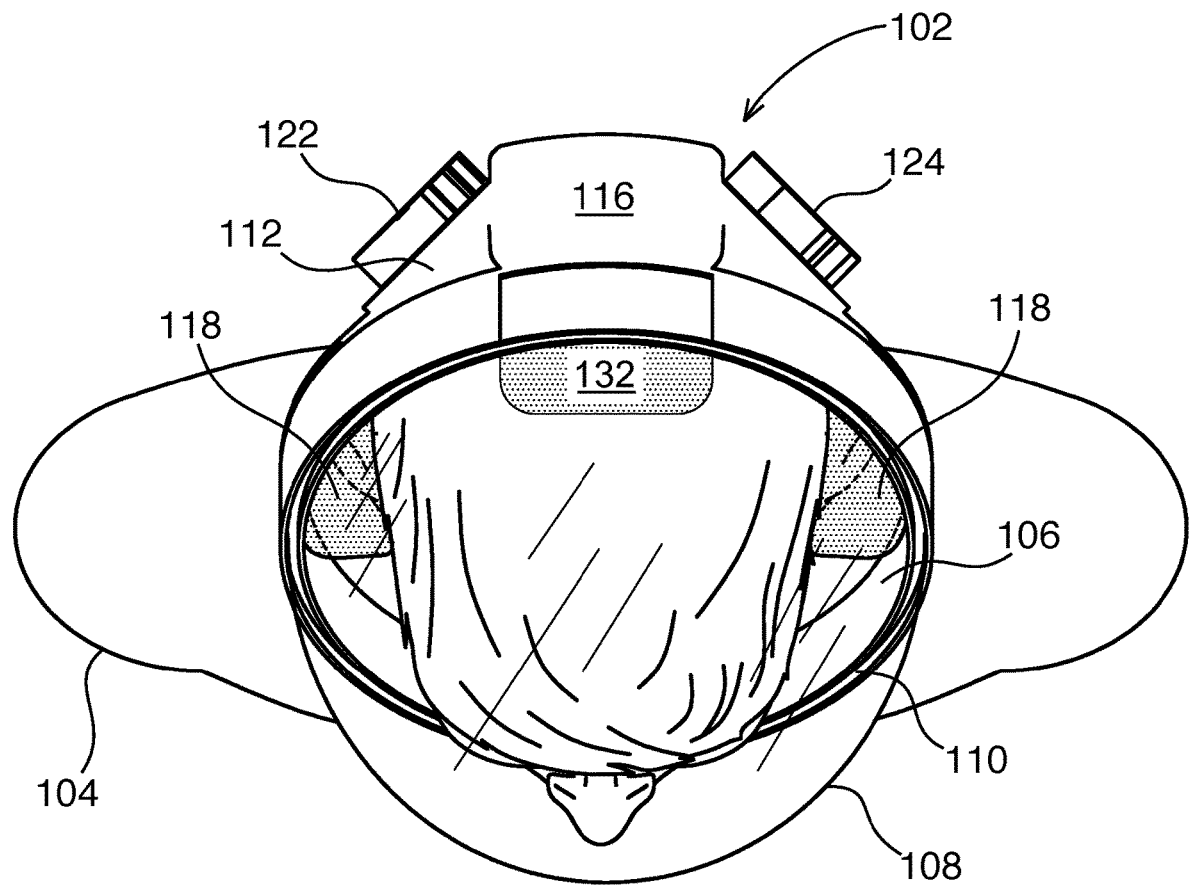
FIG. 4 is an overhead view of a user 104 wearing an HCD 102, according to an embodiment of the disclosure.

FIG. 4 is an overhead view of a user 104 wearing an HCD 102, according to an embodiment of the disclosure. FIG. 4 further illustrates how the HCD is arranged on the head of a user with the resting pad 132. FIG. 4 further illustrates how the frame 106 comprises a channel 110. The face shield 108 sits in the channel. In some embodiments, the FFC may also be stretched over the same channel as the face shield, followed by inserting the face shield on top of the FFC and into the channel to assemble the HCD. An attaching mechanism may then be used to secure the parts of the HCD together. The attaching mechanism may be clips, screws, hook and loop fasteners, magnets, or another device.

In other embodiments, the face shield fits into one channel and the FFC fits into a second channel on the other side of the frame. The face shield can be held in its channel by similar means to those described above. The FFC can be held in its channel by any of those same means.

FIG. 5 is an exploded view of an HCD 102, according to an embodiment of the disclosure. FIG. 5 further illustrates the three primary components of the HCD. FIG. 5 shows further how the fans 122, 124 are mounted to the frame 106 along with compartment 116 which contains the battery pack to provide power to the fans. The compartment is covered by the FFC 112 and can be accessed when the FFC is removed from the frame. In other embodiments, the FFC may comprise an opening to access the compartment when the HCD is assembled. The opening may be a flap that can be opened and shut. The flap may be closed and secured with a zipper, hook and loop fastener, or other means.

Preferably, the frame 106 comprises two exhaust channels, one on each side of the frame. Air is drawn into each exhaust channel, through air intake 134, by the negative pressure created by the fan and then out the exhaust port. Intake 134 is located at the bottom of the frame near the mouth area of a user. The intake may be a single opening (such as a slit) or a plurality of openings aligned in parallel as illustrated in FIG. 5. Intakes may be any shape or size that allows the proper air flow. Through the exhaust channels, the intakes 134 are in fluidic communication with fans 122, 124 and exhaust ports 126, 128 (see FIG. 3).

In some embodiments, such as where the fans are located within the exhaust channels, the ends of the exhaust channels form the exhaust ports. In other embodiments, such as where the fans are outside the exhaust channels, the air exits the exhaust channels and is drawn through the fans and then out a separate exhaust port.

The exploded view of FIG. 5 further illustrates the FFC 112. The FFC comprises openings 136 and 138 for fans 124 and 122 to pass through, respectively. The FFC further comprises an opening 142 to place over the head of a user 104. In some embodiments, the FFC may only comprise an opening for a single air moving device. In other embodiments, the FFC may comprise openings for more than two air moving devices. The openings in the FFC may be lined with a stretchable, resilient material, such as an elastic polyurethane film to create a seal around one or more air moving devices.

Figure 6A:
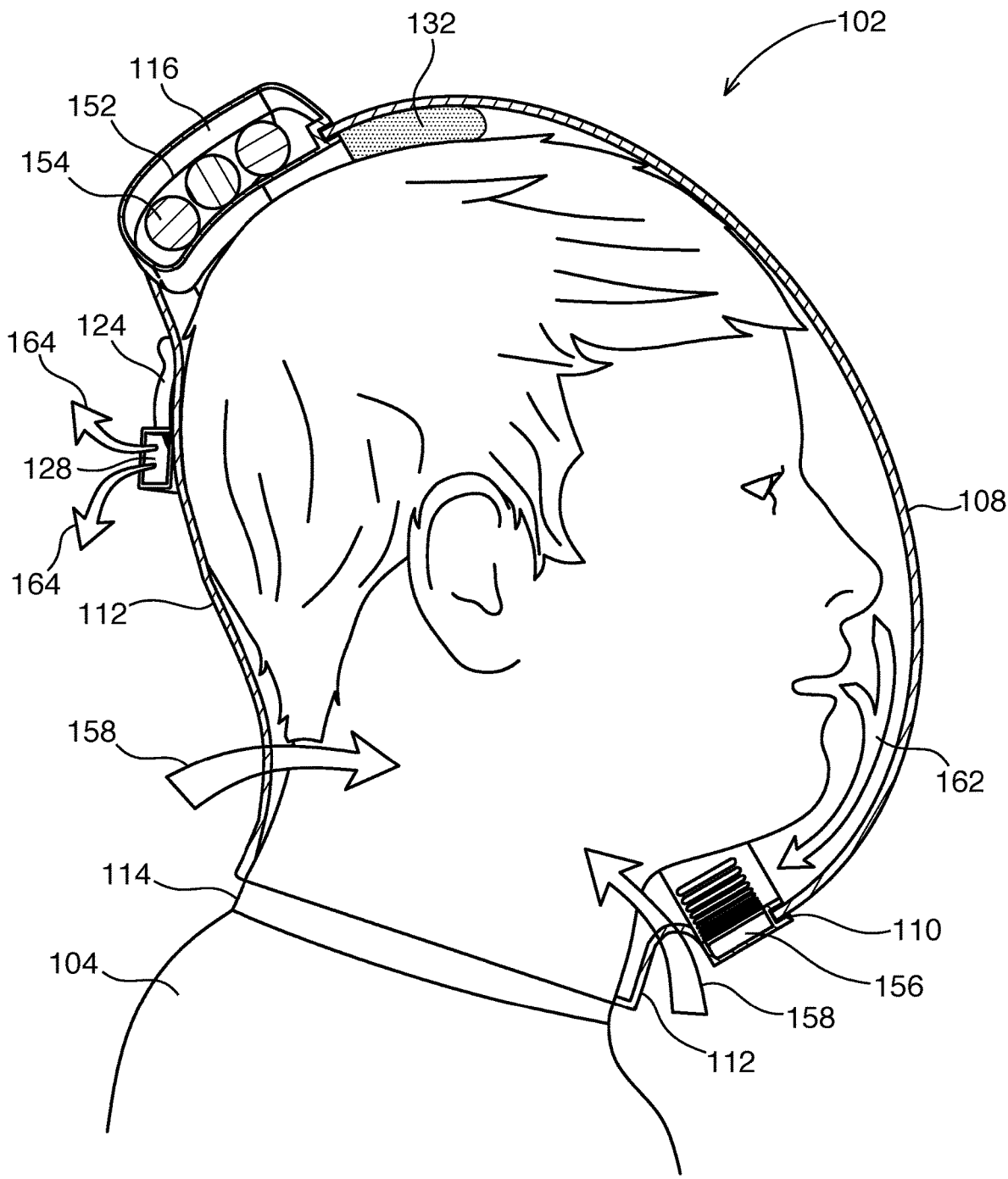
FIG. 6A illustrates a cross-sectional view of an HCD with the head of a user in it and negative air flow, according to an embodiment of the disclosure.

FIG. 6A illustrates a cross-sectional view of an HCD with the head of a user in it and negative air flow, according to an embodiment of the disclosure. FIG. 6 illustrates a battery pack 152 located in compartment 116 further comprising one or more batteries 154. The batteries may be rechargeable and can be recharged by connection to a power outlet or a solar cell. In other embodiments, the batteries may be located in the frame 106.

At the bottom of the frame near the mouth area of the user 104 is seen a cross-section of the exhaust channel 156 that runs from the bottom of the frame towards the fans 122, 124. Air enters the exhaust channel through the intake 134. The fans pull the air through the exhaust channels and pulls the air up through the exhaust port 128.

The negative air flow in the HCD 102 is illustrated in FIG. 6A as follows. Air from the environment outside of the HCD may pass through the fabric of the FFC 112 as intake air 158. Intake air 158 may be also drawn in by the inhale of a user 104 or by the fans 122, 124. When a user exhales from the nose or mouth, the exhale air 162 may then be pulled and drawn into the exhaust channel intake 134 near the mouth of the user by the fans pulling a negative air flow. As air enters intakes 134, the air enters air exhaust channel 156 in the frame. The air then flows from the bottom of the frame towards the top of the frame through the exhaust channel where the fans are located. The exhaust air 164 is then exhausted into the environment out air exhaust ports 126, 128. Thus, the environment, the FFC, the user, intake 134, air flow channel 156, fans 122, 124 and air exhaust ports 126, 128 are in fluidic communication. The air flow process may quickly replace the air in the HCD with outside air from the environment that is filtered through the FFC, to thereby provide a consistent, comfortable, and safe environment for the user.

Figure 6B:
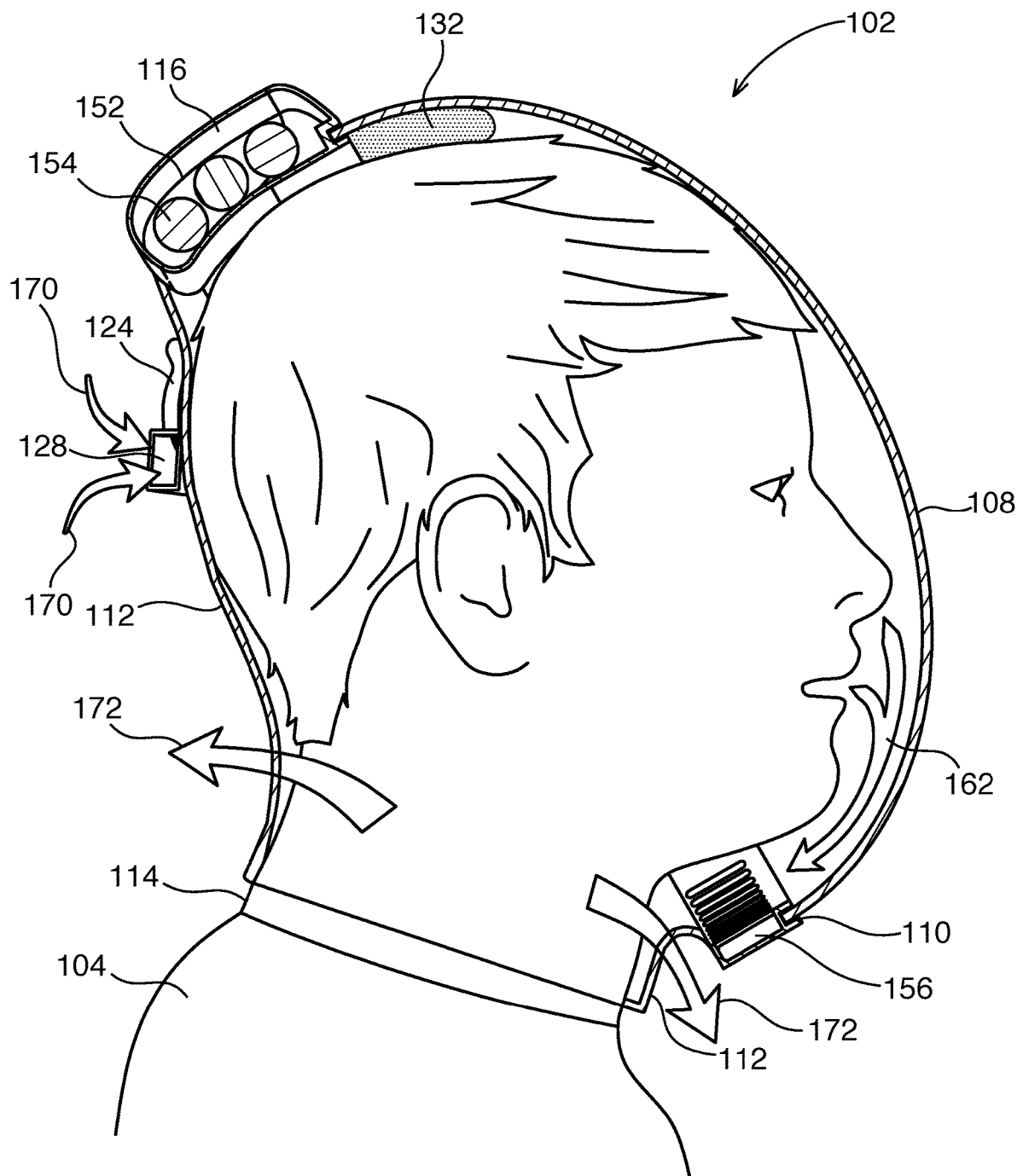
FIG. 6B illustrates a cross-sectional view of an HCD with the head of a user in it and positive air flow, according to an embodiment of the disclosure.

FIG. 6B illustrates a cross-sectional view of an HCD with the head of a user in it and positive air flow, according to an embodiment of the disclosure. The HCD can also operate in a positive air flow mode. The positive air flow in HCD 102 is illustrated as follows. Air 170 is pulled into the HCD by fans 122, 124. Air inside the HCD is replaced by this air and is pushed out of the device as exhaust air 172 through the filtering fabric 112. Exhale air 162 can also be exhausted through the filtering fabric. A filter may be placed over the intake of the fans to filter the incoming air.

In some instance, HCD 102 may also operate in neutral mode. Neutral mode is where the air is balanced by the fans such that air moving in and out of the HCD is controlled by the breathing of the user. In some embodiments, one fan is pushing air into the HCD while the other fan is pulling air out of the HCD.

In some embodiments, such as those depicted in FIGS. 1-6, the air passing out the exhaust ports is filtered by a portion of the FFC that covers the ports. In other embodiments, a separate air exhaust filter may be placed over the air exhaust ports. In either event, this prevents contagion from the user, for example if the user is sick with a respiratory illness, being exhausted into his immediate environment. In other words, this should reduce the amount of microorganisms such as viral, fungal, or bacterial particles that are emitted from the HCD 102. The filter may be made from cotton, foam, paper, or stainless steel. The filter may be a coarse filter, fine filter, semi-HEPA (high efficiency particulate air) filter, HEPA filter, or an ultra-low particulate air (ULPA) filter. The filter may be a combination hydrogen fluoride and hydrogen chloride filter. The filter may be replaceable if clogged, damaged, etc. The filter may be a UV filter or ultrasonic filter to clean and purify the exiting air stream. Alternatively, the filter may be enhanced with electrostatic filtering or water filtering of the air. The air exhaust filter may block at least 95% of particles 0.3 microns or larger (N95) or at least 99.95% of particles 0.3 microns or larger (N99) or at least 99.97% of particles 0.3 microns or larger (N100). As mentioned, in some embodiments, the air exhaust filter may be the portion of the FFC that covers the exhaust ports.

Alternative Frame Design for HCD with Filtering Fabric

The following embodiments describe a different design of the frame than what is previously depicted in FIGS. 1-6 and described above.

Figure 7B:
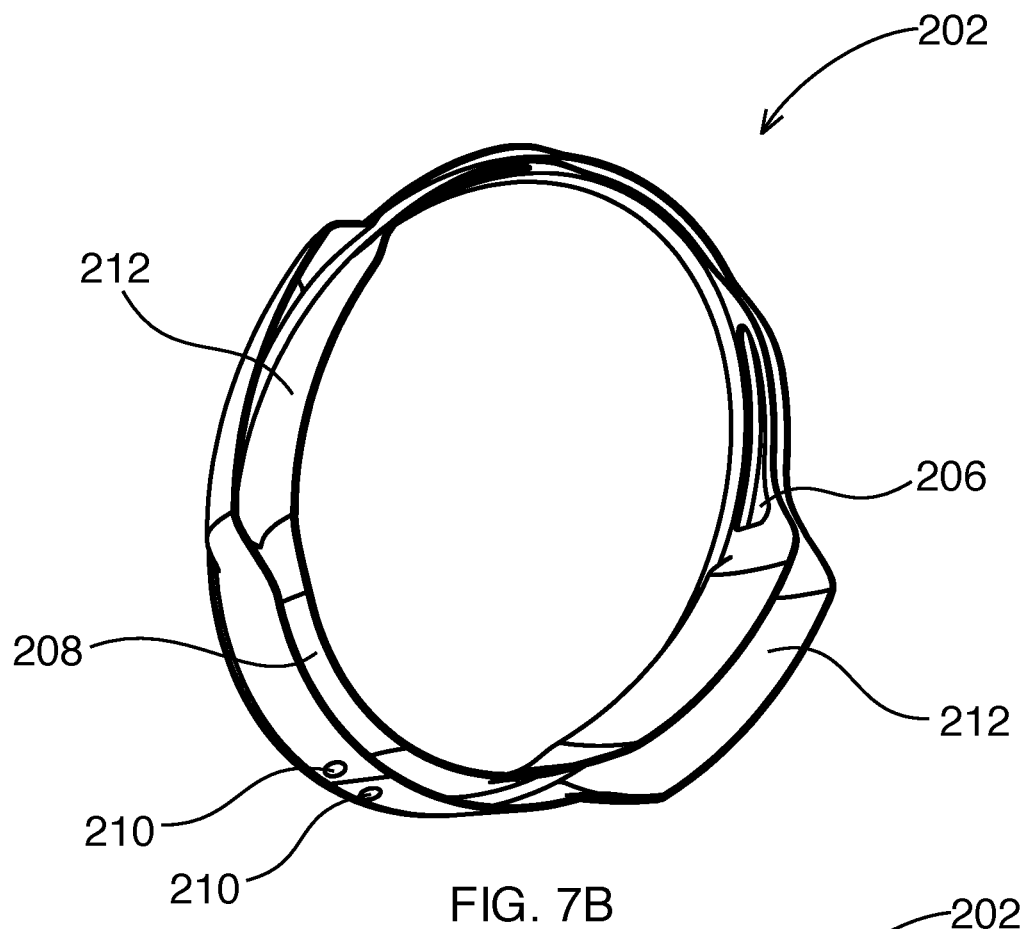
FIG. 7B illustrates a bottom view of a frame comprising compartments for an air moving device and battery for an HCD, according to an embodiment of the disclosure.
Figure 7A:
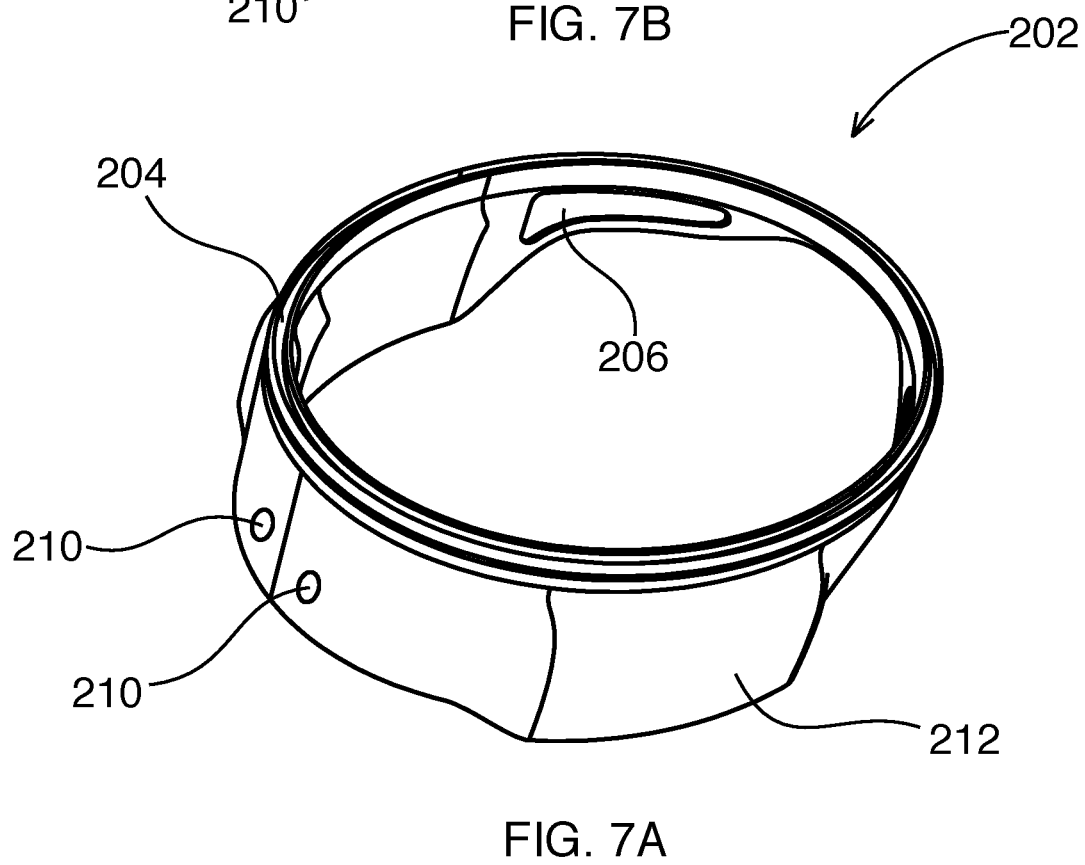
FIG. 7A illustrates a top view of a frame comprising compartments for an air moving device and battery for an HCD, according to an embodiment of the disclosure.

FIG. 7A illustrates a top view of a frame 202 comprising compartments for an air moving device and battery for an HCD, according to an embodiment of the disclosure. FIG. 7B illustrates a bottom view of a frame 202 comprising compartments for an air moving device and battery for an HCD, according to an embodiment of the disclosure. The frame is a hoop-like structure with a generally elliptical shape, but may also be generally circular-like, or some other appropriate shape. The frame comprises a top channel 204 of a constant width along the entire perimeter. The top channel allows for a face shield to be placed and secured to the frame. The top channel may include a gasket or O-ring to aid in securing the frame and to make a seal to a face shield.

Frame 202 further comprises an air intake 206 near the bottom of the frame 206 and near the mouth area of a user. This is similar to intake 134 in frame 106. The frame also comprises a second intake port on the other side of the frame. The frame comprises a second channel 208 on the underside or bottom of the frame. An outer wall and inner wall that are joined at the top but not the bottom forms the channel. The second channel runs along the perimeter and underside of the frame.

Frame 202 further comprises air exhaust ports 210 on the outer wall of the frame. Exhaust ports 210 are located at about the opposite side of the frame from intakes 206. In other embodiments, a partition may be located between the air exhaust ports 210 within channel 208.

The inner width between the inner and outer walls of the second channel 208, varies along the perimeter. The narrowest portion of the frame is in the region between the intake ports 206. The second channel widens along the perimeter towards the exhaust ports 210. The widest portion forms compartments 212. The compartments may also be referred to as "bump outs". In these compartments may be located one or more air moving devices, such as centrifugal fans. The compartments may also contain one or more power sources such as one or more battery packs. The second channel narrows near the air exhaust ports 210.

Figure 8:
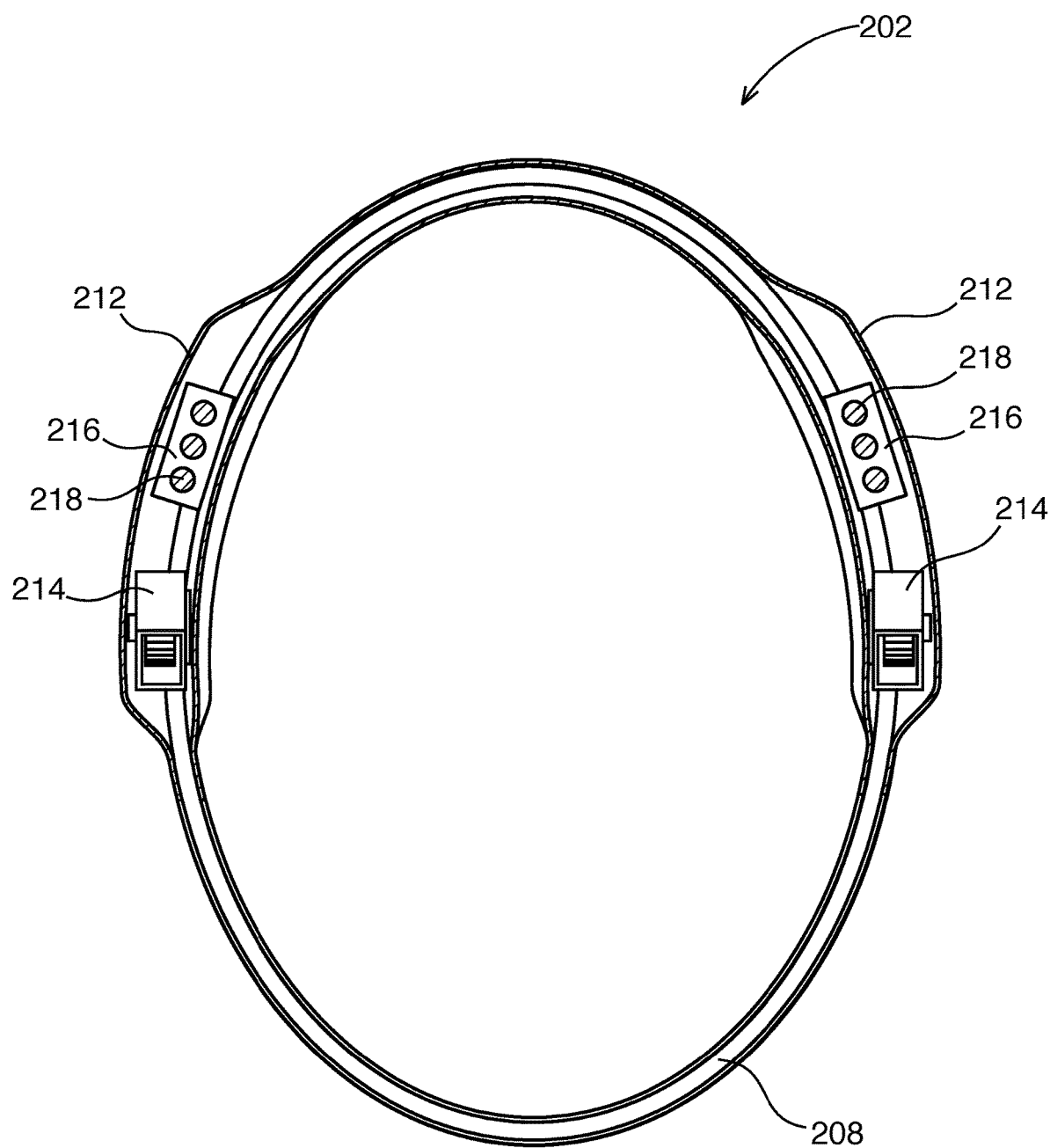
FIG. 8 is a cross-sectional view of a frame comprising an air moving device and battery for an HCD, according to an embodiment of the disclosure.

FIG. 8 is a cross-sectional view of a frame 202 comprising an air moving device and battery for an HCD, according to an embodiment of the disclosure. FIG. 8 illustrates how an air moving device and power source may be arranged in a frame. One or both compartments 212 further comprise a fan 214 to move air. The fan 214 may be a centrifugal fan. The compartments may further comprise a power source such as a battery pack 216 that is in electrical communication with the fan. The battery pack comprises one or more batteries 218. The frame may comprise only one battery pack that may power one or more fans.

Air may flow in frame 202 in an HCD as follows. Air may enter intake ports 206 near the mouth of a user. One or more fans 214 aid in drawing exhaust air into the intake ports. Air then flows through second channel 208 towards the air exhaust ports 210 on the opposite end of the frame from the air intake ports 206. The air may be exhausted into the environment as the air passes through the exhaust ports or through a filter before it is exhausted to the environment.

In some embodiments, there is no frame. The face shield may be directly attached to the FFC. Either the face shield, the FFC, or both may comprise pathways or channels to direct to bring air to the air moving devices and out the exhaust ports.

Environmental Control for a HCD with Filtering Fabric

The following embodiments describe systems and methods to provide a controlled temperature and breathing environment within an HCD by conditioning the air within the HCD with an environmental control component. The environmental control component can control the air flow, temperature, or humidity or a combination thereof within the device.

Figure 9:
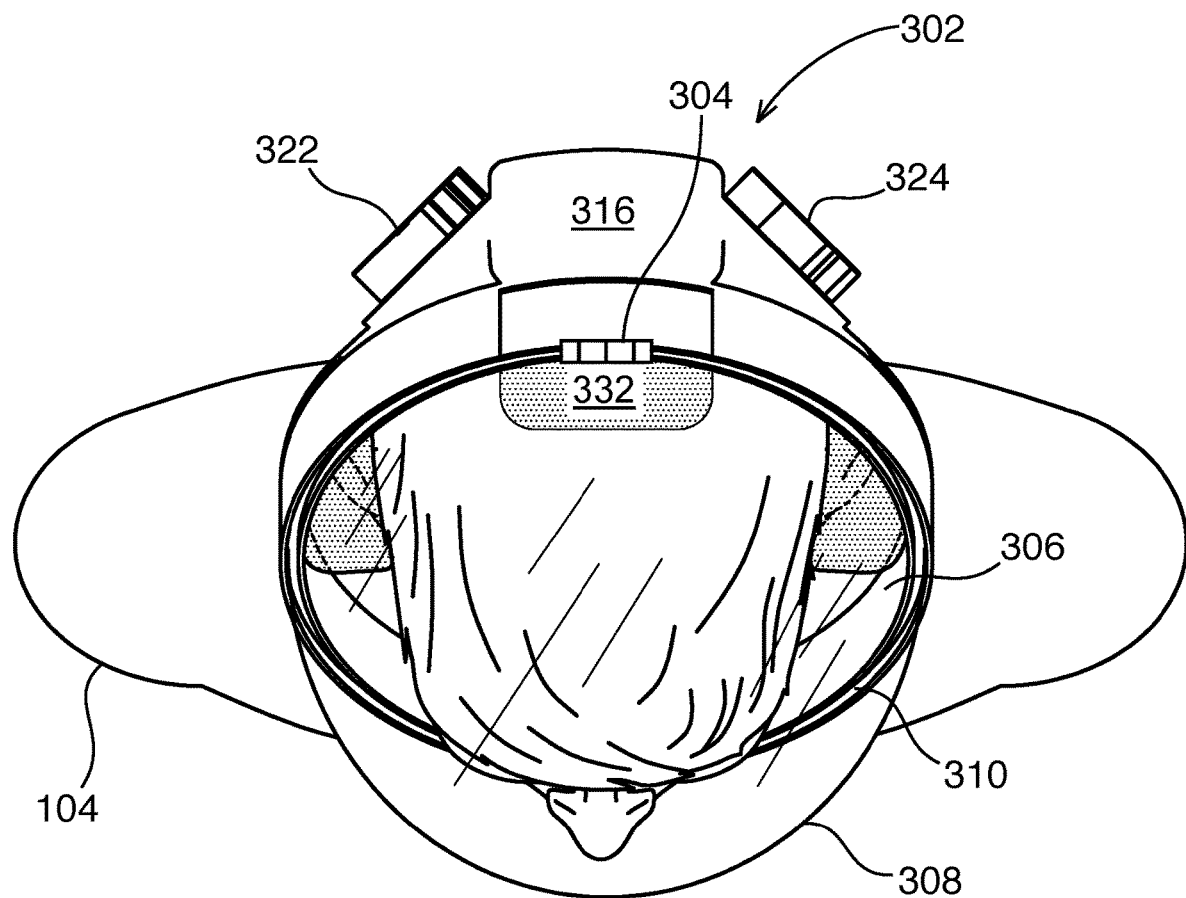
FIG. 9 is a side view of a user wearing an HCD with a pocket, according to an embodiment of the disclosure.

FIG. 9 is a side view of a user wearing an HCD 402 with a pocket 406, according to an embodiment of the disclosure. FIG. 9 illustrates an HCD 402 with a frame 406, face shield 408, fan 422, air exhaust port 426, and a resting pad 432. The HCD further comprises an impermeable neck fabric (INF) 404 that is impermeable to a stream of air. The INF may be composed of a coated fabric, polymer or rubber or an ultra-high thread count fabric. The INF covers a compartment 416.

The INF further comprises one or more pockets 406. An inlet filter 408 may be placed or inserted into the one or more pockets 406 to filter incoming air. The filter may be replaceable. The filter may block at least 95% of particles 0.3 microns or larger. The filter may be a coarse filter, fine filter, semi-HEPA (high efficiency particulate air) filter, HEPA filter, or an ultra-low particulate air (ULPA) filter. The filter may be a combination hydrogen fluoride and hydrogen chloride filter. The filter may be replaceable if clogged, damaged, or require a more or less coarse filter. The filter may provide a particulate-free atmosphere to the user wherein the particles include viruses, bacteria, dust (such as wood or silica dust), pollen, or smoke.

Air flow in HCD 402 occurs as follows. Incoming air 410 from the environment passes through a filter located in pocket 406 wherein particulates are removed. Exhaust air 462 from the user may then be exhausted through an air intake port located in the frame as previously illustrated in FIG. 6. The air is pulled into the intake by the negative pressure created by the fan 422. The air travels through the air exhaust channel towards the fan wherein the air exits the HCD 402 out the air exhaust port 426 as exhausted air 412. Air pressure differences may be detected by one or more sensors.

The HCD described herein further comprises at least one additional air inlet 414. The additional air inlet may comprise a thermoelectric cooler. The thermoelectric cooler may be designed to heat or cool incoming air 416. The thermoelectric cooler may be combined with a heat exchanger device to increase efficiency of heat transfer between incoming and exhaust air. The thermoelectric cooler may be used to control the temperature of the air to prevent fogging on the face shield 408 or humidity build-up in the HCD. The inner surface of the face shield may comprise an anti-fogging layer. The pocket may also contain a thermoelectric cooler. The thermoelectric cooler may operate on the principle of the Peltier effect.

The additional air inlet or other air inlet may comprise an energy recovery or heat recovery device. Such a device would heat incoming intake air with outgoing exhaust air in order to maintain a comfortable environment within an HCD described herein. The pocket may also contain an energy recovery device.

Additional air inlet or other air passage may comprise a sensor that detects one or more harmful or poisonous gases as the gases enter the HCD. The harmful gases may include $CO_2$, CO, NOx, radon, or methanethiol. Pocket may also contain one or more sensors.

The depicted HCD further includes a water reservoir 418. The water reservoir acts as a water source to the neck fabric wherein the water may be wicked by the neck fabric to provide evaporative cooling for the user to provide cooling to the neck area and cool air to breathe.

The HCD described herein may comprise a compartment containing ice that is adjacent an inlet filter. Incoming air is cooled as it passes over the ice. As the ice melts, the water is evaporated as the air passes over which can provide a further mode of cooling.

The HCD described herein may further include a fluid atomizer or mister. The atomizer may use water in the water reservoir to provide a mist of water inside an HCD. An HCD described herein may further include an environmental control device that can be used by a user to control the temperature inside the HCD by raising or lowering the temperature. The environmental control device may further comprise a source of water vapor to increase the humidity of the air inside the device.

The HCD described herein may further include a heater. The heater can heat the air inside an HCD. The heater may be an electric resistive heater. The HCD described herein may further include a chiller to chill the air inside an HCD.

In some embodiments, fabric components described herein may comprise a phase-change material, such as that deployed in high-end sport clothing. The phase-change material, which may be encapsulated in the fabric of the FFC or held in reservoirs elsewhere in the HCD, works by reversibly storing and releasing heat at pre-defined temperature ranges. In the most common example, the phase change material is used to retain heat in a device designed to be used in sub-zero environments. The material, such as a paraffin or lipid, melts when in an environment with a temperature above a certain point. This melting is endothermic, so cools the inside of the device. When the device is in a colder environment, the material solidifies, e.g., crystallizes, which change is exothermic, thus warming the inside of the device.

Another temperature-affecting technology that may be incorporated into the FFC is one that is designed to wick perspiration away from the user. As that perspiration evaporates, the user is cooled thereby. One commercial example of such technology is available from Arctic Cool® in their products sold as HydroFreeze™.

An HCD described herein may further include a multi-speed air moving system. The multi-speed air moving system may be a dual speed fan. If a pre-set environmental threshold or parameter is exceeded within the HCD, such as temperature or humidity, the air moving system increases to a higher speed to improve the environment by increasing air flow within the HCD. The air mover may be adjusted continually to maintain a desired target atmosphere in the device.

An HCD described herein may further include an environmental control device that can be used by a user to control the humidity inside the HCD by raising or lowering the moisture level. The environmental control component captures water vapor to lower humidity of the air inside the device.

An HCD described herein may include one or more sensors to provide filter end of useful life alerts to the user based on at least one of age of the filter, increased head pressure on the filter and optical readings indicating a dirty filter.

In some embodiments, wearable electronics may be embedded in the neck fabrics, frame, air moving device, or face shield to provide environmental monitoring and thermal regulation within the HCDs described herein. The wearable electronics may also monitor the vital signs of a user such as pulse rate, blood pressure, respiration, skin moisture, and body temperature. The electronics may be powered by the power source used for the air moving device or a separate power source may be used. The electronics may include one or more sensors may be included to detect for air leaks around the fabric component sealed around the neck area.

Communication Component for a HCD with Filtering Fabric

The following embodiments include communication component or hardware with the HCD. This communication hardware is used to provide audio and/or video capabilities for the user in an HCD. As such the communication hardware facilitates communication with other people who may or may not be wearing an HCD, as well as news, alerts, weather, entertainment, and other services to the user. The communication hardware may also facilitate communication with a smart device such as a smart phone, tablet, or wearable.

Figure 10:
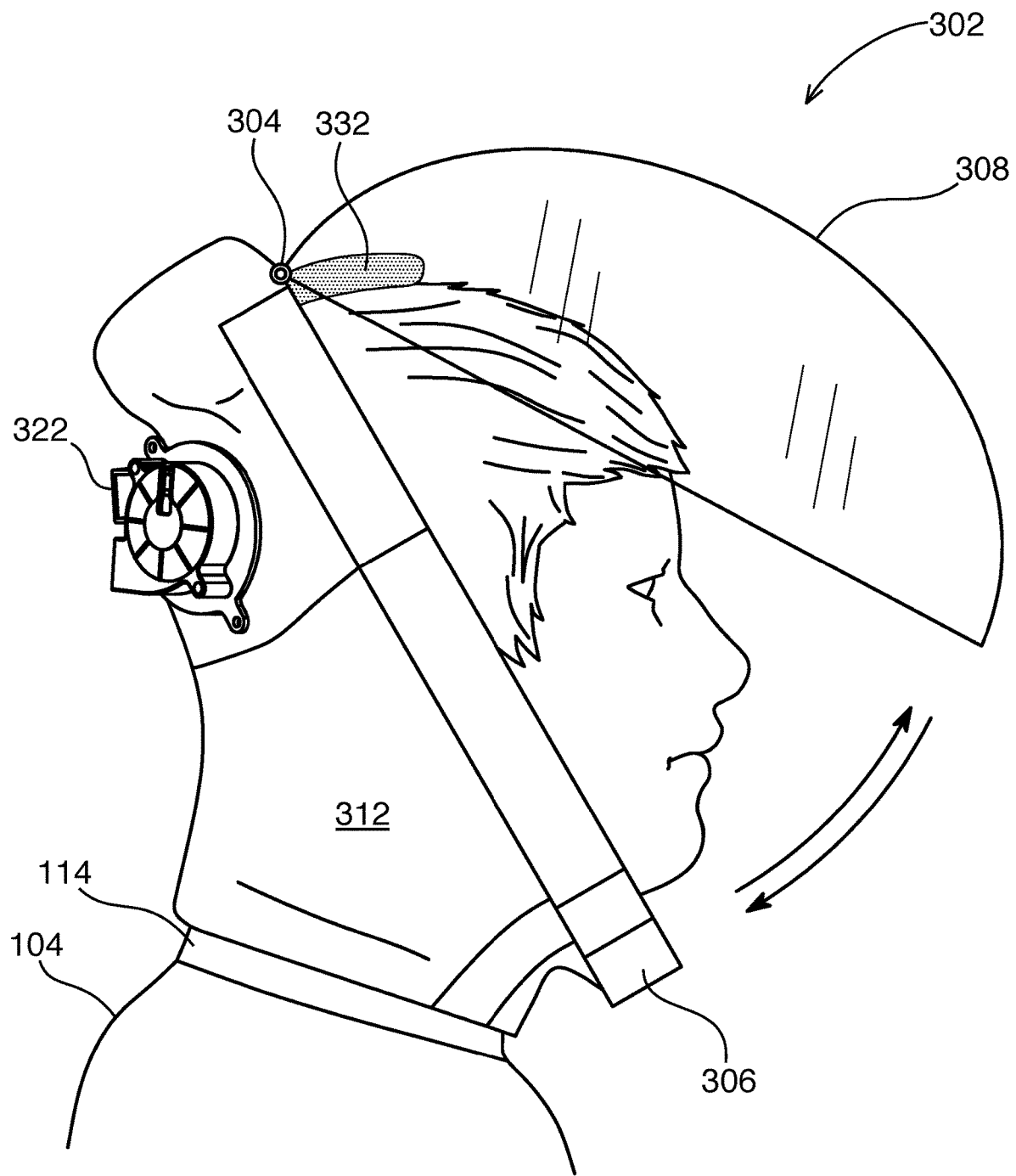
FIG. 10 is a front view of a user wearing an HCD equipped with communication hardware components, according to an embodiment of the disclosure.

FIG. 10 is a front view of a user wearing an HCD 502 equipped with communication hardware components, according to an embodiment of the disclosure. The HCD 502 comprises a noise reduction device 518, compartment 516, channel 510, and FFC 512. The communication hardware may be connected to the internet. The communication hardware may be wirelessly connected to a smart phone. The communication hardware may be controlled by a user with a smart app on a smart device, such as a smart phone. The communication hardware further comprises Bluetooth technology for wireless communication with the smart phone. HCD 502 comprises a speaker 504. The speaker 504 communicates audio and may be an earphone, headphone, ear bud, or an earpiece. Speaker 504 allows a user to better hear sounds coming from outside the HCD or to communicate with another person. The speakers may be used to communicate with someone specifically wearing a similar HCD. Speaker 504 may be mounted on shield 508 or frame 506 near one ear. HCD 502 may further comprise a second speaker 506. Second speaker 506 may also be mounted on the face shield or frame near the other ear. One speaker may be mounted on a rigid component inside of the HCD and a speaker mounted on a rigid component outside of the HCD. The speakers may be wired or use wireless technology such as Bluetooth™. The speakers may be connected to a device containing a library of music such as an mp3 player or smartphone.

HCD 502 embodiment may further comprise a microphone 508. The microphone can be used to capture audio signals outside the HCD. The microphone can be mounted on the face shield and could be wired or use wireless technology. One microphone may be mounted on a rigid component inside of the HCD and a speaker mounted on a rigid component outside of the HCD. This allows for easy and clear communication to others of the outside world. The microphone may be a voice activated microphone. The HCD may be equipped with Bluetooth® technology to allow for making and receiving phone calls or streaming to a device for music, video, etc with a smart phone or wearable smart device. Device to device audio connections could be privately paired, or public according to signal strength. This way, other users nearby will only be heard according to distance, like normal audio. The HCD may further comprise a speaker with an amplifier to amplify outside sounds or amplify the voice of the user to others outside. The HCD may further comprise a cellphone system utilizing speakers and a microphone. The communication hardware component may comprise speakers to provide audio signals to the user and a microphone to capture sounds outside the device and an audio signal processor configured to process input from the microphone and provide noise-cancelling audio signals to the user through the speakers.

In some embodiments, a passive, non-electronic device may be used to enhance the hearing of a user of an HCD. For example, an "ear-outside-ear" type device may be used. An ear trumpet-like device may be used that is located near where the ears of the user would be located in the HCD and would penetrate and pass through the face shield or frame but would further comprise a membrane or diaphragm to add in transmitting sound but also prevent unfiltered air from entering or leaving the device.

The HCD may further comprise a universal serial bus (USB) port, of any type, or any other type of data and/or charging port.

The HCD may further comprise a video display such as a liquid crystal display (LCD), a light emitting diode (LED) display or an electrophoretic reflective display. Alternatively, the display may be formed by images projected onto a surface, such as the inside surface of the face shield. The display may be mounted on the other inner or outer surface of the face shield such that the display is not in the direct view of the user. The video display provides images for augmented reality, way-finding, Global Positioning System (GPS), maps, or environmental warnings.

The displays may be in the form of an optical head-mounted display (OHMD) 510 that is mounted on the face shield. The OHMD (510) may be "smart glasses" such as Google Glass or Apple Glass. An HCD described herein may comprise a holographic projection system to project a display onto the inner surface of the face shield. Any of the communication hardware devices described herein may be powered by a power source such as a battery pack mounted on the HCD or in the frame of the HCD. A solar cell can be used to charge the power source.

In some embodiments, the video displays may be used for gaming applications. The HCD may be integrated with a gaming console for a user to play E sports, adventure, or other games while wearing the device.

In some embodiments, the HCD may comprise a night vision device. The device may be slid down over the eyes and may be located inside or outside of the face shield. In some instances, the night vision device may be a stationary device mounted to the frame or face shield. In this instance, the HCD may only be used for night vision purposes.

The HCD may further comprise an antenna. The antenna may be used to pick up radio and other frequencies. The antenna may be sewed into the fabric component, coated onto the face shield, or inside the frame, or incorporated into the device in any manner. The antenna may be used to communicate with other users of an HCD.

The HCD may comprise one or more lights in the HCD. The lights may be LEDs and are to provide a lighted atmosphere for the user. This is particularly useful in dimly lit conditions inside or at night. In a preferred embodiment, the one or more lights are situated inside and at the top of the HCD though the lights may be located throughout the device. The lights may be configured to direct light rays in front of the face of the user. The lights may also be needed to indicate the presence of a user. One or more lights may be located on an outward surface of the HCD. The internal lights may be helpful for someone to view the face of the user in dimly lit environments.

Electromagnetic Radiation (EMR) Filtering Face Shield for HCD with Filtering Fabric The following embodiments describe designs and methods to filter electromagnetic radiation hitting the face shield from a user wearing an HCD.

Figure 11:
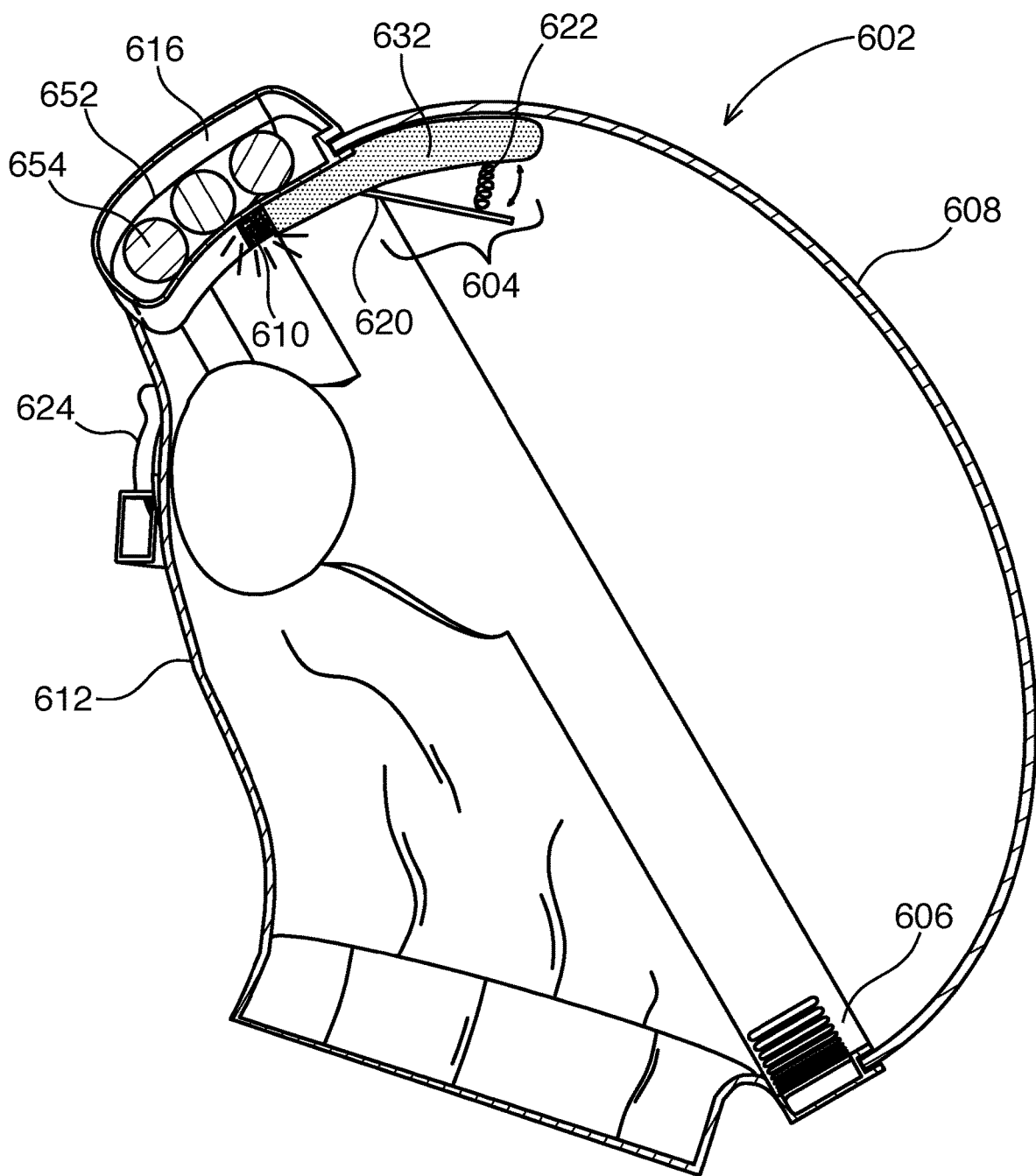
FIG. 11 is a view of an HCD with an electromagnetic radiation filtering face shield, according to an embodiment of the disclosure.

FIG. 11 is a view of an HCD 1002 with an electromagnetic radiation filtering face shield 1004, according to an embodiment of the disclosure. HCD 1002 comprises an FFC 1012, frame 1006, channel 1010, compartment 1016 and noise reduction devices 1018. FIG. 11 further shows HCD 1002 with an electromagnetic radiation (EMR) filtering face shield 1004. The face shield comprises a layer that completely or partially covers the face shield that can be tuned to selectively filter one or more wavelengths or wavelength ranges of EMR, such as ultra-violet (UV), visible, or infrared (IR) radiation. In a preferred embodiment, face shield 1004 filters UV light only. In some embodiments, particularly those used for healthcare environments, or for travel, the transparent face shield may be transparent to infrared (IR) radiation to allow for determination of the temperature of a user.

Face shield 1004 may comprise a photochromic layer. The photochromic layer reversibly darkens in the presence of UV radiation, such as from sunlight. The photochromic layer reversibly darkens in the presence of UV-A light (wavelengths of 320-400 nm). The photochromic layer reversibly darkens in the presence of both UVA and UVB light. The photochromic layer comprises an inorganic material such as AgCl. The photochromic layer comprises an organic material such as an oxazine or a napthopyran-based material. The photochromic layer may comprise the material used in Transitions® lenses.

The face shield may comprise a polarizing filter layer. The polarizing layer may be a linear polarizer or circular polarizer. The polarizing layer may be tuned to filter visible, UV, IR, radio waves, microwaves, or X-rays.

The face shield may comprise an electrochromic layer. The electrochromic layer comprises an inorganic material such as $WO_3$. The electrochromic layer comprises an organic material such as a conducting polymer or a viologen-based material. The conducting polymer may be a polyaniline, polythiophene, poly(3,4-ethylenedioxythiophene) (PEDOT), or a polypyrrole-based polymer or combinations thereof.

Figure 12:
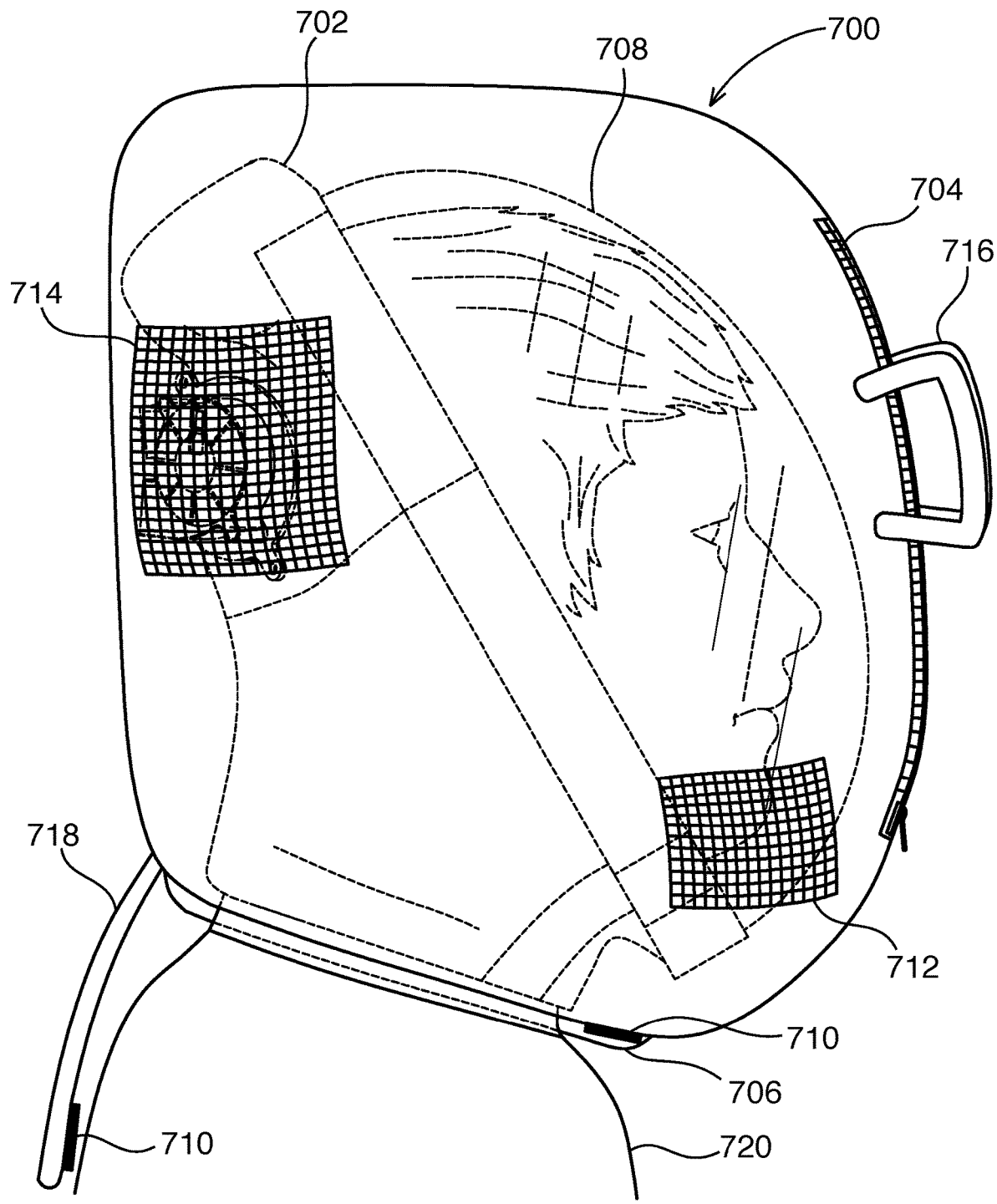
FIG. 12 is a view of an HCD with a patternable electromagnetic radiation filtering face shield, according to an embodiment of the disclosure.

FIG. 12 is a view of an HCD 1020 with a patternable electromagnetic radiation filtering face shield 1022, according to an embodiment of the disclosure. Face shield 1022 comprises a layer that partially covers the face shield to filter one or more wavelengths or wavelength ranges of EMR, such as UV, visible, or IR radiation. The face shield comprises a patternable EMR filtering layer such as a patternable photochromic layer, electrochromic layer, or polarizing layer.

FIG. 12 shows the EMR filtration layer on the top half of the face shield 1022. The EMR layer acts as a sunshade wherein a user may not need to wear a pair of sunglasses behind the face shield. Additionally, the partial EMR filtration layer helps to keep the user cool by reflecting EMR radiation from the top of the head and eyes of a user. Only blocking a portion of the light that passes through the face shield allows the HCD 1020 to be used indoors.

In some embodiments, a moveable visor may be used instead of a permanent EMR filtering layer on the face shield. Such a visor can be mounted either on the inside or on the outside of the face shield. In either event, the moveable visor may be slid across the face shield. The visor is moveable and can be moved to overlap at least a portion or all of the face shield. The moveable visor may be opaque to all EMR. The moveable visor may be tuned to be opaque to only select wavelengths or ranges of wavelengths such as UV, visible, IR, X-rays, or microwaves. At least a portion of the transparent face shield is opaque to ultra-violet (UV) radiation. The moveable visor may be part of the frame wherein the visor may be slid up and down or side to side over the face shield. In other embodiments a detachable visor may be used to block specific wavelengths of light. The detachable visor may be attached and unattached with a device such as a hook and loop fastener, buttons, clips, screws, or other mechanism. The visor may be on the inside or outside of the face shield.

Smart App for Working with an HCD with Filtering Fabric

The following embodiments describes a personal air filtration system (PAFS), such as an HCD, wherein the electronic functions can be controlled and monitored by a configured smart app running on a user's smart device. The smart app may be compatible with smart devices, such as smart phones, tablets, and wearables. The smart app may also include natural language processing (NLP) capabilities to allow for hands-free device usage, greater accessibility for individuals with disabilities, convenience, and novelty. The smart app may have augmented reality capabilities. The smart app may include predictive analytics for a more personal and engaging experience based on past movements and activities. The smart app may utilize biometric data, GPS, or other sensory hardware to provide information about the user, their environment, and their location. The smart app can be downloaded onto a mobile device such as a wearable, tablet, laptop, or cell phone. The smart app can be downloaded onto a non-mobile device such as a desk top computer.

Figure 13:
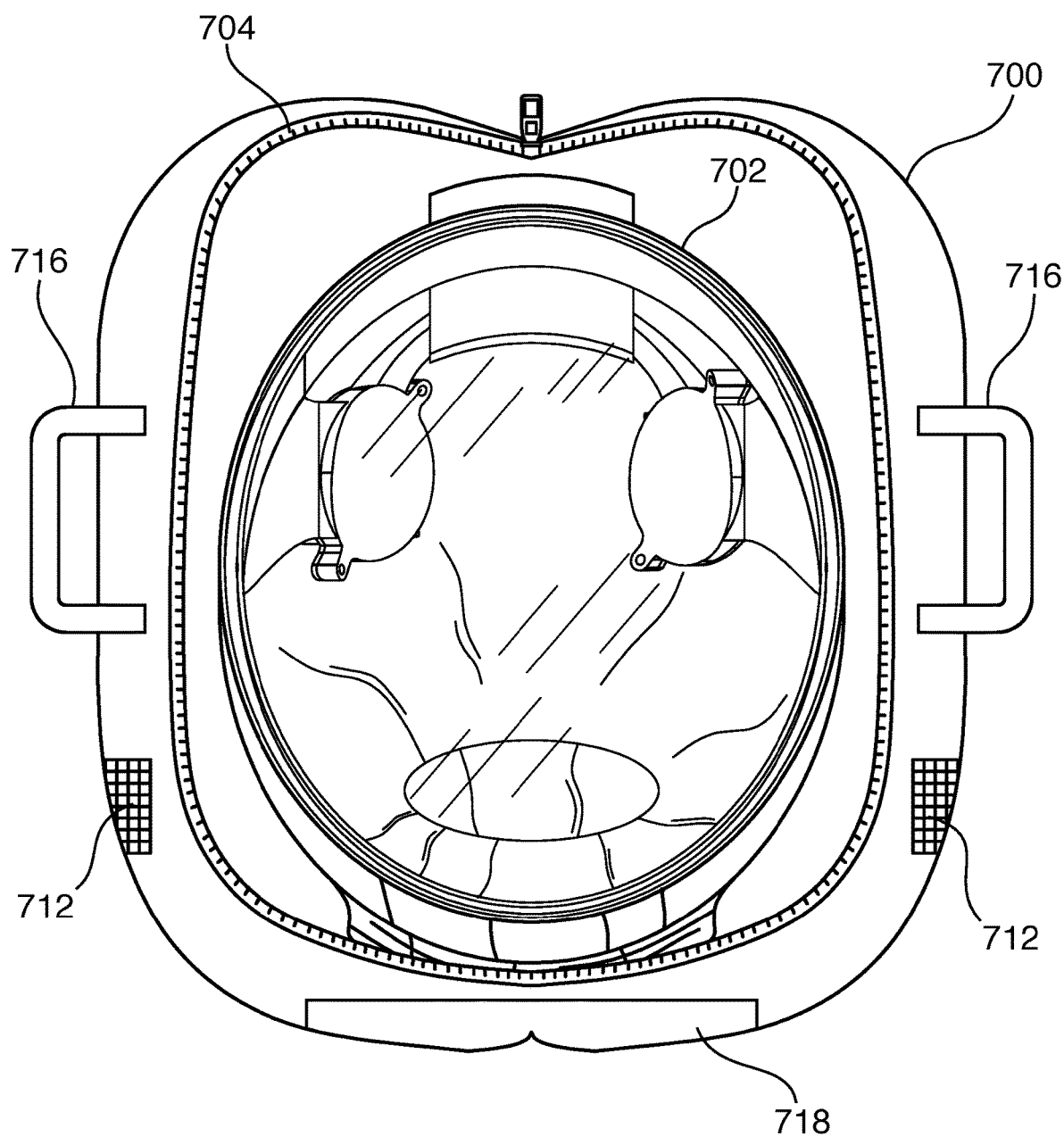
FIG. 13 is a view of user with an HCD that is controlled and monitored by an app on a smart device, according to an embodiment of the disclosure.

FIG. 13 is a view of user with an HCD 1200 that is controlled and monitored by an app on a smart device 1202, according to an embodiment of the disclosure. The HCD is similar to other HCD embodiments described herein comprising a flexible FFC component 1240, rigid face shield component 1242, air moving device 1244, and compartment 1210 to store a power source such as rechargeable batteries. The HCD further comprises an antenna 1212 to receive a wireless signal that is extended from the top of the HCD. The extending antenna may be rigid or a flexible whip antenna. In other embodiments, the antenna may be hidden from view within the frame of the HCD or under the FFC. In other embodiments the antenna may be in the form of wires located on the surface of the rigid face shield or frame.

The HCD comprises a controller that may include one or more communication systems, including Bluetooth communication chips, Internet Wi-Fi transceivers, network transceivers, a wireless mesh network device such as Z-Wave network transceiver, or a combination thereof to wirelessly communicate with a smart device. The controller may be mounted in the rigid component of the HCD. The controller is able to control various components of the HCD such as the rate of the air mover, humidity level, temperature, dimming of the face shield using an electrochromic layer, audio visual and communication components such as an image or video display, microphone, or speaker on demand from the user using an app on a smart device. The smart device may be a stand-alone smart device or integrated with the rigid component of the HCD. The one or more communication systems may communicate by a wireless signal 1214 with at least one of external remote controllers and a cloud-based network in real-time, intermittent time, or in pre-determined time intervals and lengths of time or a combination thereof.

The one or more communication systems may receive instructions from the external remote controller, generate signals 1216 instructing components of the HCD to operate and to monitor the status of various components. The communications system may generate a signal 1214 informing the external remote controller of the status of at least one device in the HCD. In an exemplary embodiment, the remote controller is a smart device such as a tablet, wearable, or mobile phone 1202.

The smart device communicates to a plurality of devices within the HCD. The smart device may also include a wireless transmitter and wireless transceiver and have a connection to each network device of the one or more HCD devices. The connection may include a wired or wireless interface such as Bluetooth, WIFI, mesh network or similar wireless protocol.

Figure 14:
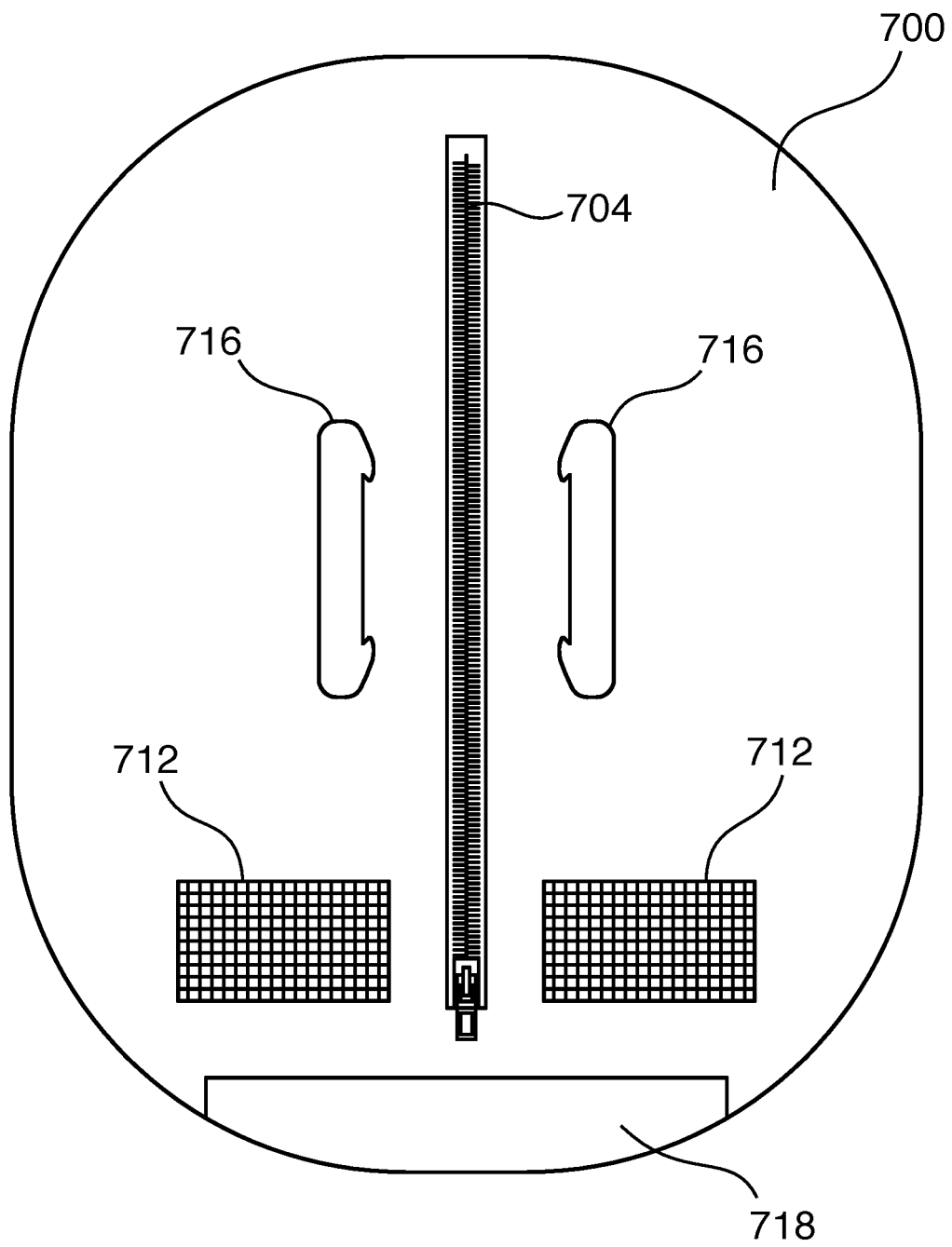
FIG. 14 shows a graphical user interface for monitoring and controlling functions of an HCD, according to an embodiment of the disclosure.
Figure 15:
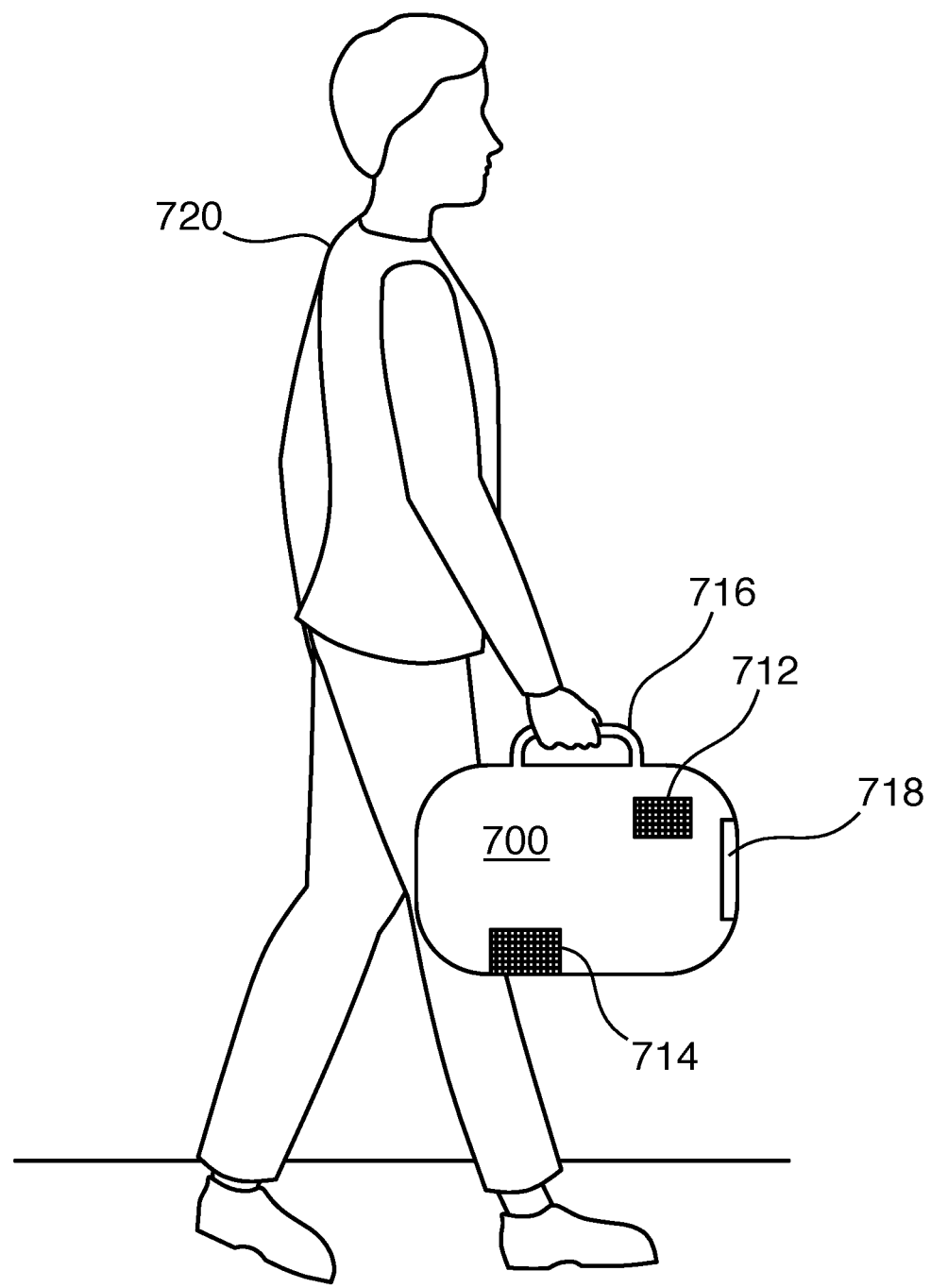
FIG. 15 shows a graphical user interface for monitoring and controlling functions of an HCD, according to an embodiment of the disclosure.
Figure 16:
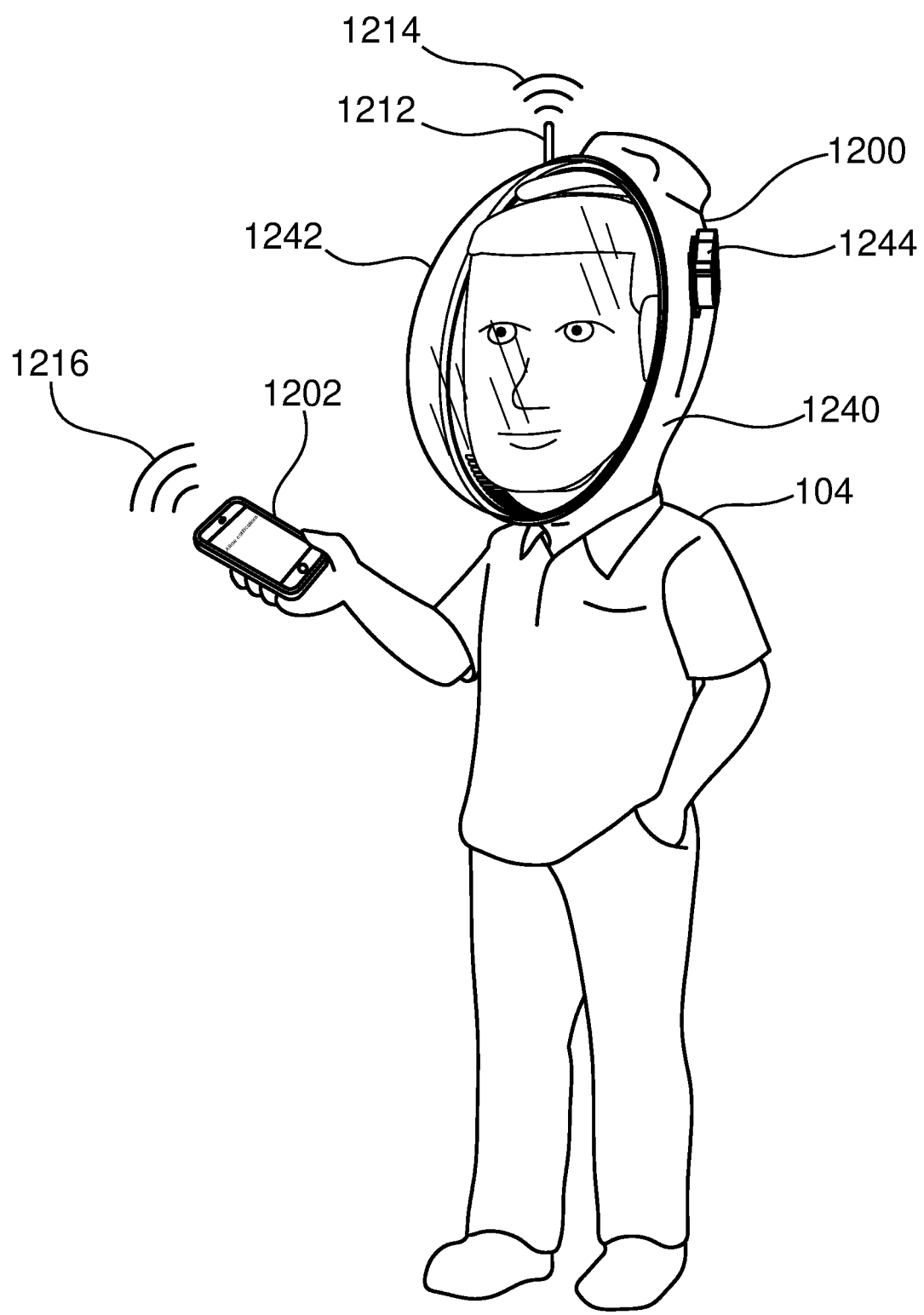
FIG. 16 shows a graphical user interface for monitoring biometric information, according to an embodiment of the disclosure.

FIGS. 14 through 16 show various exemplary graphical user interface (GUI) pages associated with an application configured to execute on a mobile device. Nevertheless, in other embodiments, the application may be configured to execute on a desktop computer, workstation, tablet, laptop, or other suitable computing device.

FIG. 14 shows a graphical user interface for monitoring and controlling functions of an HCD with an app, according to an embodiment of the disclosure. The GUI example embodiment 1204 displayed on a mobile phone 1202 displays various information and multiple indicators and control functions. The name "Michael's Head Covering Device" as displayed at the top of the screen along with standard information such as the time, temperature, weather conditions, and battery charge level of the smart device. Although the name "Michael's Head Covering Device" is used for the name of the HCD for illustrative purposes, the user can give the HCD device any name. In this embodiment, the battery charge status, whether the HCD is plugged in a charging, and the variable fan speed indicators 1206 are displayed. The app may provide an audible alert or a visual alert for the user on the GUI if the battery level goes below a certain level where a limited amount of usage time is left. Controls for the fan speed 1208 are also shown wherein touching "−" decreases the fan speed and pressing "+" increases the fan speed. Towards the bottom of the GUI is a control function where a user can touch "ON" or "OFF" to turn the lights on in an HCD. The lights may be lights inside or outside of the HCD.

FIG. 15 shows a graphical user interface for monitoring and controlling functions of an HCD, according to an embodiment of the disclosure. In this GUI embodiment 1220, the temperature and air flow rate 1222 inside the HCD are displayed. The temperature can be switched by touching an icon 1224 on the screen to toggle between °F. and °C. depending on what is desired by a user. Other functions 1226 may be controlled such as activating an electrochromic layer to dim the face shield, control the internal temperature of the HCD, turn up the hearing volume for the user to hear others, or turn up the speaking volume for others to better hear the user of an HCD. Electromagnetic radiation sensors may be used to determine if the electrochromic layer needs to be activated to limit amount of light entering the face shield and provide shade (i.e., shade function) to the user or by a command from the user.

In some embodiments, the mobile device app may be able to monitor and control more than one HCD. At the bottom of GUI embodiment 1220, a user can touch "Add New Device" 1228 to add another HCD. The HCD could be added by a QR code located on the HCD or search by the name of the HCD. A Bluetooth verification method could be used to create a connection between the mobile phone device and the HCD. A QR code located on an HCD device could also be scanned to link the HCD to the mobile phone app.

FIG. 16 shows a graphical user interface for monitoring biometric information, according to an embodiment of the disclosure. In this example, various biometric data are displayed 1230 such as body temp, pulse rate (beats per minute (BPM)), breathing rate (breaths per minute (BPM)), blink rate (blinks per minute (BPM)), and oxygen ($O_2$) saturation levels that are collected by various sensors in the HCD. Other biometric data may be displayed such as head orientation, closed eyes, and combinations thereof. The app may be able to store and monitor the biometric data for more than one user. This can be achieved by touching "Add Another User" 1232 shown at the bottom of the GUI. The biometric data can be selectively collected on a user if the designated user is confirmed by a fingerprint or retinal scanner. An HCD may further comprise a processor for receiving signals from biometric sensors and communicate biometric information to the smart device, and wherein the app is configured to receive and process biometric information and provide reports to the user.

The app may provide alerts for any information collected by the HCD such as performance of the HCD itself or biometric data collected on the user. The alerts may be programmed and set by the user or may be set based on the age, weight, height, or other information of the user.

The app may receive signals from one or more sensors to test and/or monitor fitment of the system such as the detection of leaks around the seal of the flexible fabric component and the neck area of the user. The sensors may be able to detect a gas for use in testing fitment.

The app may provide alerts for information collected by safety sensors in occupational safety applications such as exterior temperature, noise level, or air quality. The app may be configured to control the temperature, air flow, and volume inside of the HCD based on the ambient noise levels in occupational and non-occupational settings. Air pressure differences may also be monitored by one or more sensors and relayed to the smart device and displayed by the app.

In some embodiments, the app may provide audio assistance to users who are blind and cannot read the GUI. The audio assistance would read what is one the GUI to the user. The volume of the audio could be controlled for the hearing impaired. The app may be used to control video images or projections within the HCD.

The app may be configured to provide an intercom system with one or more users using a similar HCD system.

The app may be configured to provide filter end of useful life alerts to the user based on at least one of age of the filter, increased head pressure on the filter and optical readings indicating a dirty filter.

Variable Flow Head Covering Device (VFHCD)

The following embodiments relate to a variable flow head covering device (VFHCD) capable of negative, positive, or neutral air flow to provide a comfortable and controlled environment for a user.

Figure 17:
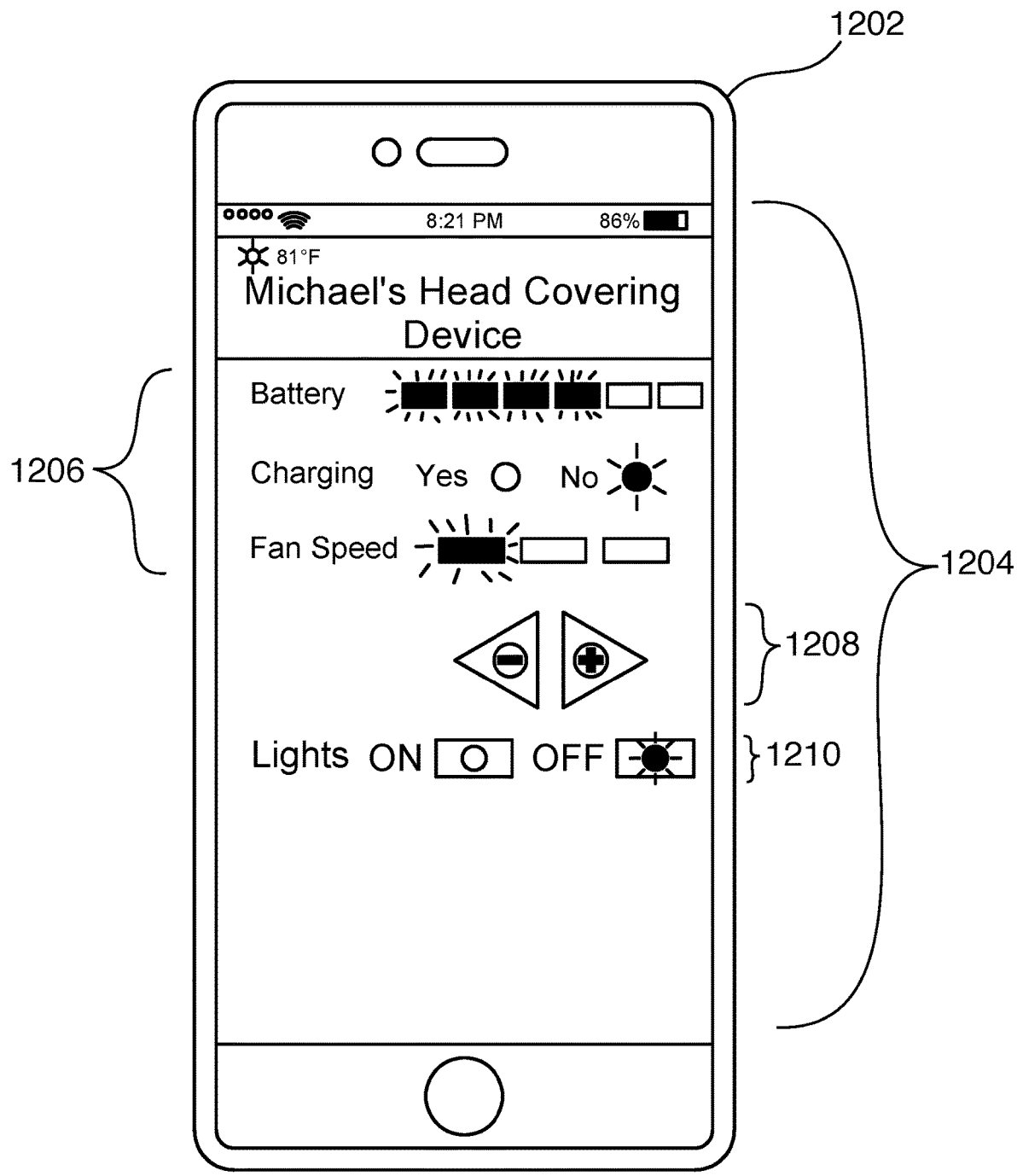
FIG. 17 is a front view of a user wearing a variable flow head covering device (VFHCD), according to an embodiment of the disclosure.

FIG. 17 is a front view of a user wearing a variable flow head covering device (VFHCD) 1500, according to an embodiment of the disclosure. A VFHCD 1500 is placed over the head of a user 1502. The VFHCD comprises a rigid frame 1504 and a rigid transparent face shield 1506. Frame 1504 may be constructed from a rigid or semi-rigid material. Frame 1504 is a hoop-like structure wherein the perimeter of the frame has a generally oval shape but may also be generally circular or some other appropriate shape, such as pear-shaped. Frame 1504 comprises a channel 1508. The edge of the face shield 1506 may be placed in and sit in the channel.

Frame 1504 may be constructed from a rigid polymer or metal or a combination thereof. The polymer may comprise fiberglass, carbon fiber, graphene, polyamide, polycarbonate (PC), polyester, high density or low density polyethylene, polyethylene terephthalate (PET), polypropylene (PP), polystyrene (PS), polyurethane, polyvinyl chloride (PVC), polyvinylidene chloride, acrylonitrile butadiene styrene (ABS), polymethylmethacrylate (PMMA), polytetrafluorethylene (PTFE), phenolic, polyetheretherketone (PEEK), maleimide, bismaleimide, polyetherimide, polyimide, plastarch, furan, silicone, polysulfone, rubber, or a combination thereof. The frame may have a generally oval shape and circles a user's head, with a lower half passing below the user's chin and an upper half passing above a user's forehead.

The face shield 1506 is shaped as a hemi-ellipsoid and is preferably set close enough to the face of a user where the user's eyes are unable to focus on the inner surface of the face shield, and thus not interfere with the vision of the user. The face shield may be permanently attached to the frame 1504 or may be detachable from frame. If permanently attached, this may be accomplished by using an adhesive, thermal welding, or some other means. If detachable, the face shield may be held securely to the frame using an attaching device, such as a hook and loop fastener (Velcro®), clamps, clasps, magnets, screws, or other means.

The face shield may have a thickness in the range of about 0.05-0.25 inches. In the depicted embodiment, the face shield 108 has a thickness of about 0.125 inches. The face shield may be constructed from materials that are approved for impact resistance by the American National Standards Institute (ANSI). The face shield may be double-walled, preferably with a vacuum therebetween, for extra insulation. The face shield may comprise a scratch resistant coating or layer on the inner and/or outer surface to prevent abrasions or other damage. The face shield may comprise an anti-fogging coating on the inner or outer surface. A replaceable protective layer may be placed over the outer surface of the face shield. Naturally, the replaceable protective layer should comprise a transparent polymer.

A top portion of the transparent face shield may extend above a user's eyes, a bottom portion extends below the user's mouth and a first and second side portion extend beyond the user's side peripheral vision. The top portion of face shield may extend above a user's forehead and the bottom portion extends below the user's chin.

In a preferred embodiment, face shield 1506 is a rigid transparent polymer or glass. The polymer may comprise an acrylic such as polymethylmethacrylate. The polymer may comprise polystyrene (PS), polycarbonate, glycol modified polyethylene terephthalate (PETG), or cellulose acetate butyrate or a combination thereof. In some embodiments, the face shield is made from a laminate of polymeric films, each contributing to the structural or optical properties of the face shield. As an example, one layer of the laminate may be included to provide shatter resistance.

In some embodiments, the face shield further comprises an area in the line of sight for a user that provides eye correction and improved vision. The VFHCD may be able to project images on the internal surface of the face shield. For example, the VFHCD may be capable of AR for a user.

In other embodiments, the transparent face shield further comprises a mechanical wiper and motor to clear debris from the front surface of the face shield. In still other embodiments, the transparent face shield further comprises a vibrator to vibrate the face shield to clear debris from the front surface of the face shield. The vibrator may be an ultrasonic vibrator or a pneumatic hammer.

FIG. 17 also illustrates a view of a fabric component 1508. The fabric component may also be referred to as a neck skirt, neck seal, neck collar, or neck shroud. The fabric preferably fits snugly around the neck 1510 of a user 1502, such that particulates do not able to pass between the fabric and the neck of the user. The fabric may be flexible or stretchable and may be made of a polymer such as polyester, polypropylene, polytetrafluorethylne (PTFE), polyether ether ketone (PEEK), polyethene-co-chlorotrifluoroethene (E-CTFE), silicone, rayon, spandex, Lycra®, viscose, stretched polytetrafluoroethylene (PTFE), or nylon. The fabric may be made of a natural fabric such as cotton or wool, a composite of a natural fabric and a polymer, or a pharmaceutical grade textile.

As depicted, the fabric component 1508 is comprised of a single sheet of fabric. The single sheet of fabric, together with the transparent face shield and the frame, cover a user's entire head and a lower portion of the single sheet of fabric encircles the user's neck and forms a seal therewith. The fabric component comprises a drawstring 1512 to tighten around the neck of a user for better sealing properties. In some embodiments, it is preferred to include buttons on the drawstrings to hold the drawstrings in the tightened position. The drawstring is to facilitate the fabric component forming a seal around the user's neck. Alternatively, the single sheet of fabric may possess enough stretch to allow the device to be placed over the user's head while leaving the lower portion of the single sheet of fabric intact and still capable of forming a seal around the user's neck.

The fabric component shown in FIG. 17 comprises a portion 1508A that is permeable or porous to air and a portion 1508B that is impermeable to air. The impermeable portion may be substantially air-tight and does not cover the frame. The air permeable portion is stretched around the frame 1504, covers the air movers, and allows air to pass through. The fabric component can be releasably attached by stretching around the frame. The fabric component may comprise an elastic band to facilitate stretching around the frame. The air impermeable portion 1508B seals around the neck of a user. The air impermeable portion may be baggy and stretchable to allow a user to stretch the fabric with their hand to dab or scratch their face without breaking the seal around the use's neck. The air permeable and air impermeable portions may comprise materials of the same composition or different compositions. The air permeable and air impermeable portions may be joined by a seam. The fabric component may be removable and washable.

The fabric component 1508 may comprise two or more layers. For example, the air impermeable portion may comprise an inner softer second sheet of fabric located between the air impermeable portion and the skin of the user. The inner sheet may be soft, washable, and absorbent.

The fabric component further comprises an access 1514. The access allows a user to access the controls to the device located on the frame underneath the fabric. The access may be a flap that can be opened and closed and secured shut with a zipper, hook and loop fastener, button, or other method. The access may be located anywhere on the fabric on the periphery of the frame.

In some embodiments, the fabric component or portion may comprise a small foam block or insert that a user can use to scratch their noses without having to remove the VFHCD. The foam block or insert may be mounted on the face shield or on the frame. In other embodiments, the fabric component comprises finger sockets that protrude into the facial area of the VFHCD. Finger sockets allow a user to insert their fingers without compromising the environment inside the VFHCD but yet allow the user to scratch or rub an itch. The fabric component may be baggy and stretchable enough for a user to scratch their nose or dab their face without breaking the seal around the user's neck.

As shown in FIG. 17, the VFHCD 1500 rests on top of the head of the user. A resting pad 1516 is placed at the top of the face shield 1506 that provides support and cushion between the device and the head of the user. The resting pad may comprise a cushion-like material such as cloth, foam, rubber, or other soft material and may be replaceable and washable. Multiple materials, sizes and/or shapes of removable resting pads may be available, so that the user can select the most comfortable one for their size and shape of head.

Also shown in the VFHCD in FIG. 17 are earpieces 1518 to reduce noise, and dampen sound, and reverberations inside of the device as previously described herein. In a preferred embodiment, the earpieces are placed in front of the ears. As with the resting pad, multiple materials, sizes and/or shapes may be available and adaptable to provide comfort to the user depending on the shape and size of their head.

Figure 18:
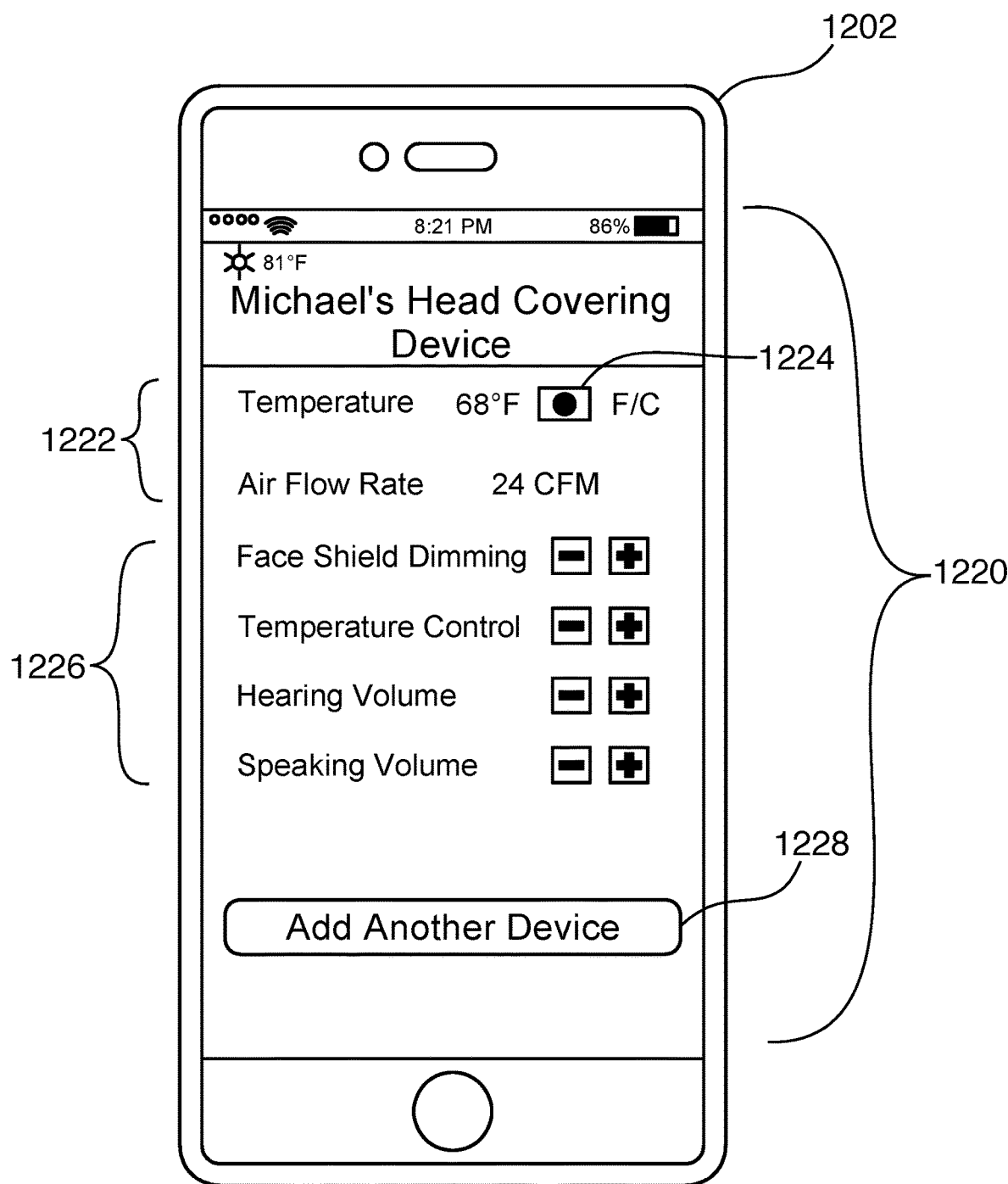
FIG. 18 is a side view of a user wearing a variable flow head covering device (VFHCD), according to an embodiment of the disclosure.

FIG. 18 is a side view of a user wearing a variable flow head covering device (VFHCD) 1500, according to an embodiment of the disclosure. This view further illustrates how the fabric component 1508 is composed of an air permeable portion 1508A and an air impermeable portion 1508B. The fabric component further comprises a first seam 1520 that connects the air permeable portion to the air impermeable portion. The fabric component further comprises a second seam 1522 that connects the air permeable portion 1508A to a top portion 1524 of the fabric. The seams may comprise an elastic material to hold the fabric securely onto the frame. The top portion of the fabric 1524 also aids in preventing the fabric from slipping off the frame. The top portion may be permeable or non-permeable. The first seam

1520 helps to form a seal around the bottom of the frame to prevent air in the neck from escaping that does not pass through a filter.

Figure 19:
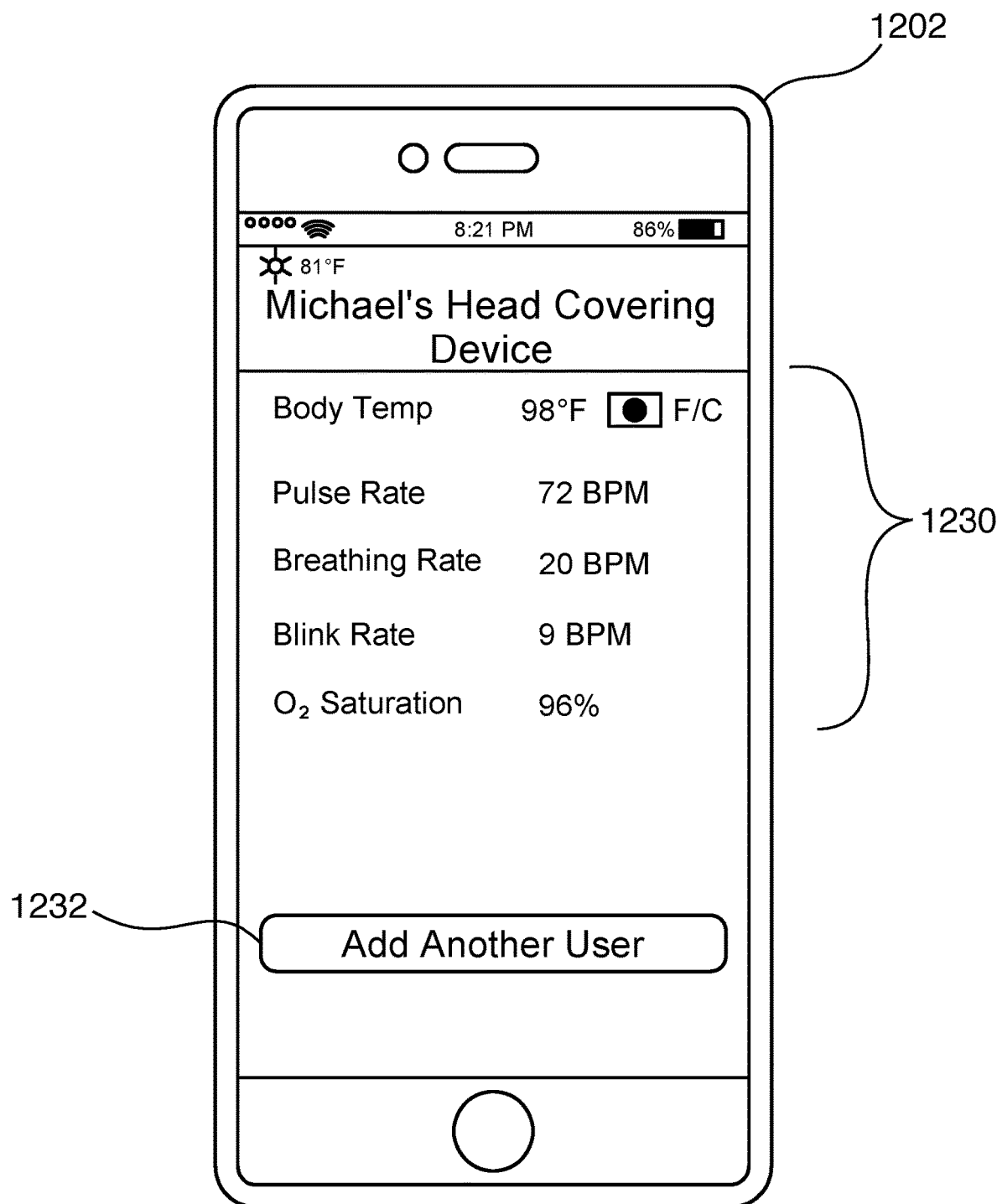
FIG. 19 is a rear view of a user wearing a variable flow head covering device (VFHCD), according to an embodiment of the disclosure.

FIG. 19 is a rear view of a user wearing a variable flow head covering device (VFHCD) 1500, according to an embodiment of the disclosure. This view illustrates how the device may be designed so that it can opened and closed without messing up the hair or makeup of a user. This embodiment comprises a zipper 1526. When the zipper is unzipped, allows the device to be fit over the user's head, and when zipped facilitates the fabric component forming a seal around the user's neck. Other embodiments may comprise an ultra-stretchable fabric that can be opened widely enough to not mess up the hair or makeup of a user.

Figure 20:
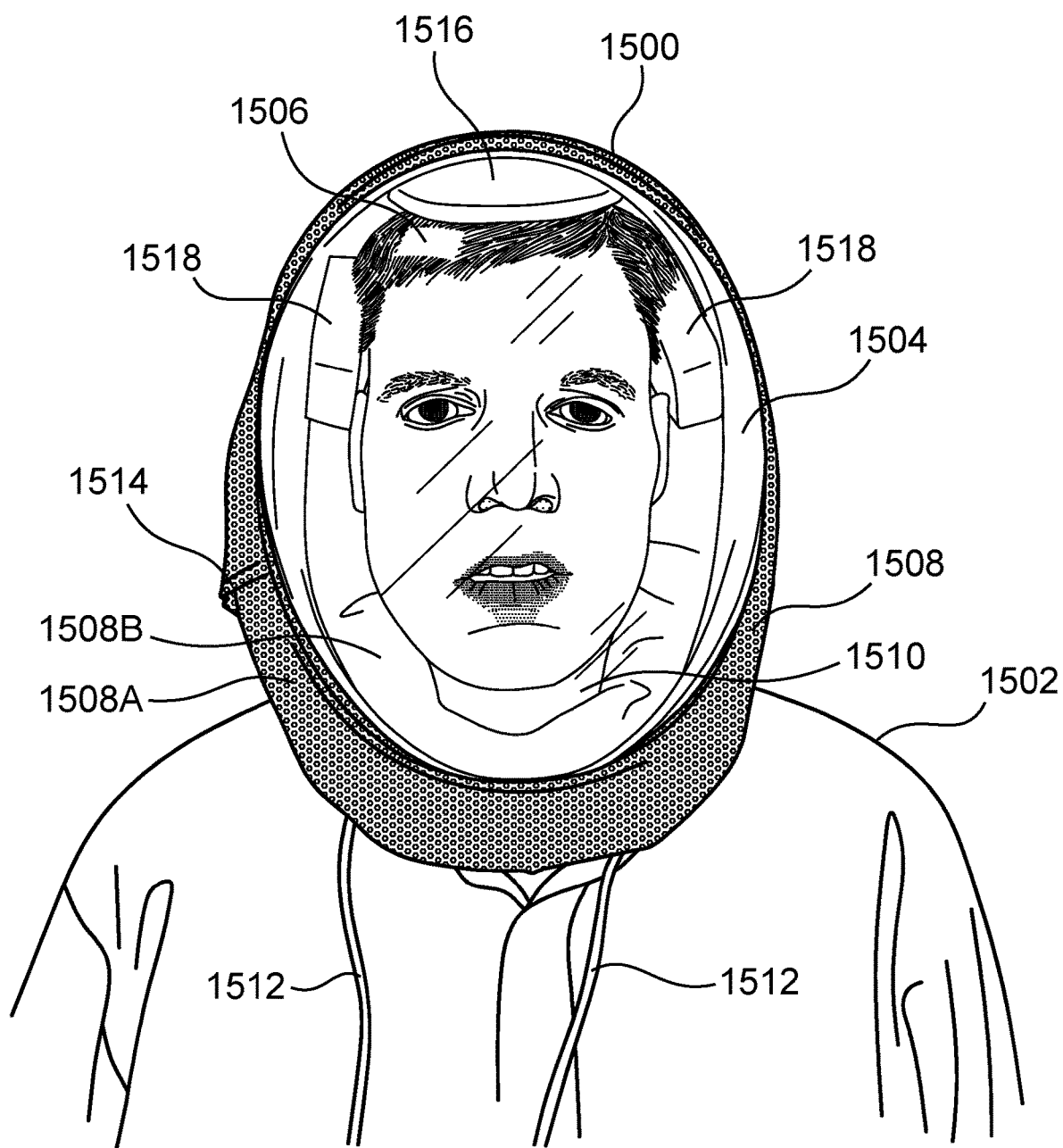
FIG. 20 is an overhead view of a user wearing a variable flow head covering device (VFHCD), according to an embodiment of the disclosure.

FIG. 20 is an overhead view of a user wearing a variable flow head covering device (VFHCD) 1500, according to an embodiment of the disclosure. This view further illustrates how the fabric component 1508 is secured over the frame. The top portion 1524 of the fabric extends over the face shield 1506. The resting pad 1516 extends over the top of the head of the user 1502.

Figure 21:
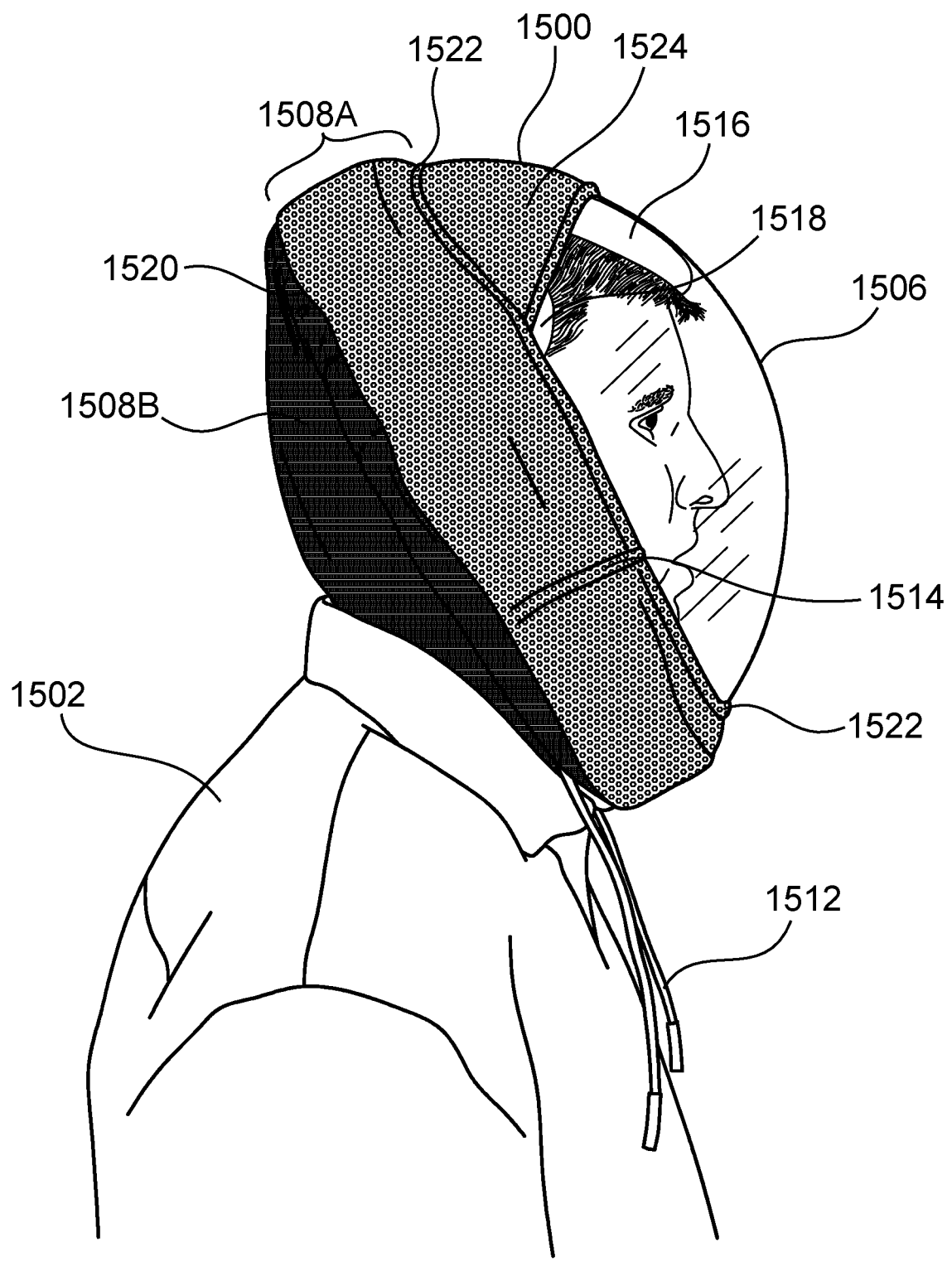
FIG. 21 is a cross-sectional view of a user wearing a variable flow head covering device (VFHCD), according to an embodiment of the disclosure.

FIG. 21 is a cross-sectional view of a user wearing a variable flow head covering device (VFHCD) 1500, according to an embodiment of the disclosure. This view better illustrates the frame and other components of the VFHCD. The face shield sits in a channel 1528 in the frame 1504. The channel runs along the top edge of the frame. The face shield may be reversibly removed from or placed in the channel.

Mounted to the frame is an air mover 1530. The air mover may be a fan or other air moving device as previously described herein. In this embodiment, the air mover may be located near the mouth of a user or may be mounted at any other location on the frame. The frame may comprise one or more air moving devices. The air mover moves air into or out of a port in the frame. The air mover is powered by one or more batteries in a battery pack 1532 that is also mounted to the frame. The battery pack may be mounted at any location on the frame, such as the upper portion of the frame.

The VFHCD further comprises a filter assembly 1534 located on the inside of the frame. In other embodiments, the filter assembly may be located on the outside of the frame. The filter assembly further comprises a filter 1536. The filter assembly can be connected to the frame by hook-and-loop fasteners, clips, snaps, channels, or other mechanism. In a preferred embodiment, the filter assembly can be reversibly removed or attached to the frame. The VFHCD may comprise two or more filter assemblies. The filter is to filter incoming air or outgoing air from inside the device.

Figure 22:
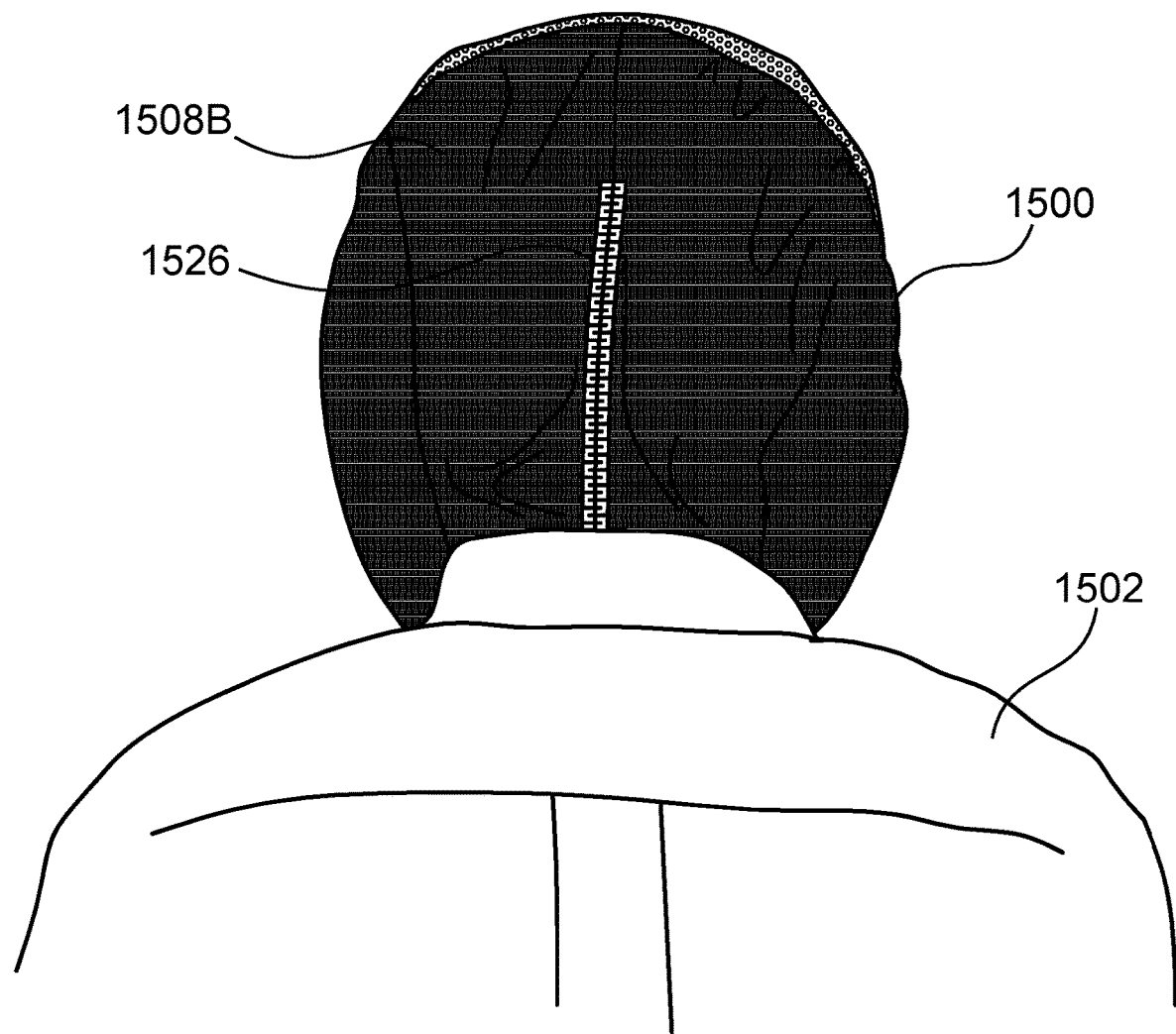
FIG. 22 is a perspective view of the variable flow head covering device (VFHCD) without the fabric and illustrating negative air flow, according to an embodiment of the disclosure.

FIG. 22 is a perspective view of the variable flow head covering device (VFHCD) 1500 without the fabric and illustrating negative air flow, according to an embodiment of the disclosure. This view further illustrates the components of the VFHCD that are typically hidden from view when the fabric component is stretched over the frame 1504. The fans 1530 and battery pack 1532 are mounted to the outer surface of the frame and are in electronic communication with the control box 1564 via electrical wiring 1538. The control box comprises an on/off air mover switch, charge port, and LED (light emitting diode) indicator lights. The control box may comprise other controls to operate components of the VFHCD such as lights, sensors, or air mover speeds.

FIG. 22 further illustrates a port 1540 in the frame. The port may be an air inlet or air outlet port. There may be one or more ports. Air may move into or out of the ports depending on how the air movers 1530 are designed. An air mover may be placed over one, two, three, four, five or all six of the ports in the frame to assist the movement of both inlet and exhaust air. Some air movers may pull air into the device and some air movers push air out of the device. For example, two air movers may pull air out of the device while another two air movers may push air into the device. In another embodiment, two air movers may pull air out of the device while another four air movers my push air into the device. Other combinations of air movers may be used to pull air into the device and push air out of the device.

As illustrated in FIG. 22, air movers, such as fans, can pull air from inside the VFHCD device through the fans to outside of the device forming a negative air flow. This is illustrated by arrows 1544 that pass through a filter 1536 in a filter assembly 1534. The air that enters the device passes through a filter 1536 located in an intake port 1540 (also referred to herein as an inlet port and used interchangeably). Air that is in the device and exhaust air from a user may be exhausted through a filter and out an air mover 1530. This exhaust air is represented by arrows 1544. Each fan is situated directly over a port. There are twice as many additional ports as ports that are situated over the fans. As illustrated in FIG. 22, there are two fans attached to the frame and each fan is located over a port. There are an additional four more ports 1540 to allow for unrestricted air flow that are not located over a fan. Only two are in view in FIG. 22 as the other two are hidden by the filter assemblies. Two fans pull air out of the device through to exhaust ports and filters, while air enters the device through four intake ports and intake filters.

In some embodiments, the air movers may comprise a pressure sensor and a processor receiving input from the pressure sensor. The pressure sensor and processor can be adapted to increase or decrease power to the air mover to thereby regulate the pressure inside the head covering device. In some instances, the user may desire to have neutral air flow in addition to negative or positive air flow. The sensor and processor may be used to control and regulate the desired air flow.

In some embodiments, the inlet port or exhaust port further comprises filter covers to reduce noise entering or exiting the VFHCD 1500. In some embodiments, the fans may be attached with a resilient mount to the frame to reduce noise and vibration.

The filters 1536 located over the air inlet and outlet ports are pleated. This increases the surface are of the filter to increase filtering efficiency and to prevent air flow from being restricted. The surface area of the filters in the device may be greater than 50 inch$^2$. In other embodiments, the surface area of the filters in the device may be greater than 100 inch$^2$. In a preferred embodiment, the surface area of the filters in the device may be greater than 200 inch$^2$. In other embodiments, the filters may not be pleated.

The inlet filter is adapted to block the passage of a virus, bacteria, smog, noxious gas, poisonous gas, smoke, or a combination thereof, to purify the incoming air for a user. The outlet filter may also filter the exhaust air. This is beneficial if a user has an infectious disease which would prevent non-wearers of the VFHCD from being infected. This device could be used in a hospital, nursing home, or other facility by an infected nurse, doctor, or other health care worker without the risk of infecting the patients that they are treating that may have compromised immune systems. The filters can be readily changed depending on the environment where the device is being used. In a preferred embodiment, the filter is a HEPA filter.

Also shown in FIG. 36 are the earpieces 1518 and how they are attached to the face shield. The earpieces are attached to a mount 1546 that is further attached to the face shield. The earpieces can be reversibly removed and reattached to the mounts such as when they may need to be washed or replaced. The earpieces may be attached by hook-and-loop fasteners, an adhesive, snaps, or other mechanism.

Figure 23:
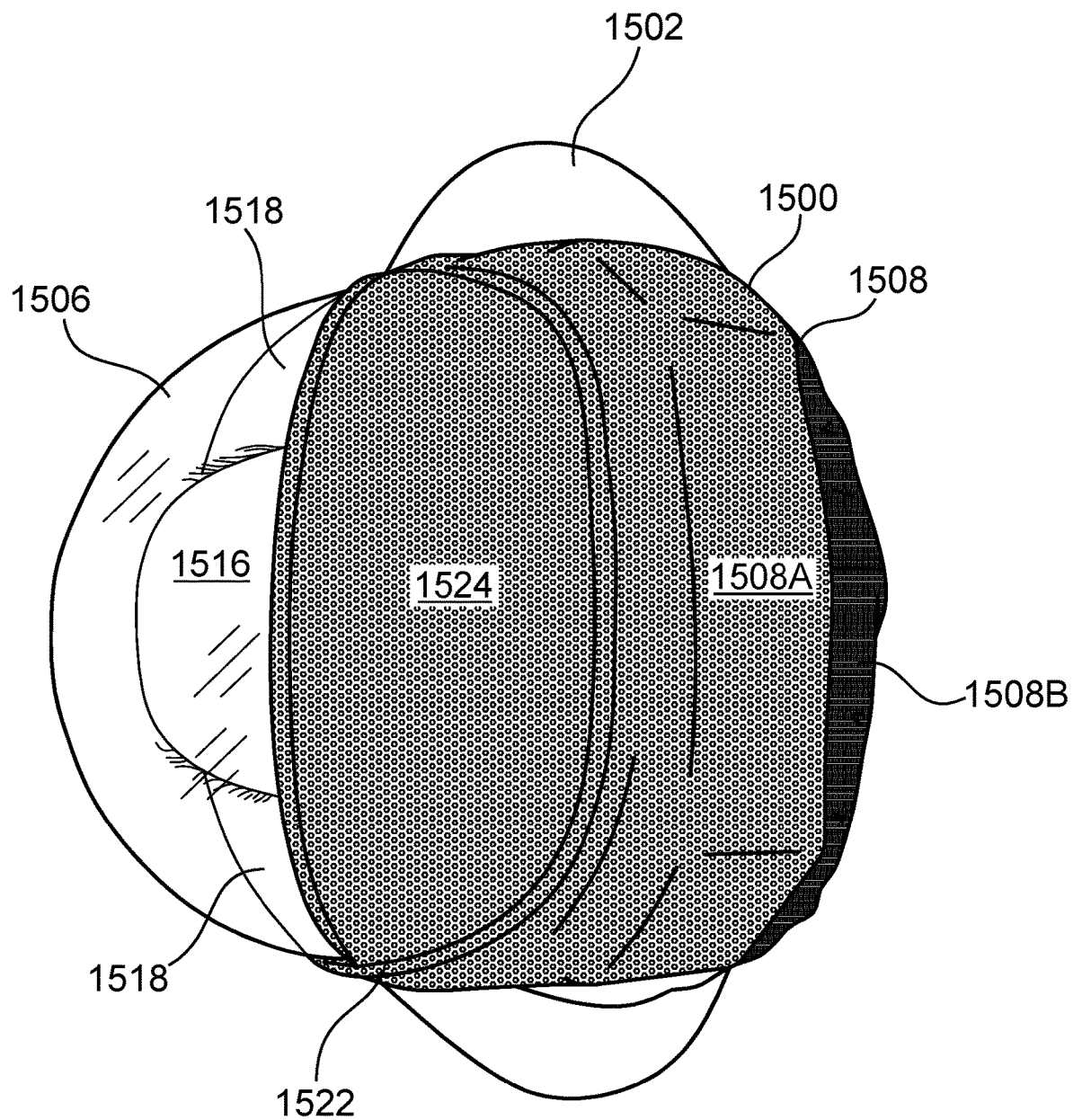
FIG. 23 is a perspective view of the variable flow head covering device (VFHCD) without the fabric and illustrating positive air flow, according to an embodiment of the disclosure.

FIG. 23 is a perspective view of the variable flow head covering device (VFHCD) 1500 without the fabric and illustrating positive air flow, according to an embodiment of the disclosure. As illustrated in FIG. 23, air movers, such as fans, can pull ambient air into the VFHCD device through the fans from outside of the device forming a negative air flow. This is illustrated by arrows 1542. The air that enters the device passes through a filter 1536 located in a filter assembly 1534. Air that is in the device and exhaust air from a user may be exhausted through a filter and out an air outlet 1540. This exhaust air is represented by arrows 1544. Each fan is situated directly over a port. There are twice as many additional ports as ports that are situated over the fans. As illustrated in FIG. 23, there are two fans attached to the frame and each fan is located over a port. There are an additional four more ports 1540 to allow for unrestricted air flow that are not located over a fan. As explained previously herein, many different combinations of air movers may be used that pull air in the device or pull air out of the device.

Figure 24:
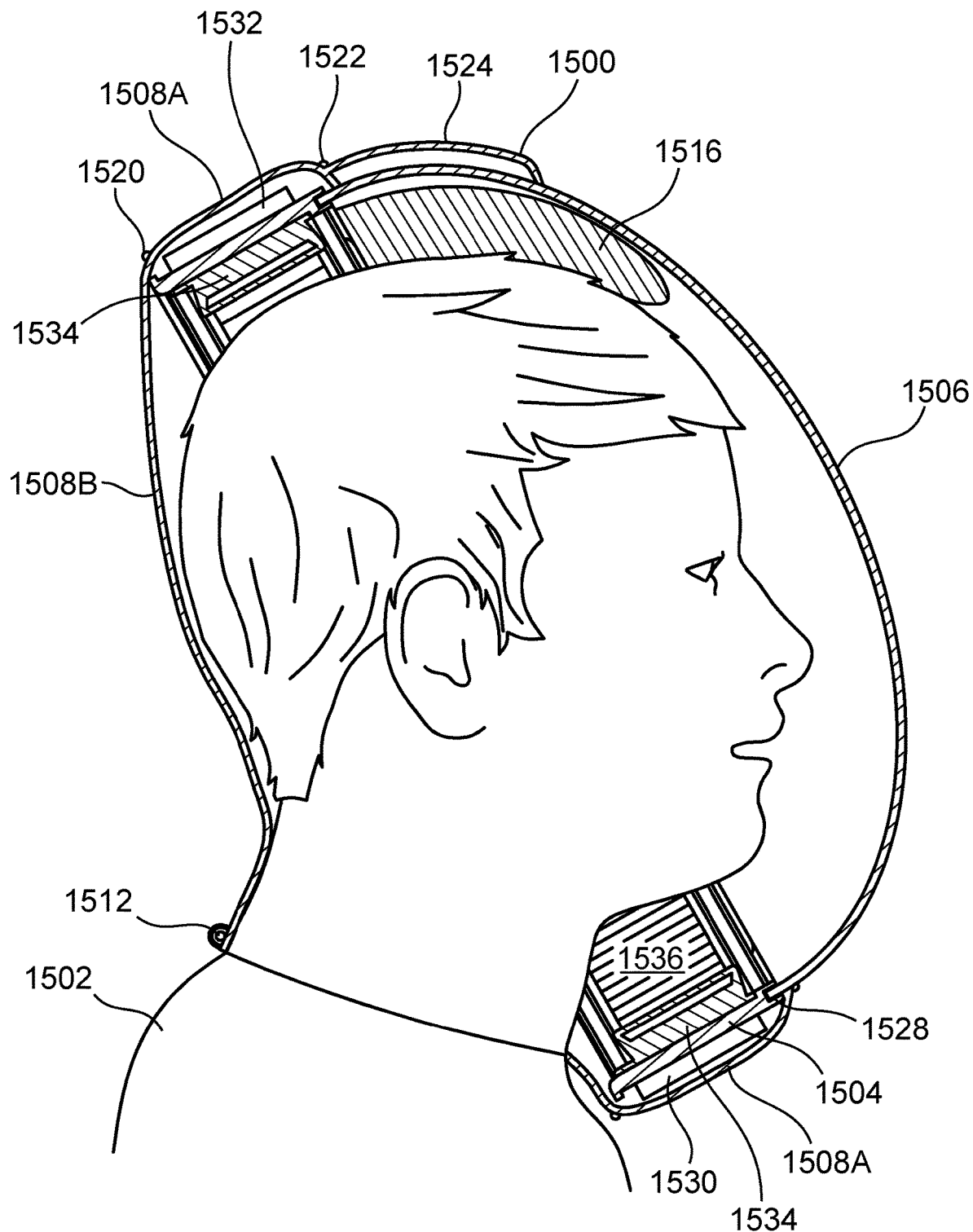
FIG. 24 is a perspective view of the variable flow head covering device (VFHCD) without the fabric and filter assemblies, according to an embodiment of the disclosure.

FIG. 24 is a perspective view of the variable flow head covering device (VFHCD) 1500 without the fabric and filter assemblies, according to an embodiment of the disclosure. Also shown in this view, inlet and outlet ports can be seen. A circular port 1548 can be seen that is located next to a fan 1530. The port may also be square or rectangular-like in shape. Also shown is a hook and loop fastener strip 1550 on the inner side of the frame to where a filter assembly may be attached to. Other devices may be used to attach the filter assembly.

Figure 25:
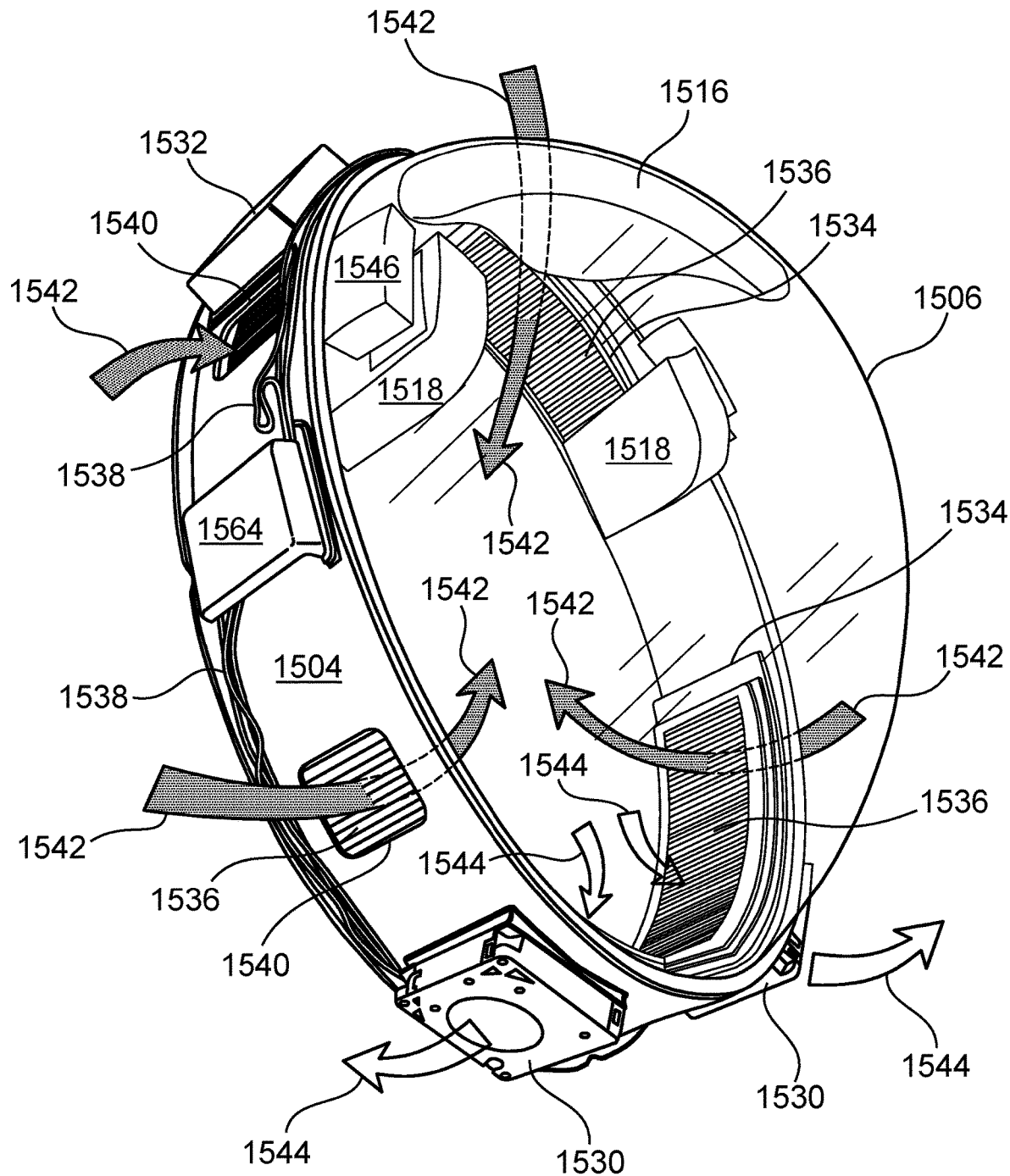
FIG. 25 is a bottom view of the underside of the variable flow head covering device (VFHCD) without the fabric and showing how the filter assemblies are attached, according to an embodiment of the disclosure.

FIG. 25 is a bottom view of the underside of the variable flow head covering device (VFHCD) 1500 without the fabric and showing how the filter assemblies are attached, according to an embodiment of the disclosure. In this view, a filter assembly 1534 has been removed and showing how it sits in the frame as one of four filter assemblies. A hook and loop fastener strip is located on either side of the ports 1540, 1548. Each of the filter assemblies near the bottom of the frame nearest the mouth of a user spans both ports. The filter assemblies at the top of the frame only span a single port 1540. The filter assemblies may be reversibly removed and reattached.

The filter assemblies further comprise a tab 1552. The tab may be used to grab and pull the filter assembly off the hook and loop fastener strips and away from the frame. The filter assemblies have a radius of curvature similar to the radius of curvature of the frame in order to form a uniform distance along the length of the filter assembly between the filter assembly and the frame.

Figure 26:
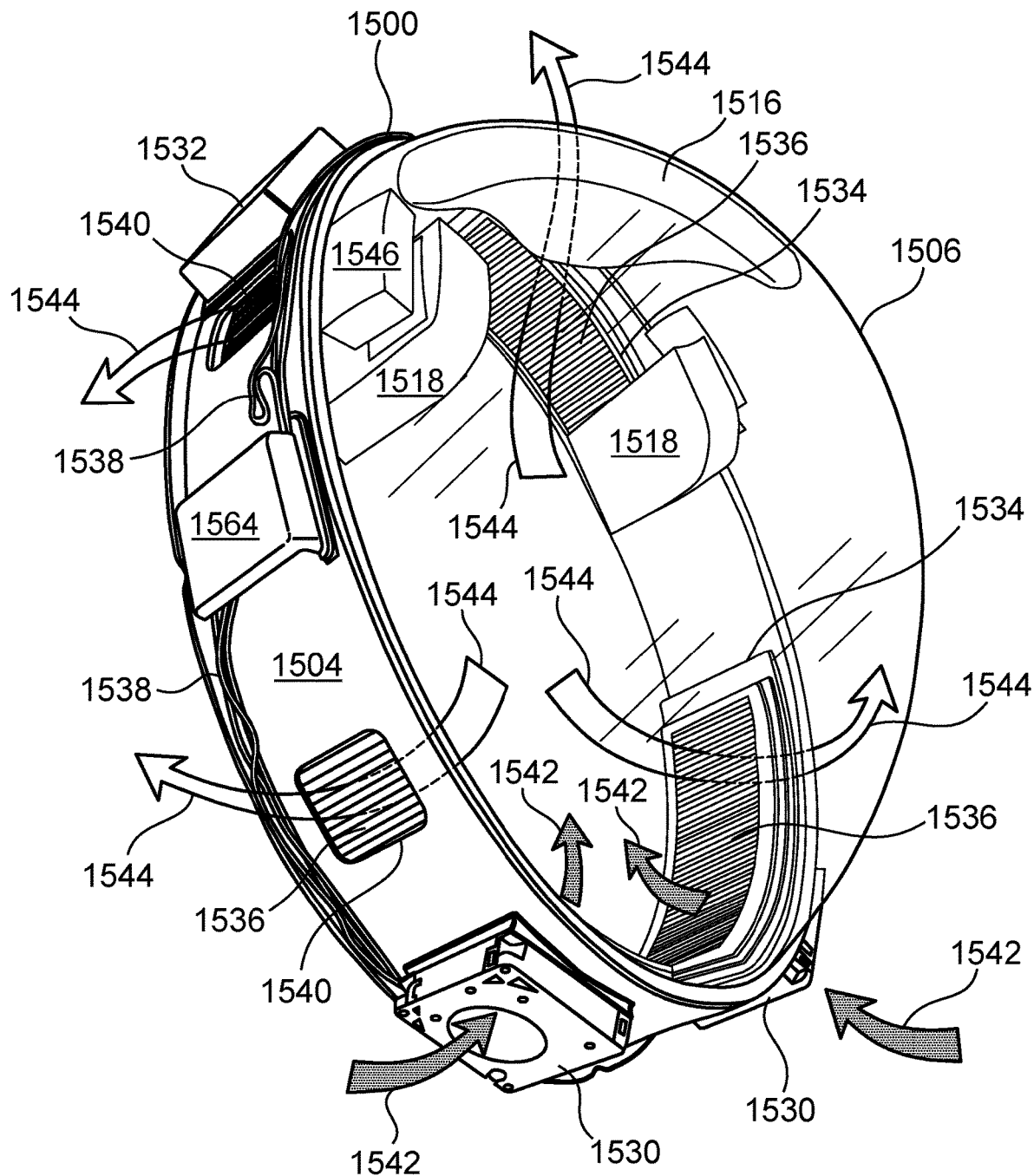
FIG. 26 is a close-up view of a filter assembly, according to an embodiment of the disclosure.

FIG. 26 is a close-up view of a filter assembly 1534, according to an embodiment of the disclosure. The filter assembly comprises a rigid support 1554. The support may comprise a polymer such as polystyrene (PS), high or low density polyethylene, polypropylene (PP), polyacrylonitrile, acrylonitrile butadiene styrene (ABS), polyvinyl chloride (PVC), polycarbonate (PC), polyethylene terephthalate (PET), polytetrafluoroethylene (PET), polymethylmethacrylate (PMMA), polyetheretherketone (PEEK), polyamide, polyimide, or a combination thereof. The support may comprise a metal such as aluminum. The filter assembly comprises a compartment further comprising a filter 1536 that spans the length of the assembly.

The filter assembly further comprises a gasket 1556. The gasket is preferably a soft and flexible material that can form a seal between the filter assembly and the surface of the frame. The gasket may comprise a foam rubber-like material. The gasket can be designed to form a first area 1558 and a second area 1560 wherein the first area is divided from the second area. The first area covers an inlet port and the second area covers an outlet port in the frame. The gasket can substantially prevent inlet air from entering an outlet port and outlet air from entering the inlet port.

The filter assembly further comprises an attaching device to attach the filter assembly to the inner surface of the frame. In a preferred embodiment as illustrated in FIG. 25, the attaching device is a hook-and-loop fastener such as a hook and loop fastener strip 1562. Strip 1562 connects to a receiving strip 1550 located on the frame.

Figure 27:
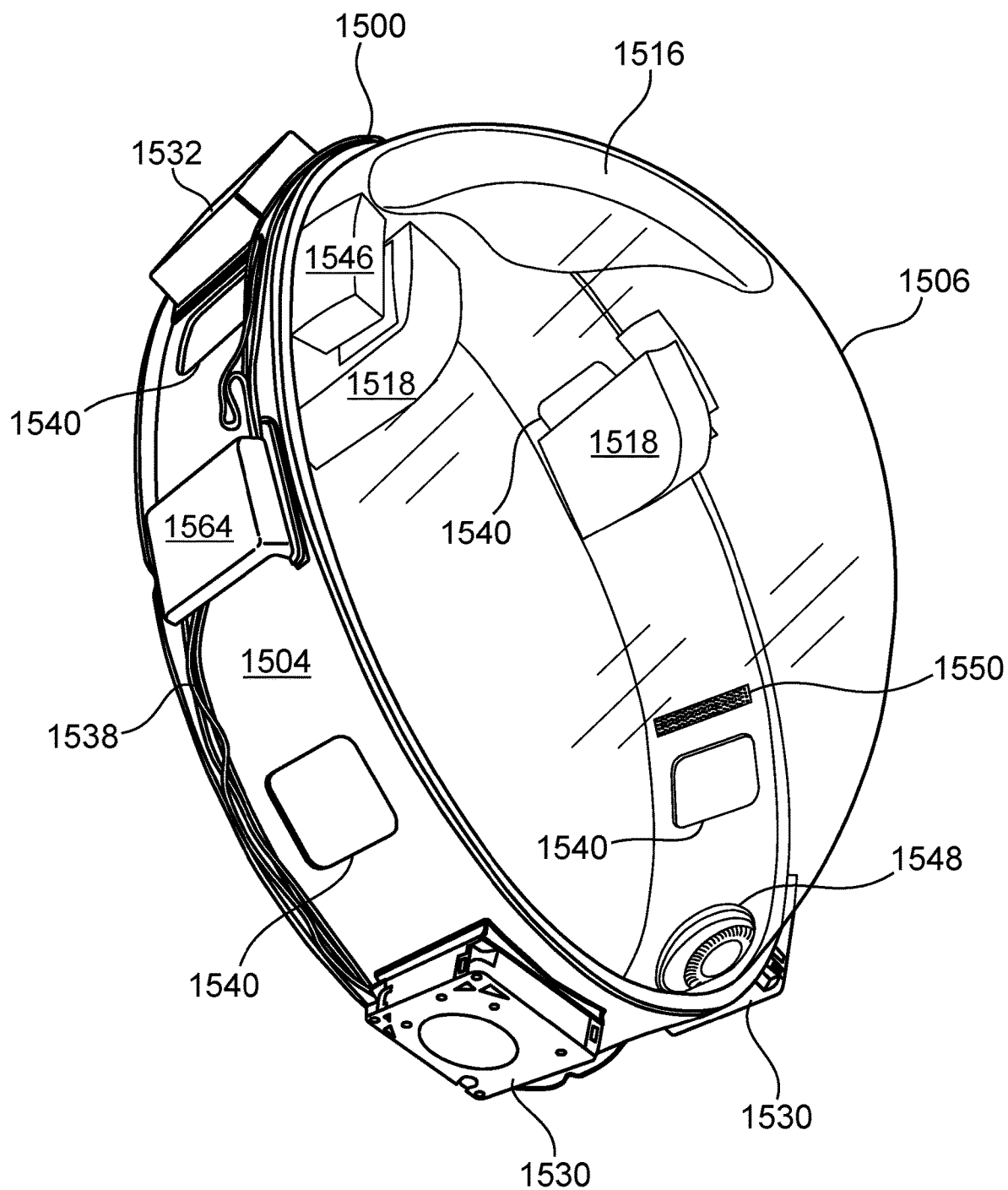
FIG. 27 is a close-up view of the control box, according to an embodiment of the disclosure.

FIG. 27 is a close-up view of the control box 1564, according to an embodiment of the disclosure. The control box is in electrical communication with a battery pack and an air mover. The control box comprises an on/off air mover switch 1566, LED indicator light 1568, and charge port 1570. Other controls may be in the control box such a flow or pressure sensor, an air flow controller, or a combination thereof to control other components of the device. In a preferred embodiment, the charge port to recharge the batteries in the battery pack is a USB-C plug. The charge port may be a USB-A, USB 3.0 A SS, USB B, USB 3.0 B SS, USB mini-A, USB mini-AB, USB mini-B, USB micro-AB, USB micro-B, or a USB 3.0 micro-B SS plug.

Figure 28:
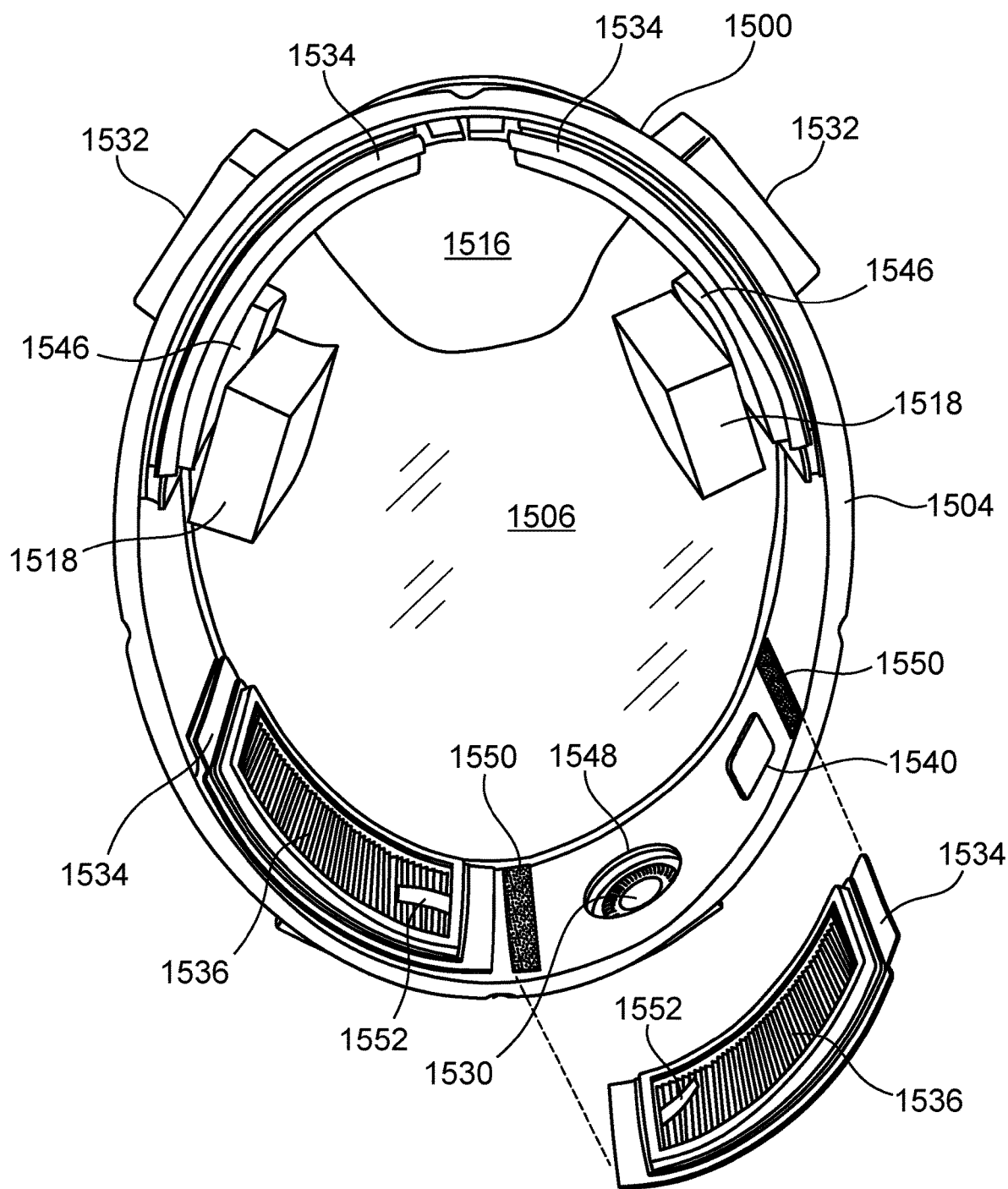
FIG. 28 is a view of the variable flow head covering device (VFHCD) being charged, according to an embodiment of the disclosure.

FIG. 28 is a view of the variable flow head covering device (VFHCD) being charged, according to an embodiment of the disclosure. In a preferred embodiment, the battery pack 1532 comprises one or more rechargeable batteries. The rechargeable batteries may comprise a rechargeable Li ion-based battery such as a $LiCoO_2$, $LiFePO_4$, $LiMnNiCoO_2$, $LiNiCoAlO_2$, or $LiMn_2O_4$-based battery. The rechargeable batteries may comprise a nickel-cadmium or nickel metal hydride battery. FIG. 28 illustrates a charge cord 1572 connecting to the charge port 1570 in the control box 1564 of the VFHCD to a wall socket 1574. The fabric component 1508 has been removed to better illustrate charging. When the fabric component is stretched over the frame, a charge cord may be connected to the charge port in the control box by way of access 1514 previously described herein. In other embodiments, the battery pack may comprise a non-rechargeable primary battery such as an alkaline cell.

Alternative Fan Location in a Variable Flow Head Covering Device (VFHCD)

The following embodiments illustrate alternative locations for the fans in a variable flow head covering device (VFHCD).

Figure 29:
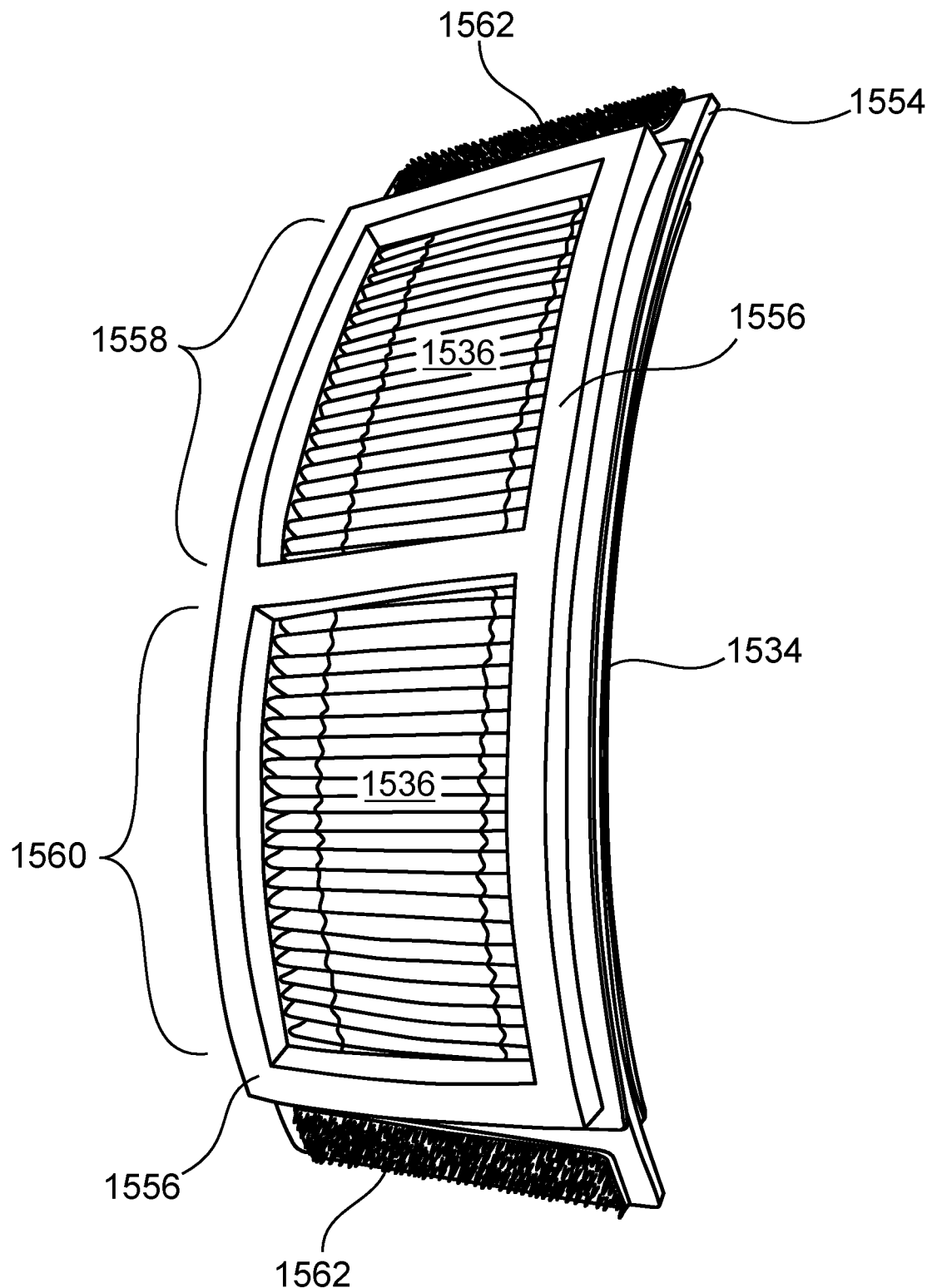
FIG. 29 is a view of a variable flow head covering device (VFHCD) with alternative fan locations, according to an embodiment of the disclosure.

FIG. 29 is a view of a variable flow head covering device (VFHCD) 1600 with alternative fan locations, according to an embodiment of the disclosure. VFHCD 1600 is similar to the disclosed VFHCD 1500 embodiment described previously herein. The VFHCD 1600 embodiment in FIG. 29 does not include a fabric component in order to better view where the fans are placed. VFHCD 1600 similarly includes a frame 1602, transparent face shield 1604, resting pad 1606, earpieces 1608, control box 1610, fans 1612, battery pack 1614, and filter assembly 1616.

In this embodiment, the fans 1612 are moved towards the top of the frame near the battery pack. In the VFHCD 1500 embodiment they are near the mouth of the user. By moving the fans toward the top of the frame, the weight distribution of the device is improved in the VFHCD 1600 embodiment.

Environmental Control for a Variable Flow Head Covering Device (VFHCD)

The following embodiments describe systems and methods to provide a controlled temperature and breathing environment within an HCD by conditioning the air within the HCD with an environmental control component. The environmental control component can control the air flow, temperature, or humidity or a combination thereof within the device.

Figure 30:
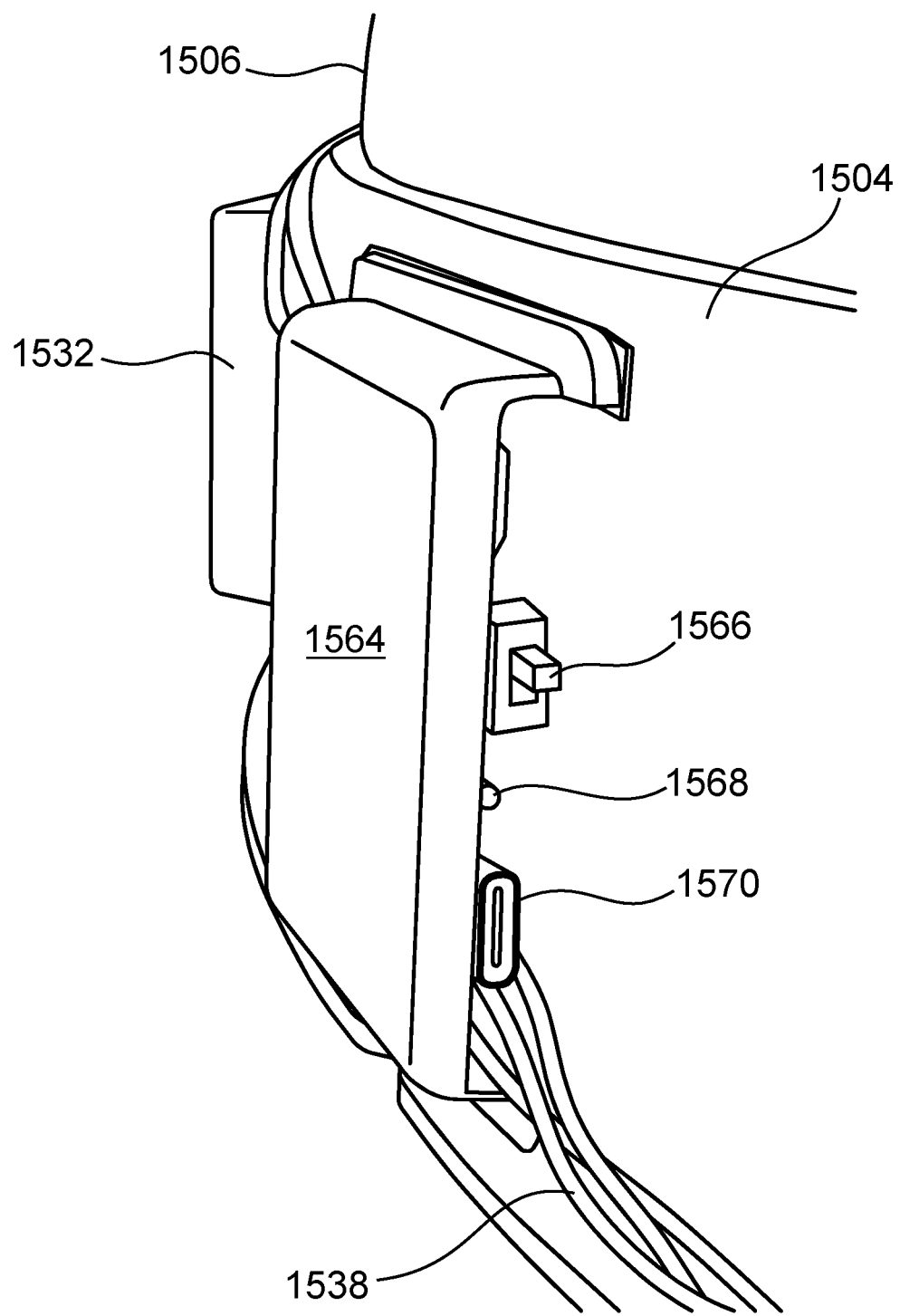
FIG. 30 is a side view of a user wearing a variable flow head covering device (VFHCD) with a pocket, according to an embodiment of the disclosure.

FIG. 30 is a side view of a user wearing a variable flow head covering device (VFHCD) 1700 with a pocket 1702, according to an embodiment of the disclosure. One or more pockets are preferably located over an intake filter or intake fan where air passes through before entering the VFHCD. The pockets are located on the permeable portion 1704 of the fabric.

The pocket may further comprise a thermoelectric cooler. The thermoelectric cooler may be designed to heat or cool incoming air 1706 for the user 1708. The thermoelectric cooler may be combined with a heat exchanger device to increase efficiency of heat transfer between incoming and exhaust air. The thermoelectric cooler may be used to control the temperature of the air to prevent fogging on the face shield 1710 or humidity build-up in the VFHCD. The inner surface of the face shield may comprise an anti-fogging layer. The thermoelectric cooler may operate on the principle of the Peltier effect.

The pocket may comprise an energy recovery or heat recovery device. Such a device would heat incoming intake air with outgoing exhaust air in order to maintain a comfortable environment within the VFHCD as described herein. The pocket may also contain an energy recovery device.

The pocket may comprise a sensor that detects one or more harmful or poisonous gases as the gases enter the VFHCD. The harmful gases may include $CO_2$, CO, NOx, radon, or methanethiol. The pocket 1702 may also contain one or more sensors.

The depicted VFHCD further includes a water reservoir in the pocket. The water reservoir acts as a water source to the neck fabric wherein the water may be wicked by the neck fabric to provide evaporative cooling for the user to provide cooling to the neck area and cool air to breathe.

The VFHCD described herein may comprise a compartment containing a chilled mass such as ice. Incoming air is cooled as it passes over the ice and into the device. As the ice melts, the water is evaporated as the air passes over which can provide a further mode of cooling.

In some embodiments, a pocket may be located inside the fabric component 1704 or inside the VFHCD.

Air flow in the VFHCD embodiment in FIG. 30 occurs as follows. Incoming air 1706 from the environment is pulled in by one or more fans and passes through the pocket 1702 followed by a filter wherein particulates are removed. The air is pulled or pushed in by negative or positive air flow. Exhaust air from the user may then be exhausted through an exhaust filter located in the frame as previously illustrated herein. Air pressure differences may be detected by one or more sensors.

The VFHCD described herein may further include a fluid atomizer or mister. The atomizer may use water in the water reservoir to provide a mist of water inside a VFHCD. A VFHCD described herein may further include an environmental control device that can be used by a user to control the temperature inside the device by raising or lowering the temperature. The environmental control device may further comprise a source of water vapor to increase the humidity of the air inside the device.

The VFHCD described herein may further include a heater. The heater can heat the air inside a VFHCD. The heater may be an electric resistive heater. The VFHCD described herein may further include a chiller to chill the air inside a VFHCD.

In some embodiments, the fabric components described herein may comprise a phase-change material, such as that deployed in high-end sport clothing. The phase-change material, which may be encapsulated in the fabric of the VFHCD or held in reservoirs elsewhere in the VFHCD, works by reversibly storing and releasing heat at pre-defined temperature ranges. In the most common example, the phase change material is used to retain heat in a device designed to be used in sub-zero environments. The material, such as a paraffin or lipid, melts when in an environment with a temperature above a certain point. This melting is endothermic, so the melting cools the inside of the device. When the device is in a colder environment, the material solidifies, e.g., crystallizes, which is an exothermic process, thus warming the inside of the device.

Another temperature-affecting technology that may be incorporated into the impermeable fabric portion 1712 is one that is designed to wick perspiration away from the user. As that perspiration evaporates, the user is cooled thereby. One commercial example of such technology is available from Arctic Cool® in their products sold as HydroFreeze™.

In other embodiments, the VFHCD further comprises a compressor to provide heating or cooling to the device. The compressor may be held in a backpack worn by the user. Preferably, the compressor provides heating or cooling directly to the neck area of the user. The compressor may comprise a 24V DC compressor. Alternatively, the compressor heats and/or cools the air as it is brought into the device.

A VFCD described herein may further include a multi-speed air moving system. The multi-speed air moving system may be a dual speed fan. If a pre-set environmental threshold or parameter is exceeded within the HCD, such as temperature or humidity, the air moving system increases to a higher speed to improve the environment by increasing air flow within the HCD. The air mover may be adjusted continually to maintain a desired target atmosphere in the device.

A VFHCD described herein may include one or more sensors to provide filter end of useful life alerts to the user based on at least one of age of the filter, increased head pressure on the filter and optical readings indicating a dirty filter.

In some embodiments, wearable electronics may be embedded in the neck fabrics, frame, air moving device, or face shield to provide environmental and thermal monitoring within the devices described herein. The wearable electronics may also monitor the temperature, air flow, and air conditions inside the device. The electronics may be powered by the power source used for the air moving device or a separate power source may be used. The electronics may include one or more sensors may be included to detect for air leaks around the fabric component sealed around the neck area.

Communication Component for a Variable Flow Head Covering Device (VFHCD)

The following embodiments include a communication component or hardware with a VFHCD. This communication hardware is used to provide audio and/or video capabilities for the user in a VFHCD. As such the communication hardware facilitates communication with other people who may or may not be wearing an HCD, as well as news, alerts, weather, entertainment, and other services to the user. The communication hardware may also facilitate communication with a smart device such as a smart phone, tablet, or wearable.

Figure 31:
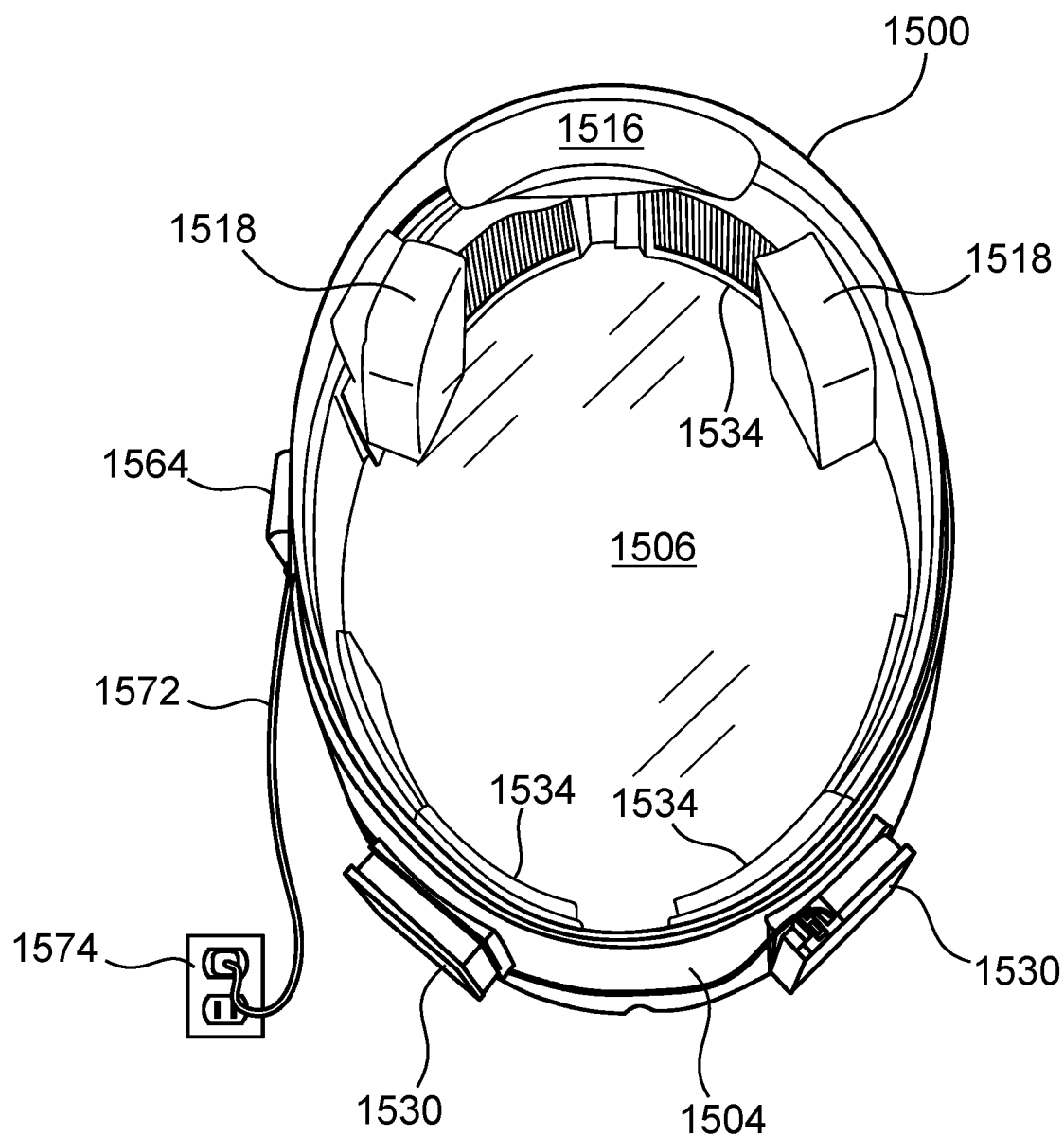
FIG. 31 is a front view of a user wearing a variable flow head covering device (VFHCD) equipped with communication hardware components, according to an embodiment of the disclosure.

FIG. 31 is a front view of a user wearing a variable flow head covering device (VFHCD) 1800 equipped with communication hardware components, according to an embodiment of the disclosure. VFHCD 1800 is similar to other devices disclosed herein comprising a noise reduction device 1802, head rest 1804, and fabric component 1806. The communication hardware may be connected to the internet. The communication hardware may be wirelessly connected to a smart phone. The communication hardware further comprises Bluetooth technology for wireless communication with the smart phone. VFHCD 1800 comprises a speaker 1808. The speaker 1808 communicates audio and may be an earphone, headphone, ear bud, or an earpiece. Speaker 1808 allows a user 1810 to better hear sounds coming from outside the device or to communicate with another person. The speakers may be used to communicate with someone specifically wearing a similar HCD. Speaker 1808 may be mounted on shield 1812 or frame 1814 near one ear. VFHCD 1800 may further comprise a second speaker 1816. Second speaker 1816 may also be mounted on the face shield or frame near the other ear. One speaker may be mounted on a rigid component inside of the VFHCD and a speaker mounted on a rigid component outside of the VFHCD. The speakers may be wired or use wireless technology such as Bluetooth™. The speakers may be connected to a device containing a library of music such as an mp3 player or smartphone.

VFHCD 1800 embodiment may further comprise a microphone 1818. The microphone can be used to capture audio signals outside the device. The microphone can be mounted on the face shield and could be wired or use wireless technology. One microphone may be mounted on a rigid component inside of the VFHCD and a speaker mounted on a rigid component outside of the VFHCD. This allows for easy and clear communication to others of the outside world. The microphone may be a voice activated microphone. The VFHCD may be equipped with Bluetooth® technology to allow for making and receiving phone calls or streaming to a device for music, video, etc such as with a smart phone or wearable smart device. Device to device audio connections could be privately paired, or public according to signal strength. This way, other users nearby will only be heard according to distance, like normal audio. The VFHCD may further comprise a speaker with an amplifier to amplify outside sounds or amplify the voice of the user to others outside. The VFHCD may further comprise a cellphone system utilizing speakers and a microphone. The communication hardware may comprise speakers to provide audio signals to the user and a microphone to capture sounds outside the device and an audio signal processor configured to process input from the microphone and provide noise-cancelling audio signals to the user through the speakers.

In some embodiments, a passive, non-electronic device may be used to enhance the hearing of a user of a VFHCD. For example, an "ear-outside-ear" type device may be used. An ear trumpet-like device may be used that is located near where the ears of the user would be located in the VFHCD and would penetrate and pass through the face shield or frame but would further comprise a membrane or diaphragm to add in transmitting sound but also prevent unfiltered air from entering or leaving the device.

The VFHCD 1800 may further comprise a universal serial bus (USB) port, of any type, or any other type of data and/or charging port.

The VFHCD may further comprise a video display such as a liquid crystal display (LCD), a light emitting diode (LED) display or an electrophoretic reflective display. Alternatively, the display may be formed by images projected onto a surface, such as the inside surface of the face shield. The display may be mounted on the other inner or outer surface of the face shield such that the display is not in the direct view of the user. The video display provides images for augmented reality, way-finding, Global Positioning System (GPS), maps, or environmental warnings.

The displays may be in the form of an optical head-mounted display (OHMD) 1820 that is mounted on the face shield. The OHMD (1820) may be "smart glasses" such as Google Glass or Apple Glass. An HCD described herein may comprise a holographic projection system to project a display onto the inner surface of the face shield. Any of the communication hardware devices described herein may be powered by a power source such as a battery pack mounted on the VFHCD or in the frame of the VFHCD. A solar cell can be used to charge the power source.

In some embodiments, the video displays may be used for gaming applications. The VFHCD may be integrated with a gaming console for a user to play E sports, adventure, or other games while wearing the device.

In some embodiments, the VFHCD may comprise a night vision device. The device may be slid down over the eyes and may be located inside or outside of the face shield. In some instances, the night vision device may be a stationary device mounted to the frame or face shield. In this instance, the VFHCD may only be used for night vision purposes.

The VFHCD may further comprise an antenna. The antenna may be used to pick up radio and other frequencies. The antenna may be sewed into the fabric component, coated onto the face shield, or inside the frame, or incorporated into the device in any manner. The antenna may be used to communicate with other users of an VFHCD.

The VFHCD may comprise one or more lights in the VFHCD. The lights may be LEDs and are to provide a lighted atmosphere for the user. This is particularly useful in dimly lit conditions inside or at night. In a preferred embodiment, the one or more lights are situated inside and at the top of the VFHCD though the lights may be located throughout the device. The lights may be configured to direct light rays in front of the face of the user. The lights may also be needed to indicate the presence of a user. One or more lights may be located on an outer surface of the device. This would be beneficial if using the device at night and act as a headlight for other to be able to see the user. The internal lights may be helpful for someone to view the face of the user in dimly lit environments.

A VFHCD described herein may further include a multi-speed air moving system. The multi-speed air moving system may be a dual speed fan. If a pre-set environmental threshold is exceeded within the VFHCD, such as temperature or humidity, the air moving system increases to a higher speed to improve the environment by increasing air flow within the device.

In some embodiments, the VFHCD comprises an audible alert to provide warnings to the user.

In some embodiments, the VFHCD further comprises an external electronically switchable display to display text or images to people who approach the user. This may be for users who are deaf.

Electromagnetic Radiation (EMR) Filtering Face Shield for a Variable Flow Head Covering Device (VFHCD)

The following embodiments describe designs and methods to filter electromagnetic radiation hitting the face shield from a user wearing a variable flow head covering device (VFHCD).

Figure 32:
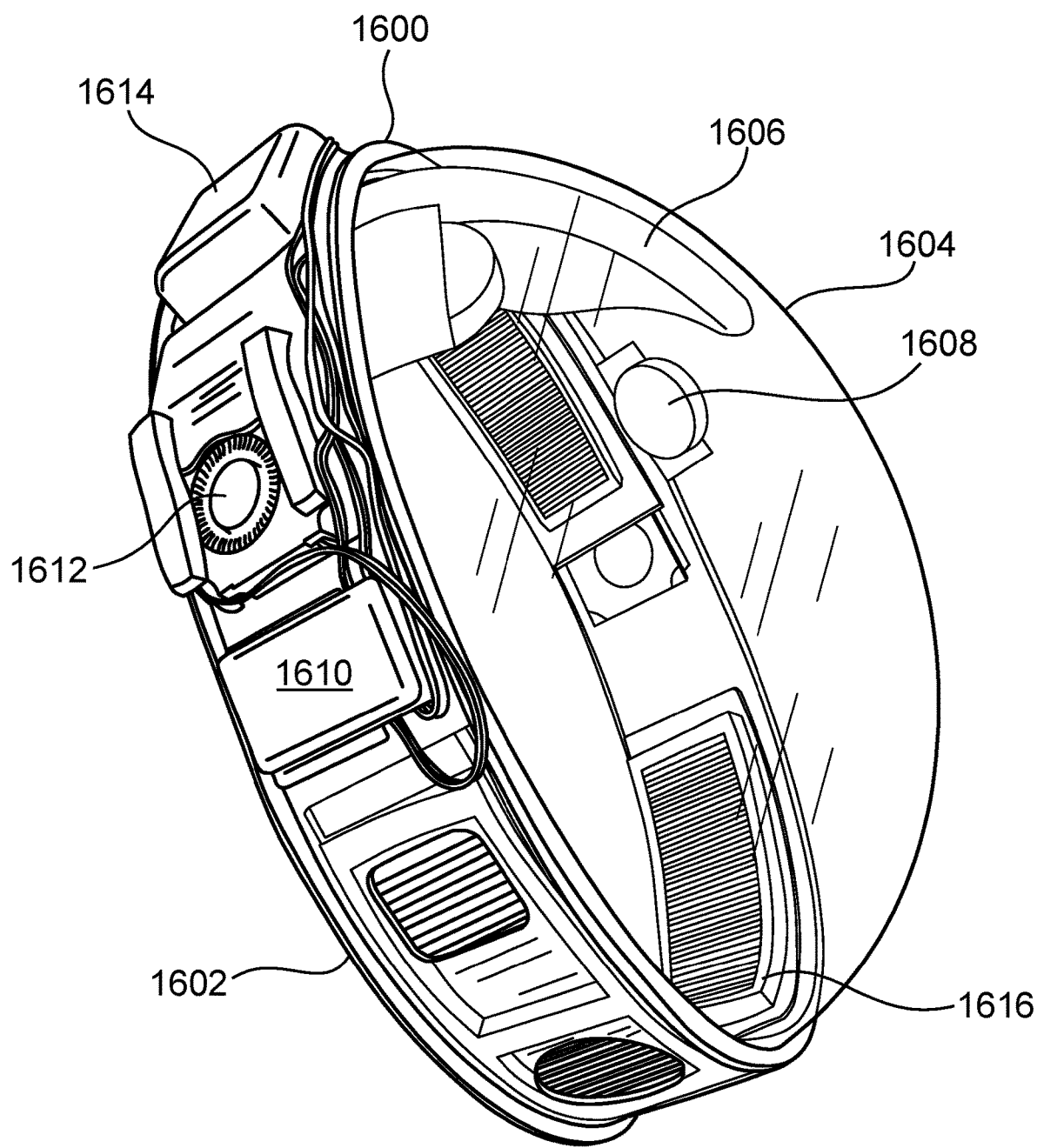
FIG. 32 is a view of a variable flow head covering device (VFHCD) with an electromagnetic radiation filtering face shield, according to an embodiment of the disclosure.

FIG. 32 is a view of a variable flow head covering device (VFHCD) 2000 with an electromagnetic radiation filtering face shield 2002, according to an embodiment of the disclosure. VFHCD 2000 is similar to other HCDs disclosed herein comprising a fabric component 2004, frame 2006, head rest 2008, and noise reduction devices 2010. FIG. 32 further shows an electromagnetic radiation (EMR) filtering face shield 2002. The face shield comprises a layer that completely or partially covers the face shield that can be tuned to selectively filter one or more wavelengths or wavelength ranges of EMR, such as ultra-violet (UV), visible, or infrared (IR) radiation. In a preferred embodiment, face shield 2002 filters UV light only. In some embodiments, particularly those used for healthcare environments, or for travel, the transparent face shield may be transparent to infrared (IR) radiation to allow for determination of the temperature of a user 2012.

Face shield 2002 may comprise a photochromic layer. The photochromic layer reversibly darkens in the presence of UV radiation, such as from sunlight. The photochromic layer reversibly darkens in the presence of UV-A light (wavelengths of 320-400 nm). The photochromic layer reversibly darkens in the presence of both UVA and UVB light. The photochromic layer comprises an inorganic material such as AgCl. The photochromic layer comprises an organic material such as an oxazine or a napthopyran-based material. The photochromic layer may comprise the material used in Transitions® lenses.

The face shield may comprise a polarizing filter layer. The polarizing layer may be a linear polarizer or circular polarizer. The polarizing layer may be tuned to filter visible, UV, IR, radio waves, microwaves, or X-rays.

The face shield may comprise an electrochromic layer. The electrochromic layer comprises an inorganic material such as $WO_3$. The electrochromic layer comprises an organic material such as a conducting polymer or a viologen-based material. The conducting polymer may be a polyaniline, polythiophene, poly(3,4-ethylenedioxythiophene) (PEDOT), or a polypyrrole-based polymer, or combinations thereof.

Figure 33:
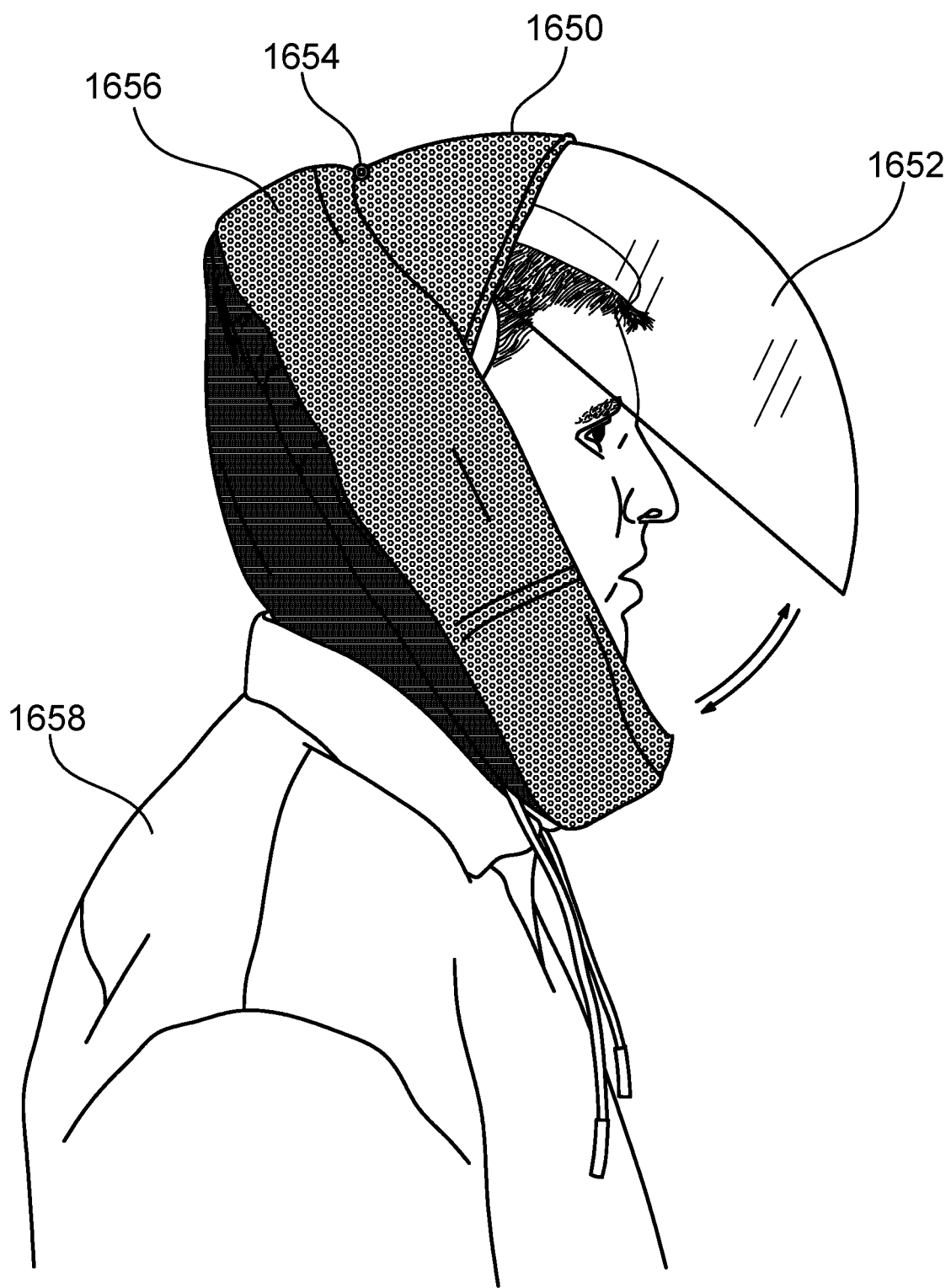
FIG. 33 is a view of a variable flow head covering device (VFHCD) with a patternable electromagnetic radiation filtering face shield, according to an embodiment of the disclosure.

FIG. 33 is a view of a variable flow head covering device (VFHCD) 2050 with a patternable electromagnetic radiation filtering face shield 2052, according to an embodiment of the disclosure. Face shield 2052 comprises a layer that partially covers the face shield to filter one or more wavelengths or wavelength ranges of EMR, such as UV, visible, or IR radiation. The face shield comprises a patternable EMR filtering layer such as a patternable photochromic layer, electrochromic layer, or polarizing layer.

FIG. 33 shows the EMR filtration layer on the top half of the face shield 2052. The EMR layer acts as a sunshade wherein a user may not need to wear a pair of sunglasses behind the face shield. Additionally, the partial EMR filtration layer helps to keep the user cool by reflecting EMR radiation from the top of the head and eyes of a user. Only blocking a portion of the light that passes through the face shield allows the VFHCD 2050 to be used indoors.

In some embodiments, a moveable visor may be used instead of a permanent EMR filtering layer on the face shield. Such a visor can be mounted either on the inside or on the outside of the face shield. In either event, the moveable visor may be slid across the face shield. The visor is moveable and can be moved to overlap at least a portion or all of the face shield. The moveable visor may be opaque to all EMR. The moveable visor may be tuned to be opaque to only select wavelengths or ranges of wavelengths such as UV, visible, IR, X-rays, or microwaves. At least a portion of the transparent face shield is opaque to ultra-violet (UV) radiation. The moveable visor may be part of the frame wherein the visor may be slid up and down or side to side over the face shield. In other embodiments a detachable visor may be used to block specific wavelengths of light. The detachable visor may be attached and unattached with a device such as hook and loop fastener, buttons, clips, screws, or other mechanism. The visor may be on the inside or outside of the face shield.

Smart App for Working with a Variable Flow Head Covering Device (VFHCD)

The following embodiments describes a variable flow head covering device (VFHCD) wherein the electronic functions can be controlled and monitored by a smart app on a smart device. The smart app may be compatible with smart devices, such as smart phones, tablets, and wearables. The smart app may also include natural language processing (NLP) capabilities to allow for hands-free device usage, greater accessibility for individuals with disabilities, convenience, and novelty. The smart app may have augmented reality capabilities. The smart app may include predictive analytics for a more personal and engaging experience based on past movements and activities. The smart app may utilize biometric data, GPS, or other sensory hardware to provide information about the user, their environment, and their location. The smart app can be downloaded onto a mobile device such as a wearable, tablet, laptop, or cell phone. The smart app can be downloaded onto a non-mobile device such as a desk top computer.

Figure 34:
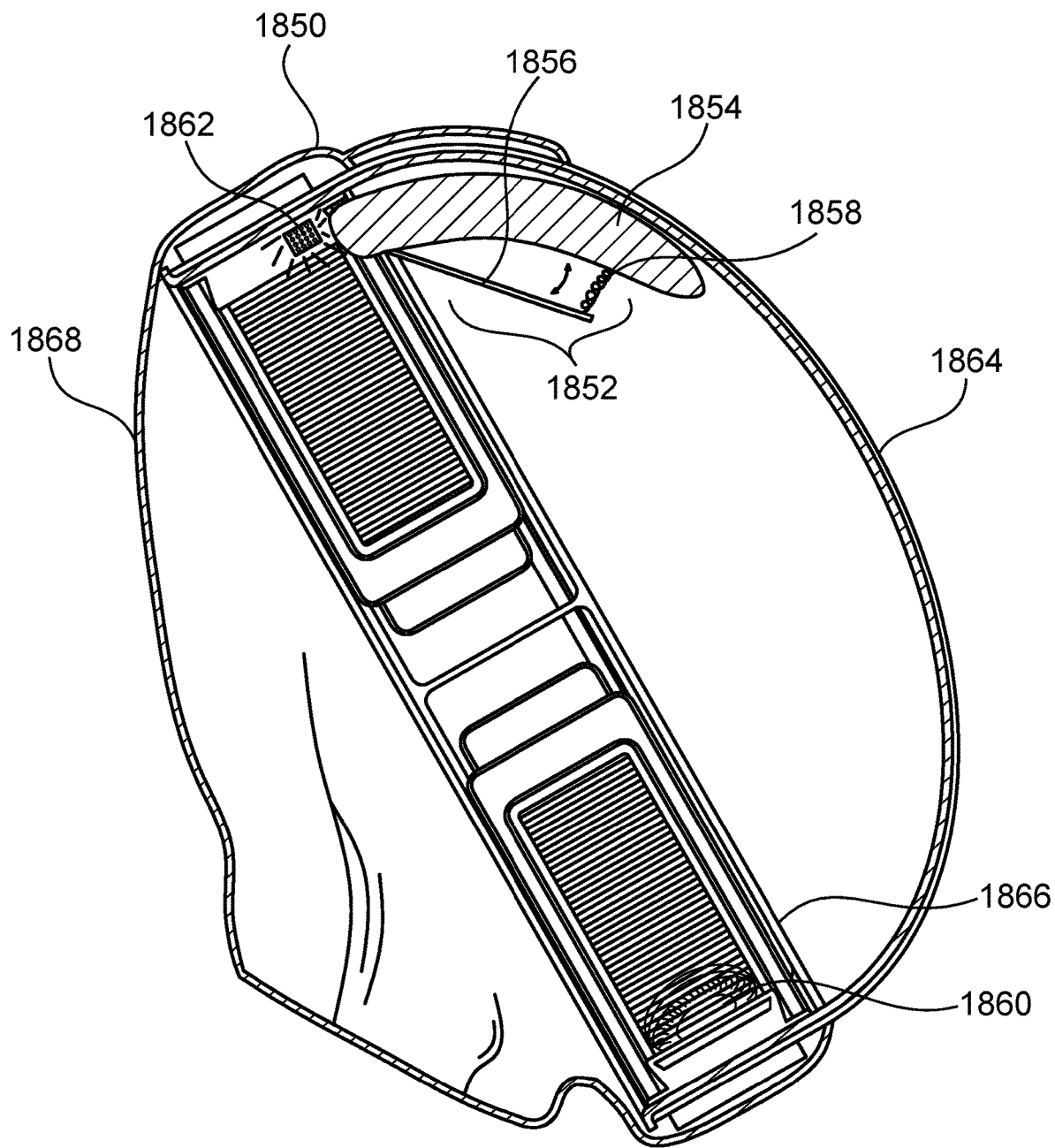
FIG. 34 is a view of user with a variable flow head covering device (VFHCD) that is controlled and monitored by an app on a smart device, according to an embodiment of the disclosure.

FIG. 34 is a view of user with a variable flow head covering device (VFHCD) 2200 that is controlled and monitored by an app on a smart device 2202, according to an embodiment of the disclosure. The VFHCD is similar to other HCD embodiments described herein comprising a flexible fabric component 2204, and rigid face shield component 2206. The VFHCD further comprises an antenna 2208 to receive a wireless signal that is extended from the top of the VFHCD. The extending antenna may be rigid or a flexible whip antenna. In other embodiments, the antenna may be hidden from view within the frame of the VFHCD or under the fabric component. In other embodiments the antenna may be in the form of wires located on the surface of the face shield.

The VFHCD comprises a controller that may include one or more communication systems, including Bluetooth communication chips, Internet Wi-Fi transceivers, network transceivers, a wireless mesh network device such as Z-Wave network transceiver, or a combination thereof to wirelessly communicate with a smart device. The controller may be mounted in the rigid component of the VFHCD. The controller is able to control various components of the VFHCD such as the rate of the air mover, humidity level, temperature, dimming of the face shield using an electrochromic layer, audio visual and communication components such as an image or video display, microphone, or speaker on demand by the user using an app on a smart device. The smart device may be a stand-alone smart device or integrated with the rigid component of the VFHCD. The one or more communication systems may communicate by a wireless signal 2210 with at least one of external remote controllers and a cloud-based network in real-time, intermittent time, or in pre-determined time intervals and lengths of time or a combination thereof.

The one or more communication systems may receive instructions from the external remote controller, generate signals 2212 instructing components of the VFHCD to operate and to monitor the status of various components. The communications system may generate a signal 2210 informing the external remote controller of the status of at least one device in the VFHCD. In an exemplary embodiment, the remote controller is a smart device such as a tablet, wearable, or mobile phone 2202 controlled by a user 2214.

The smart device communicates to a plurality of devices within the VFHCD. The smart device may also include a wireless transmitter and wireless transceiver and have a connection to each network device of the one or more devices. The connection may include a wired or wireless interface such as Bluetooth, WIFI, mesh network or similar wireless protocol.

FIGS. 35 through 37 show various exemplary graphical user interface (GUI) pages associated with an application configured to execute on a mobile device. Nevertheless, in other embodiments, the application may be configured to execute on a desktop computer, workstation, tablet, laptop, or other suitable computing device.

FIG. 35 shows a graphical user interface 2220 for monitoring and controlling functions of a variable flow head covering device (VFHCD) with an app, according to an embodiment of the disclosure. The GUI example embodiment 2220 displayed on a mobile phone 2202 displays various information and multiple indicators and control functions. The name "Michael's Head Covering Device" as displayed at the top of the screen along with standard information such as the time, temperature, weather conditions, and battery charge status of the smart device. Although the name "Michael's Head Covering Device" is used for the name of the VFHCD for illustrative purposes, the user 2214 can give the device any name. In this embodiment, the battery charge status, whether the VFHCD is plugged in a charging, and the variable fan speed indicators 2222 are displayed. The app may provide an audible alert or a visual alert for the user on the GUI if the battery level goes below a certain level where a limited amount of usage time is left. Controls for the fan speed 2224 are also shown wherein touching "−" decreases the fan speed and pressing "+" increases the fan speed. Towards the bottom of the GUI is a control function where a user can touch "ON" or "OFF" 2226 to turn the lights on in a VFHCD. The lights may be lights inside or outside of the VFHCD.

FIG. 36 shows a graphical user interface 2230 for monitoring and controlling functions of a variable flow head covering device (VFHCD), according to an embodiment of the disclosure. In this GUI embodiment 2230, the temperature and air flow rate 2232 inside the device are displayed. The temperature can be switched by touching an icon 2234 on the screen to toggle between °F and ° C. depending on what is desired by a user. Other functions 2236 may be controlled such as activating an electrochromic layer to dim the face shield, control the internal temperature of the HCD, turn up the hearing volume for the user to hear others, or turn up the speaking volume for others to better hear the user of an HCD. Electromagnetic radiation sensors may be used to determine if the electrochromic layer needs to be activated to limit amount of light entering the face shield and provide shade (i.e., shade function) to the user or by a command from the user.

In some embodiments, the mobile device app may be able to monitor and control more than one HCD. At the bottom of GUI embodiment 2230, a user can touch "Add New Device" 2238 to add another VFHCD. The VFHCD could be added by a QR code located on the VFHCD or search by the name of the VFHCD. A Bluetooth verification method could be used to create a connection between the mobile phone device and the VFHCD. A QR code located on a VFHCD could also be scanned to link the VFHCD to the mobile phone app.

FIG. 37 shows a graphical user interface 2240 for monitoring biometric information in a variable flow head covering device (VFHCD), according to an embodiment of the disclosure. In this example, various biometric data are displayed 2240 such as body temp, pulse rate (beats per minute (BPM)), breathing rate (breaths per minute (BPM)), blink rate (blinks per minute (BPM)), and oxygen saturation levels (% $O_2$) that are collected by various sensors in the VFHCD. Other biometric data may be displayed such as head orientation, closed eyes, and combinations thereof. The app may be able to store and monitor the biometric data for more than one user. This can be achieved by touching "Add Another User" 2242 shown at the bottom of the GUI. The biometric data can be selectively collected on a user if the designated user is confirmed by a fingerprint or retinal scanner. A VFHCD may further comprise a processor for receiving signals from biometric sensors and communicate biometric information to the smart device, and wherein the app is configured to receive and process biometric information and provide reports to the user.

The app may provide alerts for any information collected by the VFHCD such as performance of the VFHCD itself or biometric data collected on the user. The alerts may be programmed and set by the user or may be set based on the age, weight, height, or other information of the user.

The app may provide alerts for information collected by safety sensors in occupational safety applications such as exterior temperature, noise level, or air quality. The app may be configured to control the temperature, air flow, volume inside of the HCD based on the ambient noise levels in occupational and non-occupational settings. Air pressure differences may also be monitored by one or more sensors and relayed to the smart device and displayed by the app.

The app may receive signals from one or more sensors to test and/or monitor fitment of the system such as the detection of leaks around the seal of the flexible fabric component and the neck area of the user. The sensors may be able to detect a gas for use in testing fitment.

In some embodiments, the app may provide audio assistance to users who are blind and cannot read the GUI. The audio assistance would read what is one the GUI to the user. The volume of the audio could be controlled for the hearing impaired. The app may be used to control video images or projections within the VFHCD.

The app may be configured to provide an intercom system with one or more users using a similar HCD system.

The app may be configured to provide filter end of useful life alerts to the user based on at least one of age of the filter, increased head pressure on the filter and optical readings indicating a dirty filter.

Vibration Isolating and Noise Dampening Air Moving Device

The following embodiments describes an air moving device that is design to minimize and isolate vibrations and dampen noise caused by an air mover in a personal air filtration device.

FIG. 38 is a front view of a vibration isolating air moving device (VIAMD) 2400, according to an embodiment of the disclosure. The VIAMD comprises an air mover assembly 2402. An air mover assembly may also be referred to as a fan assembly and may be used interchangeably herein. The air mover assembly comprises an impeller 2416 contained within and supported by a housing. The fan assembly may be powered by a battery or solar cell. The battery may be a rechargeable battery. Wires 2404 from the power source are used to supply a current to operate the fan. The fan may be a multi-speed or variable speed fan that can be adjusted to a lower speed, when appropriate, to further reduce the noise from one or more air mover assemblies within an HCD. One of the fans first and second air mover assemblies can be turned off, when appropriate to further reduce the noise within the device.

The VIAMD further comprises a top fan frame 2406. The top fan frame is larger than the fan assembly 2402 and surrounds the periphery of the fan. There is a gap between the fan and the top fan frame. The gap is preferably large enough so that when the fan is in operation, the fan does not come into contact with the top fan frame such as from vibrations. The fan frame is comprised of a rigid material such as a polymer. The fan assembly frame may be rectangular, square-like, or any shape or size to be able conform to a device to provide air flow. The top frame may act as a mounting frame to mount the fan assembly to an HCD.

The VIAMD further comprises pliable or elastic members 2408 to connect the fan to the top fan frame. The members may be bands that may further be made of rubber, or other elastomer such as butyl rubber, natural or synthetic isoprene, chloroprene, nitrile rubber, or styrene-butadiene rubber. The bands hold the fan assembly in place within the front side of the top fan frame in a suspended manner. The bands are connected to the fan assembly by receiving holes 2410 located near each corner of the fan. In an exemplary embodiment, the housing has a rectangular periphery and wherein an elastic band is attached at each of the housing's four corners. The elastic bands can be thread through the holes and tied to the fan assembly. The other end of the elastic bands are connected to the top fan frame by wrapping around a frame receiving post or member 2412. Each elastic band is attached at one end to a different corner of the housing of an air assembly and is attached at another end to a different point on the rigid component of a fan frame or rigid component of the HCD. The receiving frame members protrude from an outer edge of the top fan frame. Other means may be used to connect the elastic bands to the fan and frame receiving members. In other embodiments, any combination of two or more posts may be used to connect the elastic bands to. The elastic bands can absorb vibrations during operation of the fan assembly and reduce the amount of vibrations transmitted to the rigid component of an HCD.

The VIAMD further comprises a flexible membrane 2414. The membrane comprises a silicone-based material but could be another polymeric material. The membrane can further absorb vibrations and help to dampen the sound coming from the fan. The membrane is located on the opposite side of the top fan frame 2406 from the elastic bands. The membrane spans from the top to the bottom of the top fan frame and from one side to the other side of the top fan frame. The membrane is slightly wider and longer than the frame though the membrane may be approximately the same width and length of the frame. The membrane helps to reduce air flow through the air gap. The membrane comprises an aperture to allow for air to pass through that is moved by the fan.

FIG. 39 is a rear view of a vibration isolating air moving device (VIAMD) 2400, according to an embodiment of the disclosure. In this view the rear view of the fan 2402 can be seen along with the fan impeller 2416. Also illustrated in the is view is a bottom fan frame 2418. The bottom fan frame is substantially the same width and length as the top fan frame 2406. The membrane 2414 is pinched or sandwiched in between the top and bottom frames to keep it in place. The bottom fan frame is made of a rigid polymer. In some embodiments, the bottom fan frame may be a spongy material that conforms to the device it is attached to and may further act as a resilient mount. The protruding posts 2412 from the top frame can also be seen. The bottom fan frame may act as a mounting frame to mount the air assembly to a rigid component in an HCD.

FIG. 40 is a side view of a vibration isolating air moving device (VIAMD) 2400, according to an embodiment of the disclosure. This view further illustrates the multi-component structure of the VIAMD. The bottom structure in FIG. 40 is the bottom fan frame 2418 wherein the membrane 2414 is located on the top side and secured in place by top fan frame 2406. The top and bottom fan frames are secured together by screws, clamps, or other securing mechanism. The fan assembly 2402 is located on the top side of the membrane and joined to the top fan frame by elastic bands 2408.

In some embodiments, a bottom fan frame is not used wherein the top fan frame is directly connect to a device to supply air flow from the fan. The membrane acts to form an airtight seal between the fan frame and device requiring air flow. In some embodiments, the bottom fan fame is a soft or sponge-like material to form an airtight seal to the device it is attached to. In other embodiments, a very high bonding or adhesive tape may be used to form a seal between the bottom fan frame 2418 and the device to which hit is attached to. The tape may also act as a resilient mount to further dampen and isolate vibrations.

FIG. 41 is a side view of a vibration isolating air moving device (VIAMD) 2400 showing the fan outlet and air flow, according to an embodiment of the disclosure. In this view the fan 2402 has been slightly titled to better view the exhaust air outlet 2420. When in operation, the fan pulls in intake air 2422 on the opposite side as shown in FIG. 39. The exhaust air 2424 is exhausted out the exhaust air outlet on one side of the fan. During operation, the vibrations of the fan are dissipated by the elastic bands 2408. This limits vibrations from propagating into the structure to which the VIAMD is attached to.

The vibration isolating air moving device (VIAMD) 2400 or related embodiments may be used in any of the head covering devices (HCDs) disclosed herein. The VIAMD would be directly attached to the rigid frame component to pull in or push out air through an intake or exhaust port and through an intake or exhaust filter. In some embodiments, the air mover assembly would be mounted on the rigid component of an HCD described herein without the need for a fan frame by vibration absorbing members, to thereby reduce transmission of the vibration of the air mover assembly to the rigid member, thereby reducing noise from the air mover assembly within the device. The HCD may comprise receiving members to attach one end of the elastic bands to and the other end of the elastic bands to an air mover assembly. The rigid fan assembly frame component further comprises a mounting frame surrounding either the inlet port or the outlet port in an HCD, and wherein the mounting frame comprises mounting features for receiving the other ends of the elastic bands.

The VIAMD may be used in other types of air control devices such as masks for powered air purifying respirators (PAPRs). FIG. 42 is an example of combining a PAPR mask 2450 with a vibration isolating air moving device (VIAMD) 2400, according to an embodiment of the disclosure. The PAPR mask illustrated is a commonly used PAPR mask. Any PAPR mask may be used an integrated with a VIAMD. The VIAMD is mounted to the rear of the mask but could be located elsewhere. Intake air 2452 is pulled into the mask by the fan assembly 2402. The intake air enters the mask where it may be filtered beforehand. For example, a filter may be placed over the fan on the outside of the PAPR mask or on the inside as filtered intake air 2454.

The PAPR mask may further comprise an outlet filter 2456. The outlet filter in this embodiment is located in the transparent shield component 2458 near where the mouth of a user is located. The filter may be located elsewhere such as in the cloth component 2460 of the mask. Air leaving the mask is filtered exhaust air 2462. This design is an improvement over commonly used PAPRs where a fan is located on the belt of a user and connect by a hose to the rear of the mask. These types of masks filter the air going into the mask but not the air that is exhausted from the mask. The embodiment described herein not only protects the wearer of the PAPR mask but also protects a patient being cared for by the wearer in the instance where the wearer may be infected with a contagious disease.

The invention has been described with reference to various specific and preferred embodiments and techniques. Nevertheless, it is understood that many variations and modifications may be made while remaining within the spirit and scope of the invention.

What is claimed is:

1. A personal air filtration system comprising:
   a rigid component comprising a rigid, oval-shaped frame, with a top, oval-shaped edge, and a transparent face shield, the transparent face shield having a bottom, oval-shaped edge, the bottom, oval-shaped edge is attached along an entire top, oval-shaped edge of the frame;
   wherein a bottom portion of the oval-shaped frame is configured to pass below the chin of a user and an upper portion of the oval-shaped frame is configured to pass above the user's forehead;
   a flexible component attached around the entire oval-shaped frame, wherein the rigid component and the flexible component are configured to combine to cover an entire head of the user and configured to form a seal around the user's neck;
   an intake port with an inlet filter located on the rigid oval-shaped frame;
   an exhaust port located on the rigid oval-shaped frame;
   an air mover affixed to the oval-shaped frame configured for causing filtered air to enter the intake port and exhaust air to exit the exhaust port; and
   an application running on a user's smart device, wherein the app is configured to control and monitor operation of the personal air filtration system.

2. The personal air filtration system of claim 1, wherein the user's smart device is integrated into the rigid oval-shaped frame.

3. The personal air filtration system of claim 2, wherein the user's smart device provides wireless communication for the user.

4. The personal air filtration system of claim 1, wherein the user's smart device is a separate smart phone.

5. The personal air filtration system of claim 4, further comprising a microphone and speakers mounted to the rigid oval-shaped frame, which the microphone and the speakers are configured to communicate wirelessly with the user's smart device to enable the user to place and receive telephone calls over the smart phone.

6. The personal air filtration system of claim 1, wherein the smart device is a wearable smart device.

7. The personal air filtration system of claim 1, wherein the user's smart device is configured to communicate wirelessly with a controller mounted to the rigid oval-shaped frame, and wherein the controller is configured to control a rate of the air mover.

8. The personal air filtration system of claim 1, wherein the air mover is powered by a battery and the application is configured to monitor the status of the battery and provide information to the user on the status of the battery.

9. The personal air filtration system of claim 1, wherein the transparent face shield is hemi-ellipsoid in shape.

10. The personal air filtration system of claim 1, wherein the personal air filtration system further comprises:
    a first microphone on an inner surface of the rigid oval-shaped frame;
    a second microphone on an outer surface of the rigid oval-shaped frame;
    a first speaker mounted on an inner surface of the rigid oval-shaped frame; and
    a second speaker mounted on an outer surface of the rigid oval-shaped frame;
    wherein the application is configured to facilitate oral communication by the user.

11. The personal air filtration system of claim 10, wherein the application is configured to adjust volume based on ambient noise levels.

12. The personal air filtration system of claim 1, further comprising a video display projected on an inner surface of the transparent face shield and wherein the application is configured for the user to select and control the video display.

13. The personal air filtration system of claim 1, further comprising a shade function whereby the amount of electromagnetic radiation entering through the transparent face shield can be reduced, and wherein the application is configured to control the shade function based upon instructions from the user and signals from electromagnetic radiation sensors.

14. The personal air filtration system of claim 1, wherein the personal air filtration system further comprises sensors configured to detect leaks in the seal and wherein the application receives signals from the sensors to test and/or monitor a fitment of the personal air filtration system.

15. The personal air filtration system of claim 14, wherein the sensors are configured to detect a gas used in testing the fitment.

16. The personal air filtration system of claim 1, wherein the application is configured to provide an intercom with a second user of a similar system.

17. The personal air filtration system of claim 1, wherein the app is further configured to provide filter end of useful life alerts to the user based on at least one of age of the filter, increased head pressure on the filter and optical readings indicating a dirty filter.

18. The personal air filtration system of claim 1, further comprising biometric sensors and a processor for receiving signals from the biometric sensors located on the oval-shaped frame and communicate biometric information to the smart device, and wherein the application is configured to receive and process biometric information and is configured to provide reports to the user.

19. The personal air filtration system of claim 18, wherein the biometric sensors are configured to measure biometric information selected from the group consisting of body temperature, pulse rate, pulse oximetry, respiration rate, blink rate, head orientation and combinations thereof.

20. The personal air filtration system of claim 19, wherein the smart device communicates wirelessly with a controller mounted to the rigid oval-shaped frame, and wherein the controller is configured to control the rate of the air mover and wherein the app is configured to send signals to the controller to adjust the rate of the air mover in response to one or more types of biometric information.

21. The personal air filtration system of claim 1, further comprising a device for controlling the personal environment mounted to the rigid oval-shaped frame, which is configured to adjust the temperature and/or the humidity around the user's head, and wherein the application is configured to allow the user to make those adjustments and configured to make those adjustments in response to biometric data and/or ambient environmental data.

* * * * *